US009549558B2

United States Patent
Newton et al.

(10) Patent No.: US 9,549,558 B2
(45) Date of Patent: Jan. 24, 2017

(54) HERBICIDAL AZINES

(71) Applicant: BASF SE, Ludwigshafen (DE)

(72) Inventors: Trevor William Newton, Neustadt (DE); Florian Vogt, Mannheim (DE); Julia Major, Freinsheim (DE); Kristin Hanzlik, Bobenheim am Berg (DE); Liliana Parra Rapado, Offenburg (DE); Markus Kordes, Frankenthal (DE); Thomas Seitz, Viernheim (DE); Matthias Witschel, Bad Duerkheim (DE); Klaus Kreuz, Denzlingen (DE); Johannes Hutzler, Waldsee (DE); Richard Roger Evans, Limburgerhof (DE); Jens Lerchl, Golm (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/437,981

(22) PCT Filed: Oct. 22, 2013

(86) PCT No.: PCT/EP2013/072055
§ 371 (c)(1),
(2) Date: Apr. 23, 2015

(87) PCT Pub. No.: WO2014/064094
PCT Pub. Date: May 1, 2014

(65) Prior Publication Data
US 2015/0289510 A1    Oct. 15, 2015

(30) Foreign Application Priority Data
Oct. 24, 2012 (EP) .................... 12189762

(51) Int. Cl.
| *C07D 251/48* | (2006.01) |
|---|---|
| *A01N 43/66* | (2006.01) |
| *A01N 43/68* | (2006.01) |
| *C07C 279/18* | (2006.01) |
| *C07D 251/42* | (2006.01) |
| *C07C 279/26* | (2006.01) |
| *C07D 251/22* | (2006.01) |

(52) U.S. Cl.
CPC ............ *A01N 43/68* (2013.01); *C07C 279/26* (2013.01); *C07D 251/22* (2013.01); *C07D 251/42* (2013.01); *C07D 251/48* (2013.01)

(58) Field of Classification Search
CPC ............................. C07D 251/48; A01N 43/66
USPC ................... 544/204, 211; 504/227
See application file for complete search history.

(56) References Cited

U.S. PATENT DOCUMENTS

| 3,816,419 A | 6/1974 | Cross et al. |
|---|---|---|
| 3,996,232 A | 12/1976 | Diamond et al. |
| 6,239,071 B1 | 5/2001 | Giencke et al. |
| 7,002,011 B1 | 2/2006 | Zindel et al. |

FOREIGN PATENT DOCUMENTS

| DE | 195 31 084 | 2/1997 |
|---|---|---|
| DE | 193 30 902 | 1/2000 |

OTHER PUBLICATIONS

Eisa et al. Pakistan Journal of Scientific and Industrial Research (1988), 31(7), 474-6; CA 113: 171987,1990. CAPLUS abstract provided.*
International Preliminary Report on Patentability dated Oct. 22, 2014, prepared in International Application No. PCT/EP2013/072055.
International Search Report dated Nov. 14, 2013, prepared in International Application No. PCT/EP2013/072055.
Kreutzberger, Alfred, et al. "Fluorinated 2-amino-4-arylamine-s-triazines", Liebigs Ann. Chem. 1977, p. 1625-1632.

* cited by examiner

*Primary Examiner* — Venkataraman Balasubramanian
(74) *Attorney, Agent, or Firm* — Brinks Gilson & Lione

(57) ABSTRACT

The present invention relates to azines of formula (I)

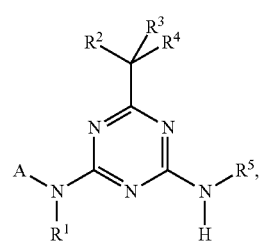

wherein the variables are defined according to the description,
processes and intermediated for preparing them, compositions comprising them and their use as herbicides, i.e. for controlling harmful plants and a method for controlling unwanted vegetation which comprises allowing a herbicidal effective amount of at least one azine of the formula I to act on plants, their seed and/or their habitat.

21 Claims, No Drawings

HERBICIDAL AZINES

This application is a National Stage application of International Application No. PCT/EP2013/072055, filed Oct. 22, 2013, the entire contents of which is hereby incorporated herein by reference. This application also claims priority under 35 U.S.C. §119 to European Patent Application No. 12189762.3, filed Oct. 24, 2012, the entire contents of which is hereby incorporated herein by reference.

The present invention relates to azines of the general formula (I) defined below and to their use as herbicides. Moreover, the invention relates to agrochemical compositions for crop protection and to a method for controlling unwanted vegetation.

U.S. Pat. No. 3,816,419 describes structurally similar compounds for which herbicidal action is stated, which differ from the according to the present invention.

However, the herbicidal properties of these known compounds with regard to the harmful plants are not always entirely satisfactory.

It is therefore an object of the present invention to provide azines of formula (I) having improved herbicidal action. To be provided are in particular azines of formula (I) which have high herbicidal activity, in particular even at low application rates, and which are sufficiently compatible with crop plants for commercial utilization.

These and further objects are achieved by azines of formula (I), defined below, and by their agriculturally suitable salts.

Accordingly, the present invention provides azines of formula (I)

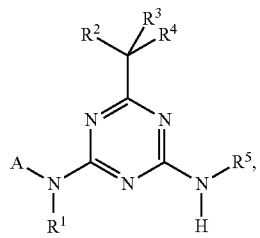

I wherein
A is phenyl, which is substituted by two to five substituents selected from the group consisting of halogen, CN, $NO_2$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_1$-$C_6$-haloalkynyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;

$R^1$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or
$R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
wherein the $C_3$-$C_6$-cycloalkyl, $C_3$-$C_6$-cycloalkenyl, or three- to six-membered heterocyclyl is unsubstituted or substituted by one to three substituents selected from halogen, CN, $C_1$-$C_6$-alkyl and $C_1$-$C_6$-alkoxy; and $R^5$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

Preferably the present invention provides azines of formula (I), wherein
A is 2-fluoro-phenyl, which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)carbonyl;

$R^1$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or
$R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
wherein the $C_3$-$C_6$-cycloalkyl, $C_3$-$C_6$-cycloalkenyl or and three- to six-membered heterocyclyl is unsubstituted or substituted by one to three substituents selected from halogen, CN, $C_1$-$C_6$-alkyl and $C_1$-$C_6$-alkoxy; and $R^5$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

The present invention also provides agrochemical compositions comprising at least one azines of formula (I) and auxiliaries customary for formulating crop protection agents.

The present invention also provides the use of azines of formula (I) as herbicides, i.e. for controlling harmful plants.

The present invention furthermore provides a method for controlling unwanted vegetation where a herbicidal effective amount of at least one azines of the formula (I) is allowed to act on plants, their seeds and/or their habitat. Application can be done before, during and/or after, preferably during and/or after, the emergence of the undesirable plants.

Moreover, the invention relates to processes and intermediates for preparing azines of formula (I).

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the azines of formula (I) as described herein are capable of forming geometrical isomers, for example E/Z isomers, it is possible to use both, the pure isomers and mixtures thereof, in the compositions according to the invention.

If the azines of formula (I) as described herein have one or more centres of chirality and, as a consequence, are present as enantiomers or diastereomers, it is possible to use both, the pure enantiomers and diastereomers and their mixtures, in the compositions according to the invention.

If the azines of formula (I) as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the variables, e.g. $R^1$ to $R^5$, are—like the term halogen—collective terms for individual enumerations of the individual group members. The term halogen denotes in each case fluorine, chlorine, bromine or iodine. All hydrocarbon chains, i.e. all alkyl, haloalkyl, alkenyl, alkynyl, alkoxy, alkylthio, alkylsulfinyl, alkylsulfonyl, (alkyl)amino, di(alkyl)amino chains can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$, n-butyl, $CH(CH_3)$—$C_2H_5$, $CH_2$—CH$(CH_3)_2$ and $C(CH_3)_3$;

$C_1$-$C_6$-alkyl and also the $C_1$-$C_6$-alkyl moieties of ($C_1$-$C_6$-alkyl)carbonyl, $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl: monocyclic saturated hydrocarbons having 3 to 6 ring members, such as cyclopropyl, cyclobutyl, cyclopentyl and cyclohexyl;

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of ($C_1$-$C_6$-alkoxy)carbonyl, $C_1$-$C_6$-alkoxy-$C_1$-$C_6$-alkyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—): z.B. methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentyl-sulfinyl, 1,1-dimethylbutyl-sulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

($C_1$-$C_4$-alkyl)amino: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino: for example N,N-dimethylamino, N,N-diethylamino, N,N-di(1-methylethyl)amino, N,N-dipropylamino, N,N-dibutylamino, N,N-di(1-methylpropyl)-amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methyl-ethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)-amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)-amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

three- to six-membered heterocyclyl: monocyclic saturated or partially unsaturated hydrocarbon having three to six ring members as mentioned above which, in addition to carbon atoms, contains one or two heteroatoms selected from O, S and N;

for example 2-oxiranyl, 2-oxetanyl, 3-oxetanyl, 2-aziridinyl, 3-thietanyl, 1-azetidinyl, 2-azetidinyl, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl;

for example 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl;

for example 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydro-thiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, tetrahydro-1,3-oxazin-2-yl, tetrahydro-1,3-oxazin-6-yl, 2-morpholinyl, 3-morpholinyl;

for example 2H-pyran-2-yl, 2H-pyran-3-yl, 2H-pyran-4-yl, 2H-pyran-5-yl, 2H-pyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

The preferred embodiments of the invention mentioned herein below have to be understood as being preferred either independently from each other or in combination with one another.

According to a preferred embodiment of the invention preference is also given to those azines of formula (I), wherein the variables, either independently of one another or in combination with one another, have the following meanings:

Preferred are the azines of formula (I), wherein

A is phenyl, which is substituted by two to five substituents selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;

particularly preferred phenyl, which is substituted by two to five substituents selected from the group consisting of halogen, CN, C$_1$-C$_6$-alkyl and C$_1$-C$_6$-alkoxy;
particularly preferred selected from halogen and CN;
also particularly preferred selected from the group consisting of F, Cl, CN and CH$_3$;
especially preferred selected from the group consisting of F, Cl and CN;

especially preferred phenyl, which is substituted by two to four substituents
selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;
particularly preferred selected from the group consisting of halogen, CN, C$_1$-C$_6$-alkyl and C$_1$-C$_6$-alkoxy;
especially preferred selected from halogen and CN;
also especially preferred selected from the group consisting of F, Cl, CN and CH$_3$;
more preferred selected from the group consisting of F, Cl and CN;

more preferred phenyl, which is substituted by two substituents
selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;
particularly preferred selected from the group consisting of halogen, CN, C$_1$-C$_6$-alkyl and C$_1$-C$_6$-alkoxy;
especially preferred selected from halogen and CN;
also especially preferred selected from the group consisting of F, Cl, CN and CH$_3$;
more preferred selected from the group consisting of F, Cl and CN;

also more preferred phenyl, which is substituted by three substituents
selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;
particularly preferred selected from the group consisting of halogen, CN, C$_1$-C$_6$-alkyl and C$_1$-C$_6$-alkoxy;
especially preferred selected from halogen and CN;
also especially preferred selected from the group consisting of F, Cl, CN and CH$_3$;
more preferred selected from the group consisting of F, Cl and CN;

also more preferred phenyl, which is substituted by four substituents
selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;
particularly preferred selected from the group consisting of halogen, CN, C$_1$-C$_6$-alkyl and C$_1$-C$_6$-alkoxy;
especially preferred selected from halogen and CN;
also especially preferred selected from the group consisting of F, Cl, CN and CH$_3$;
more preferred selected from the group consisting of F, Cl and CN.

Also preferred are the azines of formula (I), wherein
A is

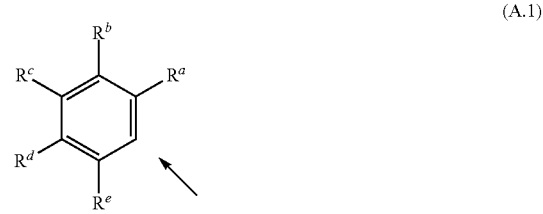

(A.1)

wherein
R$^a$ and R$^e$ independently of one another are halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl; and
R$^b$, R$^c$ and R$^d$ independently of one another are hydrogen, halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;
particularly preferred R$^a$ and R$^e$ independently of one another are halogen, CN, C$_1$-C$_6$-alkyl or C$_1$-C$_6$-alkoxy; and
R$^b$, R$^c$ and R$^d$ independently of one another are hydrogen, halogen, CN, NO$_2$, C$_1$-C$_6$-alkyl, C$_1$-C$_6$-haloalkyl or C$_1$-C$_6$-alkoxy;
especially preferred R$^a$ and R$^e$ independently of one another are halogen or CN; and
R$^b$, R$^c$ and R$^d$ independently of one another are hydrogen, halogen, CN, C$_1$-C$_6$-alkyl or C$_1$-C$_6$-alkoxy;
more preferred R$^a$ and R$^e$ are halogen; and
R$^b$, R$^c$ and R$^d$ independently of one another are hydrogen, halogen or CN;
most preferred R$^a$ and R$^e$ are halogen; and
R$^b$, R$^c$ and R$^d$ are hydrogen;
also most preferred R$^a$, R$^b$, R$^d$ and R$^e$ are halogen; and R$^c$ hydrogen;
also most preferred R$^a$, R$^b$, R$^c$, R$^d$ and R$^e$ are halogen.

Also preferred are the azines of formula (I), wherein
A is

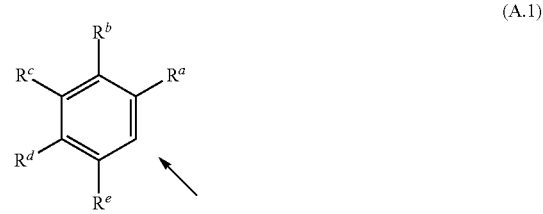

(A.1)

wherein $R^a$ is halogen or CN;
$R^b$ and $R^d$ are H, halogen or CN;
$R^c$ is H or halogen;
$R^e$ is halogen, CN or $C_1$-$C_6$-alkyl;
particularly preferred $R^a$ is halogen;
$R^b$, $R^c$ and $R^d$ are H or halogen; and
$R^e$ is halogen or CN;
especially preferred $R^a$, $R^b$, $R^d$ and $R^e$ are halogen; and
$R^c$ is H or halogen;
more preferred $R^a$, $R^b$, $R^d$ and $R^e$ are F; and
$R^c$ is H or F.

Especially preferred are the azines of formula (I), wherein A is selected from the group consisting of (A.1.1), (A.1.2) and (A.1.3);
more preferred selected from the group consisting of (A.1.2) and (A.1.3);

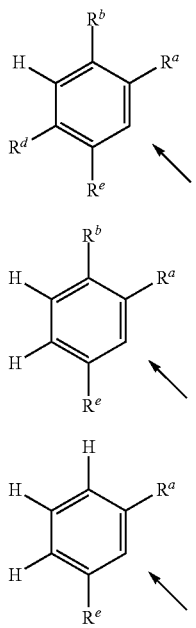

wherein
$R^a$ and $R^e$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and
$R^b$ and $R^d$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred $R^a$ and $R^e$ independently of one another are halogen, CN, $C_1$-$C_6$-alkyl or $C_1$-$C_6$-alkoxy; and
$R^b$ and $R^d$ independently of one another are halogen, CN, $NO_2$, $C_1$-$C_6$-alkyl, $C_1$-$C_6$-haloalkyl or $C_1$-$C_6$-alkoxy;
especially preferred $R^a$ and $R^e$ independently of one another halogen or CN; and
$R^b$ and $R^d$ independently of one another are halogen, CN, $C_1$-$C_6$-alkyl or $C_1$-$C_6$-alkoxy;

more preferred $R^a$ and $R^e$ are halogen; and
$R^b$ and $R^d$ independently of one another are halogen or CN;
most preferred $R^a$, $R^b$, $R^d$ and $R^e$ are halogen.

Also especially preferred are the azines of formula (I), wherein
A is

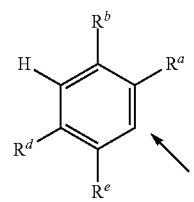

wherein $R^a$, $R^b$, $R^d$ and $R^e$ have the meanings, in particular the preferred meanings, as defined above.

Also especially preferred are the azines of formula (I), wherein
A is

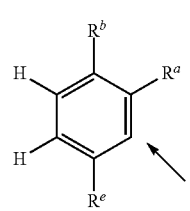

wherein $R^a$, $R^b$ and $R^e$ have the meanings, in particular the preferred meanings, as defined above.

Also especially preferred are the azines of formula (I), wherein
A is

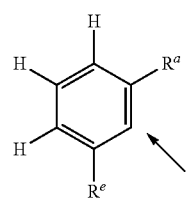

wherein $R^a$ and $R^e$ have the meanings, in particular the preferred meanings, as defined above.

Also preferred are the azines of formula (I), wherein
A is 2-fluoro-phenyl, which is substituted by one to four substituents selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)carbonyl;
particularly preferred 2-fluoro-phenyl, which is substituted by one to four substituents
selected from the group consisting of halogen, CN, $C_1$-$C_6$-alkyl and $C_1$-$C_6$-alkoxy;
particularly preferred selected from halogen and CN;

also particularly preferred selected from the group consisting of F, Cl, CN and CH$_3$;
especially preferred selected from the group consisting of F, Cl and CN;
especially preferred 2-fluoro-phenyl, which is substituted by one to three substituents
selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl and (C$_1$-C$_6$-alkoxy)carbonyl;
particularly preferred selected from the group consisting of halogen, CN, C$_1$-C$_6$-alkyl and C$_1$-C$_6$-alkoxy;
especially preferred selected from halogen and CN;
also especially preferred selected from the group consisting of F, Cl, CN and CH$_3$;
more preferred selected from the group consisting of F, Cl and CN;
more preferred 2-fluoro-phenyl, which is substituted by one substituent
selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl and (C$_1$-C$_6$-alkoxy)carbonyl;
particularly preferred selected from the group consisting of halogen, CN, C$_1$-C$_6$-alkyl and C$_1$-C$_6$-alkoxy;
especially preferred selected from halogen and CN;
also especially preferred selected from the group consisting of F, Cl, CN and CH$_3$;
more preferred selected from the group consisting of F, Cl and CN;
also more preferred 2-fluoro-phenyl, which is substituted by two substituents
selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl and (C$_1$-C$_6$-alkoxy)carbonyl;
particularly preferred selected from the group consisting of halogen, CN, C$_1$-C$_6$-alkyl and C$_1$-C$_6$-alkoxy;
especially preferred selected from halogen and CN;
also especially preferred selected from the group consisting of F, Cl, CN and CH$_3$;
more preferred selected from the group consisting of F, Cl and CN;
also more preferred 2-fluoro-phenyl, which is substituted by three substituents
selected from the group consisting of halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl and (C$_1$-C$_6$-alkoxy)carbonyl;
particularly preferred selected from the group consisting of halogen, CN, C$_1$-C$_6$-alkyl and C$_1$-C$_6$-alkoxy;
especially preferred selected from halogen and CN;
also especially preferred selected from the group consisting of F, Cl, CN and CH$_3$;
more preferred selected from the group consisting of F, Cl and CN.

Also preferred are the azines of formula (I), wherein A is (A.1a)

wherein
$R^a$ is halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl; and
$R^b$, $R^c$ and $R^d$ independently of one another are hydrogen, halogen, CN, NO$_2$, C$_1$-C$_6$-alkyl, C$_1$-C$_6$-haloalkyl, OH, C$_1$-C$_6$-alkoxy, C$_1$-C$_6$-alkylthio, (C$_1$-C$_6$-alkyl)sulfinyl, (C$_1$-C$_6$-alkyl)sulfonyl, amino, (C$_1$-C$_6$-alkyl)amino, di(C$_1$-C$_6$-alkyl)amino, (C$_1$-C$_6$-alkyl)carbonyl, (C$_1$-C$_6$-alkoxy)carbonyl;
particularly preferred $R^a$ is halogen, CN, C$_1$-C$_6$-alkyl or C$_1$-C$_6$-alkoxy; and
$R^b$, $R^c$ and $R^d$ independently of one another are hydrogen, halogen, CN, NO$_2$, C$_1$-C$_6$-alkyl, C$_1$-C$_6$-haloalkyl or C$_1$-C$_6$-alkoxy;
especially preferred $R^a$ is halogen or CN; and
$R^b$, $R^c$ and $R^d$ independently of one another are hydrogen, halogen, CN, C$_1$-C$_6$-alkyl or C$_1$-C$_6$-alkoxy;
more preferred $R^a$ is halogen; and
$R^b$, $R^c$ and $R^d$ independently of one another are hydrogen, halogen or CN;
most preferred $R^a$ is halogen; and
$R^b$, $R^c$ and $R^d$ are hydrogen;
also most preferred $R^a$, $R^b$ and $R^d$ are halogen; and
$R^c$ is hydrogen;
also most preferred $R^a$, $R^b$, $R^c$ and $R^d$ are halogen.
Also preferred are the azines of formula (I), wherein A is (A.1a)

wherein $R^a$ is halogen, CN or C$_1$-C$_6$-alkyl;
$R^b$ and $R^d$ are H, halogen or CN; and
$R^c$ is H or halogen;
particularly preferred $R^a$ is halogen or CN; and
$R^b$, $R^c$ and $R^d$ are H or halogen;
especially preferred $R^a$, $R^b$ and $R^d$ are halogen; and
$R^c$ is H or halogen;
Also especially preferred $R^a$, $R^b$ and $R^d$ are halogen; and
$R^c$ is H, F, Br or I;
more preferred $R^a$, $R^b$ and $R^d$ are F; and
$R^c$ is F, Br or I;
also more preferred $R^a$, $R^b$ and $R^d$ are F; and
$R^c$ is H or F.

Especially preferred are the azines of formula (I), wherein A is selected from the group consisting of (A.1a.1), (A.1a.2) and (A.1a.3);
more preferred selected from the group consisting of (A.1.2) and (A.1.3);

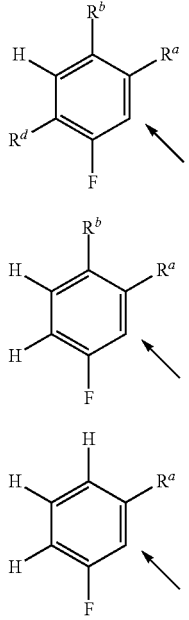

(A.1a.1)

(A.1a.2)

(A.1a.3)

wherein
$R^a$ is halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl; and
$R^b$ and $R^d$ independently of one another are halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
particularly preferred $R^a$ is halogen, CN, $C_1$-$C_6$-alkyl or $C_1$-$C_6$-alkoxy; and
$R^b$ and $R^d$ independently of one another are halogen, CN, $NO_2$, $C_1$-$C_6$-alkyl, $C_1$-$C_6$-haloalkyl or $C_1$-$C_6$-alkoxy;
especially preferred $R^a$ is halogen or CN; and
$R^b$ and $R^d$ independently of one another are halogen, CN, $C_1$-$C_6$-alkyl or $C_1$-$C_6$-alkoxy;
more preferred $R^a$ is halogen; and
$R^b$ and $R^d$ independently of one another are halogen or CN;
most preferred $R^a$, $R^b$ and $R^d$ are halogen.

Also especially preferred are the azines of formula (I), wherein
A is

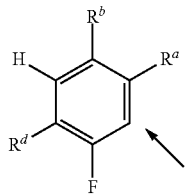

(A.1a.1)

wherein $R^a$, $R^b$ and $R^d$ have the meanings, in particular the preferred meanings, as defined above.

Also especially preferred are the azines of formula (I), wherein
A is

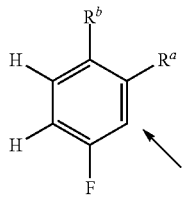

(A.1a.2)

wherein $R^a$ and $R^b$ have the meanings, in particular the preferred meanings, as defined above.

Also especially preferred are the azines of formula (I), wherein
A is

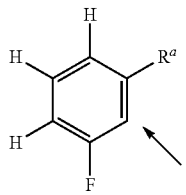

(A.1a.3)

wherein $R^a$ has the meanings, in particular the preferred meanings, as defined above.

Also preferred are the azines of formula (I), wherein
$R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
especially preferred H, CN, $CH_3$, $CH_2OCH_3$, $OCH_3$, $COCH_3$ or $SO_2CH_3$;
more preferred hydrogen.

Also preferred are the azines of formula (I), wherein
$R^2$ is H, halogen, $C_1$-$C_6$-alkyl or $C_1$-$C_6$-haloalkyl;
particularly preferred halogen, $C_1$-$C_6$-alkyl or $C_1$-$C_6$-haloalkyl;
also particularly preferred H, F, Cl, $CH_3$ or $CF_3$.

Also preferred are the azines of formula (I), wherein
$R^3$ and $R^4$ are
independently of one another H, halogen, $C_1$-$C_6$-alkyl or $C_1$-$C_6$-haloalkyl; or together with the carbon atom to which they are attached form a moiety selected from the group consisting of $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;
independently of one another particularly preferred H, halogen, $C_1$-$C_6$-alkyl or $C_1$-$C_6$-haloalkyl; or
together with the carbon atom to which they are attached form a moiety selected from the group consisting of $C_3$-$C_6$-cycloalkyl and $C_3$-$C_6$-cycloalkenyl, wherein the $C_3$-$C_6$-cycloalkyl or $C_3$-$C_6$-cycloalkenyl is unsubstituted or substituted by one to three substituents selected from halogen, CN, $C_1$-$C_6$-alkyl and $C_1$-$C_6$-alkoxy;
  independently of one another especially preferred H, halogen, $C_1$-$C_6$-alkyl or $C_1$-$C_6$-haloalkyl;
  independently of one another more preferred H, halogen or $C_1$-$C_6$-alkyl.
Also preferred are the azines of formula (I), wherein
  $R^2$ is H, halogen, $C_1$-$C_6$-alkyl; and
  $R^3$ and $R^4$ are independently of one another H, halogen, $C_1$-$C_6$-alkyl, or together with the carbon atom to which they are attached form a $C_3$-$C_6$-cycloalkyl;
  particularly preferred $R^2$ is H, halogen or $C_1$-$C_6$-alkyl;
    $R^3$ is $C_1$-$C_6$-alkyl;
    $R^4$ is H, halogen or $C_1$-$C_6$-alkyl;
    $R^3$ and $R^4$ together with the carbon atom to which they are attached form a $C_3$-$C_6$-cycloalkyl;
  especially preferred $R^2$ is halogen or $C_1$-$C_6$-alkyl;
    $R^3$ is $C_1$-$C_6$-alkyl;
    $R^4$ is H or $C_1$-$C_6$-alkyl;
  more preferred $R^2$ is halogen; and
    $R^3$ and $R^4$ are $C_1$-$C_6$-alkyl.
Also preferred are the azines of formula (I), wherein
  $R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
  especially preferred H, CN, $CH_3$, $CH_2OCH_3$, $OCH_3$, $COCH_3$ or $SO_2CH_3$;
  more preferred hydrogen.
Also preferred are the azines of formula (I), wherein
  A is phenyl, which is substituted by two to five substituents
    selected from the group consisting of halogen, CN, $C_1$-$C_6$-alkyl and $C_1$-$C_6$-alkoxy;
    particularly preferred selected from halogen and CN;
    also particularly preferred selected from the group consisting of F, Cl, CN and $CH_3$;
    especially preferred selected from the group consisting of F, Cl and CN;
  particularly preferred phenyl, which is substituted by two to four substituents
    selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
      particularly preferred selected from the group consisting of halogen, CN, $C_1$-$C_6$-alkyl and $C_1$-$C_6$-alkoxy;
      especially preferred selected from halogen and CN;
      also especially preferred selected from the group consisting of F, Cl, CN and $CH_3$;
      more preferred selected from the group consisting of F, Cl and CN;
  especially preferred phenyl, which is substituted by two substituents
    selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
      particularly preferred selected from the group consisting of halogen, CN, $C_1$-$C_6$-alkyl and $C_1$-$C_6$-alkoxy;
      especially preferred selected from halogen and CN;
      also especially preferred selected from the group consisting of F, Cl, CN and $CH_3$;
      more preferred selected from the group consisting of F, Cl and CN;
  also especially preferred phenyl, which is substituted by three substituents
    selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
      particularly preferred selected from the group consisting of halogen, CN, $C_1$-$C_6$-alkyl and $C_1$-$C_6$-alkoxy;
      especially preferred selected from halogen and CN;
      also especially preferred selected from the group consisting of F, Cl, CN and $CH_3$;
      more preferred selected from the group consisting of F, Cl and CN;
  also specially preferred phenyl, which is substituted by four substituents
    selected from the group consisting of halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl;
      particularly preferred selected from the group consisting of halogen, CN, $C_1$-$C_6$-alkyl and $C_1$-$C_6$-alkoxy;
      especially preferred selected from halogen and CN;
      also especially preferred selected from the group consisting of F, Cl, CN and $CH_3$;
      more preferred selected from the group consisting of F, Cl and CN;
  $R^1$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
    particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
    especially preferred H, CN, $CH_3$, $CH_2OCH_3$, $OCH_3$, $COCH_3$ or $SO_2CH_3$;
    more preferred hydrogen.
  $R^2$ is H, halogen, $C_1$-$C_6$-alkyl or $C_1$-$C_6$-haloalkyl;
    particularly preferred halogen, $C_1$-$C_6$-alkyl or $C_1$-$C_6$-haloalkyl;
    also particularly preferred H, F, $CH_3$ or $CF_3$;
  $R^3$ and $R^4$ are independently of one another H, halogen, $C_1$-$C_6$-alkyl or $C_1$-$C_6$-haloalkyl; or
    together with the carbon atom to which they are attached form a moiety selected from the group consisting of $C_3$-$C_6$-cycloalkyl, $C_3$-$C_6$-cycloalkenyl and three- to six-membered heterocyclyl,
      wherein the $C_3$-$C_6$-cycloalkyl, $C_3$-$C_6$-cycloalkenyl or the three- to six-membered heterocyclyl is unsubstituted or substituted by one to three substituents selected from halogen, CN, $C_1$-$C_6$-alkyl and $C_1$-$C_6$-alkoxy;
    independently of one another particularly preferred H, halogen, $C_1$-$C_6$-alkyl or $C_1$-$C_6$-haloalkyl; or
    together with the carbon atom to which they are attached form a moiety selected from the group consisting of $C_3$-$C_6$-cycloalkyl and $C_3$-$C_6$-cycloalkenyl, wherein the $C_3$-$C_6$-cycloalkyl or $C_3$-$C_6$-cycloalkenyl is unsubstituted or substituted by one to three substituents selected from halogen, CN, and $C_1$-$C_6$-alkoxy;
independently of one another especially preferred H, halogen, $C_1$-$C_6$-alkyl or $C_1$-$C_6$-haloalkyl;
independently of one another more preferred H, halogen or $C_1$-$C_6$-alkyl;
and
$R^5$ is H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
particularly preferred H, CN, $C_1$-$C_6$-alkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl;
especially preferred H, CN, $CH_3$, $CH_2OCH_3$, $OCH_3$, $COCH_3$ or $SO_2CH_3$;
more preferred hydrogen.

Particular preference is given to azines of formula (I.a), which correspond to azines of formula (I) wherein A is (A.1) and $R^1$ and $R^5$ are H:

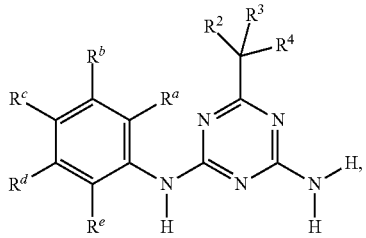

I.a wherein the variables $R^a$, $R^b$, $R^c$, $R^d$, $R^e$, $R^2$, $R^3$ and $R^4$ have the meanings, in particular the preferred meanings, as defined above;
special preference is given to the azines of the formulae (I.a.1) to (I.a.1406) of Table A, where the definitions of the variables $R^a$, $R^b$, $R^c$, $R^d$, $R^e$, $R^2$, $R^3$ and $R^4$ are of particular importance for the compounds according to the invention not only in combination with one another but in each case also on their own:

TABLE A

| No. | $R^a$ | $R^b$ | $R^c$ | $R^d$ | $R^e$ | $R^2$ | $R^3$ | $R^4$ |
|---|---|---|---|---|---|---|---|---|
| I.a.1 | F | H | H | H | F | $CH_3$ | H | H |
| I.a.2 | Cl | H | H | H | F | $CH_3$ | H | H |
| I.a.3 | Br | H | H | H | F | $CH_3$ | H | H |
| I.a.4 | CN | H | H | H | F | $CH_3$ | H | H |
| I.a.5 | $CH_3$ | H | H | H | F | $CH_3$ | H | H |
| I.a.6 | F | H | H | F | F | $CH_3$ | H | H |
| I.a.7 | Cl | H | H | F | F | $CH_3$ | H | H |
| I.a.8 | F | H | H | Cl | F | $CH_3$ | H | H |
| I.a.9 | Cl | H | H | F | F | $CH_3$ | H | H |
| I.a.10 | CN | H | H | F | F | $CH_3$ | H | H |
| I.a.11 | F | H | H | CN | F | $CH_3$ | H | H |
| I.a.12 | CN | H | F | H | F | $CH_3$ | H | H |
| I.a.13 | F | H | F | H | F | $CH_3$ | H | H |
| I.a.14 | Cl | H | F | H | F | $CH_3$ | H | H |
| I.a.15 | CN | H | F | H | F | $CH_3$ | H | H |
| I.a.16 | F | F | F | H | F | $CH_3$ | H | H |
| I.a.17 | Cl | F | F | H | F | $CH_3$ | H | H |
| I.a.18 | F | Cl | F | H | F | $CH_3$ | H | H |
| I.a.19 | Cl | F | F | H | F | $CH_3$ | H | H |
| I.a.20 | CN | F | F | H | F | $CH_3$ | H | H |
| I.a.21 | F | CN | F | H | F | $CH_3$ | H | H |
| I.a.22 | CN | F | F | H | F | $CH_3$ | H | H |
| I.a.23 | F | F | H | F | F | $CH_3$ | H | H |
| I.a.24 | Cl | F | H | F | F | $CH_3$ | H | H |
| I.a.25 | F | Cl | H | F | F | $CH_3$ | H | H |
| I.a.26 | CN | F | H | F | F | $CH_3$ | H | H |
| I.a.27 | F | CN | H | F | F | $CH_3$ | H | H |
| I.a.28 | F | F | F | F | F | $CH_3$ | H | H |
| I.a.29 | Cl | F | F | F | F | $CH_3$ | H | H |
| I.a.30 | F | Cl | F | F | F | $CH_3$ | H | H |
| I.a.31 | CN | F | F | F | F | $CH_3$ | H | H |
| I.a.32 | F | CN | F | F | F | $CH_3$ | H | H |
| I.a.33 | H | F | F | F | F | $CH_3$ | H | H |
| I.a.34 | F | F | Br | F | F | $CH_3$ | H | H |
| I.a.35 | F | F | C≡CH | F | F | $CH_3$ | H | H |
| I.a.36 | $CF_3$ | Cl | H | H | F | $CH_3$ | H | H |
| I.a.37 | F | F | I | F | F | $CH_3$ | H | H |
| I.a.38 | F | H | H | H | F | $CH_3$ | $CH_3$ | H |
| I.a.39 | Cl | H | H | H | F | $CH_3$ | $CH_3$ | H |
| I.a.40 | Br | H | H | H | F | $CH_3$ | $CH_3$ | H |
| I.a.41 | CN | H | H | H | F | $CH_3$ | $CH_3$ | H |
| I.a.42 | $CH_3$ | H | H | H | F | $CH_3$ | $CH_3$ | H |
| I.a.43 | F | H | H | F | F | $CH_3$ | $CH_3$ | H |
| I.a.44 | Cl | H | H | F | F | $CH_3$ | $CH_3$ | H |
| I.a.45 | F | H | H | Cl | F | $CH_3$ | $CH_3$ | H |
| I.a.46 | Cl | H | H | F | F | $CH_3$ | $CH_3$ | H |
| I.a.47 | CN | H | H | F | F | $CH_3$ | $CH_3$ | H |
| I.a.48 | F | H | H | CN | F | $CH_3$ | $CH_3$ | H |
| I.a.49 | CN | H | H | F | F | $CH_3$ | $CH_3$ | H |
| I.a.50 | F | H | F | H | F | $CH_3$ | $CH_3$ | H |
| I.a.51 | Cl | H | F | H | F | $CH_3$ | $CH_3$ | H |
| I.a.52 | CN | H | F | H | F | $CH_3$ | $CH_3$ | H |
| I.a.53 | F | F | F | H | F | $CH_3$ | $CH_3$ | H |
| I.a.54 | Cl | F | F | H | F | $CH_3$ | $CH_3$ | H |
| I.a.55 | F | Cl | F | H | F | $CH_3$ | $CH_3$ | H |
| I.a.56 | Cl | F | F | H | F | $CH_3$ | $CH_3$ | H |
| I.a.57 | CN | F | F | H | F | $CH_3$ | $CH_3$ | H |
| I.a.58 | F | CN | F | H | F | $CH_3$ | $CH_3$ | H |
| I.a.59 | CN | F | F | H | F | $CH_3$ | $CH_3$ | H |
| I.a.60 | F | F | H | F | F | $CH_3$ | $CH_3$ | H |
| I.a.61 | Cl | F | H | F | F | $CH_3$ | $CH_3$ | H |
| I.a.62 | F | Cl | H | F | F | $CH_3$ | $CH_3$ | H |
| I.a.63 | CN | F | H | F | F | $CH_3$ | $CH_3$ | H |
| I.a.64 | F | CN | H | F | F | $CH_3$ | $CH_3$ | H |
| I.a.65 | F | F | F | F | F | $CH_3$ | $CH_3$ | H |
| I.a.66 | Cl | F | F | F | F | $CH_3$ | $CH_3$ | H |
| I.a.67 | F | Cl | F | F | F | $CH_3$ | $CH_3$ | H |
| I.a.68 | CN | F | F | F | F | $CH_3$ | $CH_3$ | H |
| I.a.69 | F | CN | F | F | F | $CH_3$ | $CH_3$ | H |
| I.a.70 | H | F | F | F | F | $CH_3$ | $CH_3$ | H |
| I.a.71 | F | F | Br | F | F | $CH_3$ | $CH_3$ | H |
| I.a.72 | F | F | C≡CH | F | F | $CH_3$ | $CH_3$ | H |
| I.a.73 | $CF_3$ | Cl | H | H | F | $CH_3$ | $CH_3$ | H |
| I.a.74 | F | F | I | F | F | $CH_3$ | $CH_3$ | H |
| I.a.75 | F | H | H | H | F | $CH_3$ | $CH_3$ | $CH_3$ |
| I.a.76 | Cl | H | H | H | F | $CH_3$ | $CH_3$ | $CH_3$ |
| I.a.77 | Br | H | H | H | F | $CH_3$ | $CH_3$ | $CH_3$ |
| I.a.78 | CN | H | H | H | F | $CH_3$ | $CH_3$ | $CH_3$ |
| I.a.79 | $CH_3$ | H | H | H | F | $CH_3$ | $CH_3$ | $CH_3$ |
| I.a.80 | F | H | H | F | F | $CH_3$ | $CH_3$ | $CH_3$ |
| I.a.81 | Cl | H | H | F | F | $CH_3$ | $CH_3$ | $CH_3$ |
| I.a.82 | F | H | H | Cl | F | $CH_3$ | $CH_3$ | $CH_3$ |
| I.a.83 | Cl | H | H | F | F | $CH_3$ | $CH_3$ | $CH_3$ |
| I.a.84 | CN | H | H | F | F | $CH_3$ | $CH_3$ | $CH_3$ |
| I.a.85 | F | H | H | CN | F | $CH_3$ | $CH_3$ | $CH_3$ |
| I.a.86 | CN | H | H | F | F | $CH_3$ | $CH_3$ | $CH_3$ |
| I.a.87 | F | H | F | H | F | $CH_3$ | $CH_3$ | $CH_3$ |
| I.a.88 | Cl | H | F | H | F | $CH_3$ | $CH_3$ | $CH_3$ |
| I.a.89 | CN | H | F | H | F | $CH_3$ | $CH_3$ | $CH_3$ |
| I.a.90 | F | F | F | H | F | $CH_3$ | $CH_3$ | $CH_3$ |
| I.a.91 | Cl | F | F | H | F | $CH_3$ | $CH_3$ | $CH_3$ |
| I.a.92 | F | Cl | F | H | F | $CH_3$ | $CH_3$ | $CH_3$ |
| I.a.93 | Cl | F | F | H | F | $CH_3$ | $CH_3$ | $CH_3$ |
| I.a.94 | CN | F | F | H | F | $CH_3$ | $CH_3$ | $CH_3$ |
| I.a.95 | F | CN | F | H | F | $CH_3$ | $CH_3$ | $CH_3$ |
| I.a.96 | CN | F | F | H | F | $CH_3$ | $CH_3$ | $CH_3$ |
| I.a.97 | F | F | H | F | F | $CH_3$ | $CH_3$ | $CH_3$ |
| I.a.98 | Cl | F | H | F | F | $CH_3$ | $CH_3$ | $CH_3$ |
| I.a.99 | F | Cl | H | F | F | $CH_3$ | $CH_3$ | $CH_3$ |
| I.a.100 | CN | F | H | F | F | $CH_3$ | $CH_3$ | $CH_3$ |
| I.a.101 | F | CN | H | F | F | $CH_3$ | $CH_3$ | $CH_3$ |
| I.a.102 | F | F | F | F | F | $CH_3$ | $CH_3$ | $CH_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.103 | Cl | F | F | F | F | $CH_3$ | $CH_3$ | $CH_3$ |
| I.a.104 | F | Cl | F | F | F | $CH_3$ | $CH_3$ | $CH_3$ |
| I.a.105 | CN | F | F | F | F | $CH_3$ | $CH_3$ | $CH_3$ |
| I.a.106 | F | CN | F | F | F | $CH_3$ | $CH_3$ | $CH_3$ |
| I.a.107 | H | F | F | F | F | $CH_3$ | $CH_3$ | $CH_3$ |
| I.a.108 | F | F | Br | F | F | $CH_3$ | $CH_3$ | $CH_3$ |
| I.a.109 | F | F | C≡CH | F | F | $CH_3$ | $CH_3$ | $CH_3$ |
| I.a.110 | $CF_3$ | Cl | H | H | F | $CH_3$ | $CH_3$ | $CH_3$ |
| I.a.111 | F | F | I | F | F | $CH_3$ | $CH_3$ | $CH_3$ |
| I.a.112 | F | H | H | H | F | F | F | F |
| I.a.113 | Cl | H | H | H | F | F | F | F |
| I.a.114 | Br | H | H | H | F | F | F | F |
| I.a.115 | CN | H | H | H | F | F | F | F |
| I.a.116 | $CH_3$ | H | H | H | F | F | F | F |
| I.a.117 | F | H | H | F | F | F | F | F |
| I.a.118 | Cl | H | H | F | F | F | F | F |
| I.a.119 | F | H | H | Cl | F | F | F | F |
| I.a.120 | Cl | H | H | F | F | F | F | F |
| I.a.121 | CN | H | H | F | F | F | F | F |
| I.a.122 | F | H | H | CN | F | F | F | F |
| I.a.123 | CN | H | H | F | F | F | F | F |
| I.a.124 | F | H | F | H | F | F | F | F |
| I.a.125 | Cl | H | F | H | F | F | F | F |
| I.a.126 | CN | H | F | H | F | F | F | F |
| I.a.127 | F | F | F | H | F | F | F | F |
| I.a.128 | Cl | F | F | H | F | F | F | F |
| I.a.129 | F | Cl | F | H | F | F | F | F |
| I.a.130 | Cl | F | F | H | F | F | F | F |
| I.a.131 | CN | F | F | H | F | F | F | F |
| I.a.132 | F | CN | F | H | F | F | F | F |
| I.a.133 | CN | F | F | H | F | F | F | F |
| I.a.134 | F | F | H | F | F | F | F | F |
| I.a.135 | Cl | F | H | F | F | F | F | F |
| I.a.136 | F | Cl | H | F | F | F | F | F |
| I.a.137 | CN | F | H | F | F | F | F | F |
| I.a.138 | F | CN | H | F | F | F | F | F |
| I.a.139 | F | F | F | F | F | F | F | F |
| I.a.140 | Cl | F | F | F | F | F | F | F |
| I.a.141 | F | Cl | F | F | F | F | F | F |
| I.a.142 | CN | F | F | F | F | F | F | F |
| I.a.143 | F | CN | F | F | F | F | F | F |
| I.a.144 | H | F | F | F | F | F | F | F |
| I.a.145 | F | F | Br | F | F | F | F | F |
| I.a.146 | F | F | C≡CH | F | F | F | F | F |
| I.a.147 | $CF_3$ | Cl | H | H | F | F | F | F |
| I.a.148 | F | F | I | F | F | F | F | F |
| I.a.149 | F | H | H | H | F | F | $CF_3$ | F |
| I.a.150 | Cl | H | H | H | F | F | $CF_3$ | F |
| I.a.151 | Br | H | H | H | F | F | $CF_3$ | F |
| I.a.152 | CN | H | H | H | F | F | $CF_3$ | F |
| I.a.153 | $CH_3$ | H | H | H | F | F | $CF_3$ | F |
| I.a.154 | F | H | H | F | F | F | $CF_3$ | F |
| I.a.155 | Cl | H | H | F | F | F | $CF_3$ | F |
| I.a.156 | F | H | H | Cl | F | F | $CF_3$ | F |
| I.a.157 | Cl | H | H | F | F | F | $CF_3$ | F |
| I.a.158 | CN | H | H | F | F | F | $CF_3$ | F |
| I.a.159 | F | H | H | CN | F | F | $CF_3$ | F |
| I.a.160 | CN | H | H | F | F | F | $CF_3$ | F |
| I.a.161 | F | H | F | H | F | F | $CF_3$ | F |
| I.a.162 | Cl | H | F | H | F | F | $CF_3$ | F |
| I.a.163 | CN | H | F | H | F | F | $CF_3$ | F |
| I.a.164 | F | F | F | H | F | F | $CF_3$ | F |
| I.a.165 | Cl | F | F | H | F | F | $CF_3$ | F |
| I.a.166 | F | Cl | F | H | F | F | $CF_3$ | F |
| I.a.167 | Cl | F | F | H | F | F | $CF_3$ | F |
| I.a.168 | CN | F | F | H | F | F | $CF_3$ | F |
| I.a.169 | F | CN | F | H | F | F | $CF_3$ | F |
| I.a.170 | CN | F | F | H | F | F | $CF_3$ | F |
| I.a.171 | F | F | H | F | F | F | $CF_3$ | F |
| I.a.172 | Cl | F | H | F | F | F | $CF_3$ | F |
| I.a.173 | F | Cl | H | F | F | F | $CF_3$ | F |
| I.a.174 | CN | F | H | F | F | F | $CF_3$ | F |
| I.a.175 | F | CN | H | F | F | F | $CF_3$ | F |
| I.a.176 | F | F | F | F | F | F | $CF_3$ | F |
| I.a.177 | Cl | F | F | F | F | F | $CF_3$ | F |
| I.a.178 | F | Cl | F | F | F | F | $CF_3$ | F |
| I.a.179 | CN | F | F | F | F | F | $CF_3$ | F |
| I.a.180 | F | CN | F | F | F | F | $CF_3$ | F |
| I.a.181 | H | F | F | F | F | F | $CF_3$ | F |
| I.a.182 | F | F | Br | F | F | F | $CF_3$ | F |
| I.a.183 | F | F | C≡CH | F | F | F | $CF_3$ | F |
| I.a.184 | $CF_3$ | Cl | H | H | F | F | $CF_3$ | F |
| I.a.185 | F | F | I | F | F | F | $CF_3$ | F |
| I.a.186 | F | H | H | H | F | F | $CH_3$ | F |
| I.a.187 | Cl | H | H | H | F | F | $CH_3$ | F |
| I.a.188 | Br | H | H | H | F | F | $CH_3$ | F |
| I.a.189 | CN | H | H | H | F | F | $CH_3$ | F |
| I.a.190 | $CH_3$ | H | H | H | F | F | $CH_3$ | F |
| I.a.191 | F | H | H | F | F | F | $CH_3$ | F |
| I.a.192 | Cl | H | H | F | F | F | $CH_3$ | F |
| I.a.193 | F | H | H | Cl | F | F | $CH_3$ | F |
| I.a.194 | Cl | H | H | F | F | F | $CH_3$ | F |
| I.a.195 | CN | H | H | F | F | F | $CH_3$ | F |
| I.a.196 | F | H | H | CN | F | F | $CH_3$ | F |
| I.a.197 | CN | H | H | F | F | F | $CH_3$ | F |
| I.a.198 | F | H | F | H | F | F | $CH_3$ | F |
| I.a.199 | Cl | H | F | H | F | F | $CH_3$ | F |
| I.a.200 | CN | H | F | H | F | F | $CH_3$ | F |
| I.a.201 | F | F | F | H | F | F | $CH_3$ | F |
| I.a.202 | Cl | F | F | H | F | F | $CH_3$ | F |
| I.a.203 | F | Cl | F | H | F | F | $CH_3$ | F |
| I.a.204 | Cl | F | F | H | F | F | $CH_3$ | F |
| I.a.205 | CN | F | F | H | F | F | $CH_3$ | F |
| I.a.206 | F | CN | F | H | F | F | $CH_3$ | F |
| I.a.207 | CN | F | F | H | F | F | $CH_3$ | F |
| I.a.208 | F | F | H | F | F | F | $CH_3$ | F |
| I.a.209 | Cl | F | H | F | F | F | $CH_3$ | F |
| I.a.210 | F | Cl | H | F | F | F | $CH_3$ | F |
| I.a.211 | CN | F | H | F | F | F | $CH_3$ | F |
| I.a.212 | F | CN | H | F | F | F | $CH_3$ | F |
| I.a.213 | F | F | F | F | F | F | $CH_3$ | F |
| I.a.214 | Cl | F | F | F | F | F | $CH_3$ | F |
| I.a.215 | F | Cl | F | F | F | F | $CH_3$ | F |
| I.a.216 | CN | F | F | F | F | F | $CH_3$ | F |
| I.a.217 | F | CN | F | F | F | F | $CH_3$ | F |
| I.a.218 | H | F | F | F | F | F | $CH_3$ | F |
| I.a.219 | F | F | Br | F | F | F | $CH_3$ | F |
| I.a.220 | F | F | C≡CH | F | F | F | $CH_3$ | F |
| I.a.221 | $CF_3$ | Cl | H | H | F | F | $CH_3$ | F |
| I.a.222 | F | F | I | F | F | F | $CH_3$ | F |
| I.a.223 | F | H | H | H | F | F | $CH_3$ | H |
| I.a.224 | Cl | H | H | H | F | F | $CH_3$ | H |
| I.a.225 | Br | H | H | H | F | F | $CH_3$ | H |
| I.a.226 | CN | H | H | H | F | F | $CH_3$ | H |
| I.a.227 | $CH_3$ | H | H | H | F | F | $CH_3$ | H |
| I.a.228 | F | H | H | F | F | F | $CH_3$ | H |
| I.a.229 | Cl | H | H | F | F | F | $CH_3$ | H |
| I.a.230 | F | H | H | Cl | F | F | $CH_3$ | H |
| I.a.231 | Cl | H | H | F | F | F | $CH_3$ | H |
| I.a.232 | CN | H | H | F | F | F | $CH_3$ | H |
| I.a.233 | F | H | H | CN | F | F | $CH_3$ | H |
| I.a.234 | CN | H | H | F | F | F | $CH_3$ | H |
| I.a.235 | F | H | F | H | F | F | $CH_3$ | H |
| I.a.236 | Cl | H | F | H | F | F | $CH_3$ | H |
| I.a.237 | CN | H | F | H | F | F | $CH_3$ | H |
| I.a.238 | F | F | F | H | F | F | $CH_3$ | H |
| I.a.239 | Cl | F | F | H | F | F | $CH_3$ | H |
| I.a.240 | F | Cl | F | H | F | F | $CH_3$ | H |
| I.a.241 | Cl | F | F | H | F | F | $CH_3$ | H |
| I.a.242 | CN | F | F | H | F | F | $CH_3$ | H |
| I.a.243 | F | CN | F | H | F | F | $CH_3$ | H |
| I.a.244 | CN | F | F | H | F | F | $CH_3$ | H |
| I.a.245 | F | F | H | F | F | F | $CH_3$ | H |
| I.a.246 | Cl | F | H | F | F | F | $CH_3$ | H |
| I.a.247 | F | Cl | H | F | F | F | $CH_3$ | H |
| I.a.248 | CN | F | H | F | F | F | $CH_3$ | H |
| I.a.249 | F | CN | H | F | F | F | $CH_3$ | H |
| I.a.250 | F | F | F | F | F | F | $CH_3$ | H |
| I.a.251 | Cl | F | F | F | F | F | $CH_3$ | H |
| I.a.252 | F | Cl | F | F | F | F | $CH_3$ | H |
| I.a.253 | CN | F | F | F | F | F | $CH_3$ | H |
| I.a.254 | F | CN | F | F | F | F | $CH_3$ | H |
| I.a.255 | H | F | F | F | F | F | $CH_3$ | H |
| I.a.256 | F | F | Br | F | F | F | $CH_3$ | H |
| I.a.257 | F | F | C≡CH | F | F | F | $CH_3$ | H |
| I.a.258 | $CF_3$ | Cl | H | H | F | F | $CH_3$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.259 | F | F | I | F | F | F | $CH_3$ | H |
| I.a.260 | F | H | H | H | F | F | $CH_3$ | $CH_3$ |
| I.a.261 | Cl | H | H | H | F | F | $CH_3$ | $CH_3$ |
| I.a.262 | Br | H | H | H | F | F | $CH_3$ | $CH_3$ |
| I.a.263 | CN | H | H | H | F | F | $CH_3$ | $CH_3$ |
| I.a.264 | $CH_3$ | H | H | H | F | F | $CH_3$ | $CH_3$ |
| I.a.265 | F | H | H | F | F | F | $CH_3$ | $CH_3$ |
| I.a.266 | Cl | H | H | F | F | F | $CH_3$ | $CH_3$ |
| I.a.267 | F | H | H | Cl | F | F | $CH_3$ | $CH_3$ |
| I.a.268 | Cl | H | H | F | F | F | $CH_3$ | $CH_3$ |
| I.a.269 | CN | H | H | F | F | F | $CH_3$ | $CH_3$ |
| I.a.270 | F | H | H | CN | F | F | $CH_3$ | $CH_3$ |
| I.a.271 | CN | H | H | F | F | F | $CH_3$ | $CH_3$ |
| I.a.272 | F | H | F | H | F | F | $CH_3$ | $CH_3$ |
| I.a.273 | Cl | H | F | H | F | F | $CH_3$ | $CH_3$ |
| I.a.274 | CN | H | F | H | F | F | $CH_3$ | $CH_3$ |
| I.a.275 | F | F | F | H | F | F | $CH_3$ | $CH_3$ |
| I.a.276 | Cl | F | F | H | F | F | $CH_3$ | $CH_3$ |
| I.a.277 | F | Cl | F | H | F | F | $CH_3$ | $CH_3$ |
| I.a.278 | Cl | F | F | H | F | F | $CH_3$ | $CH_3$ |
| I.a.279 | CN | F | F | H | F | F | $CH_3$ | $CH_3$ |
| I.a.280 | F | CN | F | H | F | F | $CH_3$ | $CH_3$ |
| I.a.281 | CN | F | F | H | F | F | $CH_3$ | $CH_3$ |
| I.a.282 | F | F | H | F | F | F | $CH_3$ | $CH_3$ |
| I.a.283 | Cl | F | H | F | F | F | $CH_3$ | $CH_3$ |
| I.a.284 | F | Cl | H | F | F | F | $CH_3$ | $CH_3$ |
| I.a.285 | CN | F | H | F | F | F | $CH_3$ | $CH_3$ |
| I.a.286 | F | CN | H | F | F | F | $CH_3$ | $CH_3$ |
| I.a.287 | F | F | F | F | F | F | $CH_3$ | $CH_3$ |
| I.a.288 | Cl | F | F | F | F | F | $CH_3$ | $CH_3$ |
| I.a.289 | F | Cl | F | F | F | F | $CH_3$ | $CH_3$ |
| I.a.290 | CN | F | F | F | F | F | $CH_3$ | $CH_3$ |
| I.a.291 | F | CN | F | F | F | F | $CH_3$ | $CH_3$ |
| I.a.292 | H | F | F | F | F | F | $CH_3$ | $CH_3$ |
| I.a.293 | F | F | Br | F | F | F | $CH_3$ | $CH_3$ |
| I.a.294 | F | F | C≡CH | F | F | F | $CH_3$ | $CH_3$ |
| I.a.295 | $CF_3$ | Cl | H | H | F | F | $CH_3$ | $CH_3$ |
| I.a.296 | F | F | I | F | F | F | $CH_3$ | $CH_3$ |
| I.a.297 | F | H | H | H | F | Cl | $CH_3$ | $CH_3$ |
| I.a.298 | Cl | H | H | H | F | Cl | $CH_3$ | $CH_3$ |
| I.a.299 | Br | H | H | H | F | Cl | $CH_3$ | $CH_3$ |
| I.a.300 | CN | H | H | H | F | Cl | $CH_3$ | $CH_3$ |
| I.a.301 | $CH_3$ | H | H | H | F | Cl | $CH_3$ | $CH_3$ |
| I.a.302 | F | H | H | F | F | Cl | $CH_3$ | $CH_3$ |
| I.a.303 | Cl | H | H | F | F | Cl | $CH_3$ | $CH_3$ |
| I.a.304 | F | H | H | Cl | F | Cl | $CH_3$ | $CH_3$ |
| I.a.305 | Cl | H | H | F | F | Cl | $CH_3$ | $CH_3$ |
| I.a.306 | CN | H | H | F | F | Cl | $CH_3$ | $CH_3$ |
| I.a.307 | F | H | H | CN | F | Cl | $CH_3$ | $CH_3$ |
| I.a.308 | CN | H | H | F | F | Cl | $CH_3$ | $CH_3$ |
| I.a.309 | F | H | F | H | F | Cl | $CH_3$ | $CH_3$ |
| I.a.310 | Cl | H | F | H | F | Cl | $CH_3$ | $CH_3$ |
| I.a.311 | CN | H | F | H | F | Cl | $CH_3$ | $CH_3$ |
| I.a.312 | F | F | F | H | F | Cl | $CH_3$ | $CH_3$ |
| I.a.313 | Cl | F | F | H | F | Cl | $CH_3$ | $CH_3$ |
| I.a.314 | F | Cl | F | H | F | Cl | $CH_3$ | $CH_3$ |
| I.a.315 | Cl | F | F | H | F | Cl | $CH_3$ | $CH_3$ |
| I.a.316 | CN | F | F | H | F | Cl | $CH_3$ | $CH_3$ |
| I.a.317 | F | CN | F | H | F | Cl | $CH_3$ | $CH_3$ |
| I.a.318 | CN | F | F | H | F | Cl | $CH_3$ | $CH_3$ |
| I.a.319 | F | F | H | F | F | Cl | $CH_3$ | $CH_3$ |
| I.a.320 | Cl | F | H | F | F | Cl | $CH_3$ | $CH_3$ |
| I.a.321 | F | Cl | H | F | F | Cl | $CH_3$ | $CH_3$ |
| I.a.322 | CN | F | H | F | F | Cl | $CH_3$ | $CH_3$ |
| I.a.323 | F | CN | H | F | F | Cl | $CH_3$ | $CH_3$ |
| I.a.324 | F | F | F | F | F | Cl | $CH_3$ | $CH_3$ |
| I.a.325 | Cl | F | F | F | F | Cl | $CH_3$ | $CH_3$ |
| I.a.326 | F | Cl | F | F | F | Cl | $CH_3$ | $CH_3$ |
| I.a.327 | CN | F | F | F | F | Cl | $CH_3$ | $CH_3$ |
| I.a.328 | F | CN | F | F | F | Cl | $CH_3$ | $CH_3$ |
| I.a.329 | H | F | F | F | F | Cl | $CH_3$ | $CH_3$ |
| I.a.330 | F | F | Br | F | F | Cl | $CH_3$ | $CH_3$ |
| I.a.331 | F | F | C≡CH | F | F | Cl | $CH_3$ | $CH_3$ |
| I.a.332 | $CF_3$ | Cl | H | H | F | Cl | $CH_3$ | $CH_3$ |
| I.a.333 | F | F | I | F | F | Cl | $CH_3$ | $CH_3$ |
| I.a.334 | F | H | H | H | F | F | $C_2H_5$ | $CH_3$ |
| I.a.335 | Cl | H | H | H | F | F | $C_2H_5$ | $CH_3$ |
| I.a.336 | Br | H | H | H | F | F | $C_2H_5$ | $CH_3$ |
| I.a.337 | CN | H | H | H | F | F | $C_2H_5$ | $CH_3$ |
| I.a.338 | $CH_3$ | H | H | H | F | F | $C_2H_5$ | $CH_3$ |
| I.a.339 | F | H | H | F | F | F | $C_2H_5$ | $CH_3$ |
| I.a.340 | Cl | H | H | F | F | F | $C_2H_5$ | $CH_3$ |
| I.a.341 | F | H | H | Cl | F | F | $C_2H_5$ | $CH_3$ |
| I.a.342 | Cl | H | H | F | F | F | $C_2H_5$ | $CH_3$ |
| I.a.343 | CN | H | H | F | F | F | $C_2H_5$ | $CH_3$ |
| I.a.344 | F | H | H | CN | F | F | $C_2H_5$ | $CH_3$ |
| I.a.345 | CN | H | H | F | F | F | $C_2H_5$ | $CH_3$ |
| I.a.346 | F | H | F | H | F | F | $C_2H_5$ | $CH_3$ |
| I.a.347 | Cl | H | F | H | F | F | $C_2H_5$ | $CH_3$ |
| I.a.348 | CN | H | F | H | F | F | $C_2H_5$ | $CH_3$ |
| I.a.349 | F | F | F | H | F | F | $C_2H_5$ | $CH_3$ |
| I.a.350 | Cl | F | F | H | F | F | $C_2H_5$ | $CH_3$ |
| I.a.351 | F | Cl | F | H | F | F | $C_2H_5$ | $CH_3$ |
| I.a.352 | Cl | F | F | H | F | F | $C_2H_5$ | $CH_3$ |
| I.a.353 | CN | F | F | H | F | F | $C_2H_5$ | $CH_3$ |
| I.a.354 | F | CN | F | H | F | F | $C_2H_5$ | $CH_3$ |
| I.a.355 | CN | F | F | H | F | F | $C_2H_5$ | $CH_3$ |
| I.a.356 | F | F | H | F | F | F | $C_2H_5$ | $CH_3$ |
| I.a.357 | Cl | F | H | F | F | F | $C_2H_5$ | $CH_3$ |
| I.a.358 | F | Cl | H | F | F | F | $C_2H_5$ | $CH_3$ |
| I.a.359 | CN | F | H | F | F | F | $C_2H_5$ | $CH_3$ |
| I.a.360 | F | CN | H | F | F | F | $C_2H_5$ | $CH_3$ |
| I.a.361 | F | F | F | F | F | F | $C_2H_5$ | $CH_3$ |
| I.a.362 | Cl | F | F | F | F | F | $C_2H_5$ | $CH_3$ |
| I.a.363 | F | Cl | F | F | F | F | $C_2H_5$ | $CH_3$ |
| I.a.364 | CN | F | F | F | F | F | $C_2H_5$ | $CH_3$ |
| I.a.365 | F | CN | F | F | F | F | $C_2H_5$ | $CH_3$ |
| I.a.366 | H | F | F | F | F | F | $C_2H_5$ | $CH_3$ |
| I.a.367 | F | F | Br | F | F | F | $C_2H_5$ | $CH_3$ |
| I.a.368 | F | F | C≡CH | F | F | F | $C_2H_5$ | $CH_3$ |
| I.a.369 | $CF_3$ | Cl | H | H | F | F | $C_2H_5$ | $CH_3$ |
| I.a.370 | F | F | I | F | F | F | $C_2H_5$ | $CH_3$ |
| I.a.371 | F | H | H | H | F | F | $C_2H_5$ | $C_2H_5$ |
| I.a.372 | Cl | H | H | H | F | F | $C_2H_5$ | $C_2H_5$ |
| I.a.373 | Br | H | H | H | F | F | $C_2H_5$ | $C_2H_5$ |
| I.a.374 | CN | H | H | H | F | F | $C_2H_5$ | $C_2H_5$ |
| I.a.375 | $CH_3$ | H | H | H | F | F | $C_2H_5$ | $C_2H_5$ |
| I.a.376 | F | H | H | F | F | F | $C_2H_5$ | $C_2H_5$ |
| I.a.377 | Cl | H | H | F | F | F | $C_2H_5$ | $C_2H_5$ |
| I.a.378 | F | H | H | Cl | F | F | $C_2H_5$ | $C_2H_5$ |
| I.a.379 | Cl | H | H | F | F | F | $C_2H_5$ | $C_2H_5$ |
| I.a.380 | CN | H | H | F | F | F | $C_2H_5$ | $C_2H_5$ |
| I.a.381 | F | H | H | CN | F | F | $C_2H_5$ | $C_2H_5$ |
| I.a.382 | CN | H | H | F | F | F | $C_2H_5$ | $C_2H_5$ |
| I.a.383 | F | H | F | H | F | F | $C_2H_5$ | $C_2H_5$ |
| I.a.384 | Cl | H | F | H | F | F | $C_2H_5$ | $C_2H_5$ |
| I.a.385 | CN | H | F | H | F | F | $C_2H_5$ | $C_2H_5$ |
| I.a.386 | F | F | F | H | F | F | $C_2H_5$ | $C_2H_5$ |
| I.a.387 | Cl | F | F | H | F | F | $C_2H_5$ | $C_2H_5$ |
| I.a.388 | F | Cl | F | H | F | F | $C_2H_5$ | $C_2H_5$ |
| I.a.389 | Cl | F | F | H | F | F | $C_2H_5$ | $C_2H_5$ |
| I.a.390 | CN | F | F | H | F | F | $C_2H_5$ | $C_2H_5$ |
| I.a.391 | F | CN | F | H | F | F | $C_2H_5$ | $C_2H_5$ |
| I.a.392 | CN | F | F | H | F | F | $C_2H_5$ | $C_2H_5$ |
| I.a.393 | F | F | H | F | F | F | $C_2H_5$ | $C_2H_5$ |
| I.a.394 | Cl | F | H | F | F | F | $C_2H_5$ | $C_2H_5$ |
| I.a.395 | F | Cl | H | F | F | F | $C_2H_5$ | $C_2H_5$ |
| I.a.396 | CN | F | H | F | F | F | $C_2H_5$ | $C_2H_5$ |
| I.a.397 | F | CN | H | F | F | F | $C_2H_5$ | $C_2H_5$ |
| I.a.398 | F | F | F | F | F | F | $C_2H_5$ | $C_2H_5$ |
| I.a.399 | Cl | F | F | F | F | F | $C_2H_5$ | $C_2H_5$ |
| I.a.400 | F | Cl | F | F | F | F | $C_2H_5$ | $C_2H_5$ |
| I.a.401 | CN | F | F | F | F | F | $C_2H_5$ | $C_2H_5$ |
| I.a.402 | F | CN | F | F | F | F | $C_2H_5$ | $C_2H_5$ |
| I.a.403 | H | F | F | F | F | F | $C_2H_5$ | $C_2H_5$ |
| I.a.404 | F | F | Br | F | F | F | $C_2H_5$ | $C_2H_5$ |
| I.a.405 | F | F | C≡CH | F | F | F | $C_2H_5$ | $C_2H_5$ |
| I.a.406 | $CF_3$ | Cl | H | H | F | F | $C_2H_5$ | $C_2H_5$ |
| I.a.407 | F | F | I | F | F | F | $C_2H_5$ | $C_2H_5$ |
| I.a.408 | F | H | H | H | F | H | —$(CH_2)_2$— | |
| I.a.409 | Cl | H | H | H | F | H | —$(CH_2)_2$— | |
| I.a.410 | Br | H | H | H | F | H | —$(CH_2)_2$— | |
| I.a.411 | CN | H | H | H | F | H | —$(CH_2)_2$— | |
| I.a.412 | $CH_3$ | H | H | H | F | H | —$(CH_2)_2$— | |
| I.a.413 | F | H | H | F | F | H | —$(CH_2)_2$— | |
| I.a.414 | Cl | H | H | F | F | H | —$(CH_2)_2$— | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.415 | F | H | H | Cl | F | H | —$(CH_2)_2$— | |
| I.a.416 | Cl | H | H | F | F | H | —$(CH_2)_2$— | |
| I.a.417 | CN | H | H | F | F | H | —$(CH_2)_2$— | |
| I.a.418 | F | H | H | CN | F | H | —$(CH_2)_2$— | |
| I.a.419 | CN | H | H | F | F | H | —$(CH_2)_2$— | |
| I.a.420 | F | H | F | H | F | H | —$(CH_2)_2$— | |
| I.a.421 | Cl | H | F | H | F | H | —$(CH_2)_2$— | |
| I.a.422 | CN | H | F | H | F | H | —$(CH_2)_2$— | |
| I.a.423 | F | F | H | H | F | H | —$(CH_2)_2$— | |
| I.a.424 | Cl | F | H | H | F | H | —$(CH_2)_2$— | |
| I.a.425 | F | Cl | H | H | F | H | —$(CH_2)_2$— | |
| I.a.426 | Cl | F | F | H | F | H | —$(CH_2)_2$— | |
| I.a.427 | CN | F | F | H | F | H | —$(CH_2)_2$— | |
| I.a.428 | F | CN | F | H | F | H | —$(CH_2)_2$— | |
| I.a.429 | CN | F | F | H | F | H | —$(CH_2)_2$— | |
| I.a.430 | F | F | H | F | F | H | —$(CH_2)_2$— | |
| I.a.431 | Cl | F | H | F | F | H | —$(CH_2)_2$— | |
| I.a.432 | F | Cl | H | F | F | H | —$(CH_2)_2$— | |
| I.a.433 | CN | F | H | F | F | H | —$(CH_2)_2$— | |
| I.a.434 | F | CN | H | F | F | H | —$(CH_2)_2$— | |
| I.a.435 | F | F | F | F | F | H | —$(CH_2)_2$— | |
| I.a.436 | Cl | F | F | F | F | H | —$(CH_2)_2$— | |
| I.a.437 | F | Cl | F | F | F | H | —$(CH_2)_2$— | |
| I.a.438 | CN | F | F | F | F | H | —$(CH_2)_2$— | |
| I.a.439 | F | CN | F | F | F | H | —$(CH_2)_2$— | |
| I.a.440 | H | F | F | F | F | H | —$(CH_2)_2$— | |
| I.a.441 | F | F | Br | F | F | H | —$(CH_2)_2$— | |
| I.a.442 | F | F | C≡CH | F | F | H | —$(CH_2)_2$— | |
| I.a.443 | $CF_3$ | Cl | H | H | F | H | —$(CH_2)_2$— | |
| I.a.444 | F | F | I | F | F | H | —$(CH_2)_2$— | |
| I.a.445 | F | H | H | H | F | H | —$(CH_2)_3$— | |
| I.a.446 | Cl | H | H | H | F | H | —$(CH_2)_3$— | |
| I.a.447 | Br | H | H | H | F | H | —$(CH_2)_3$— | |
| I.a.448 | CN | H | H | H | F | H | —$(CH_2)_3$— | |
| I.a.449 | $CH_3$ | H | H | H | F | H | —$(CH_2)_3$— | |
| I.a.450 | F | H | H | F | F | H | —$(CH_2)_3$— | |
| I.a.451 | Cl | H | H | F | F | H | —$(CH_2)_3$— | |
| I.a.452 | F | H | H | Cl | F | H | —$(CH_2)_3$— | |
| I.a.453 | Cl | H | H | F | F | H | —$(CH_2)_3$— | |
| I.a.454 | CN | H | H | F | F | H | —$(CH_2)_3$— | |
| I.a.455 | F | H | H | CN | F | H | —$(CH_2)_3$— | |
| I.a.456 | CN | H | H | F | F | H | —$(CH_2)_3$— | |
| I.a.457 | F | H | F | H | F | H | —$(CH_2)_3$— | |
| I.a.458 | Cl | H | F | H | F | H | —$(CH_2)_3$— | |
| I.a.459 | CN | H | F | H | F | H | —$(CH_2)_3$— | |
| I.a.460 | F | F | F | H | F | H | —$(CH_2)_3$— | |
| I.a.461 | Cl | F | F | H | F | H | —$(CH_2)_3$— | |
| I.a.462 | F | Cl | F | H | F | H | —$(CH_2)_3$— | |
| I.a.463 | Cl | F | F | H | F | H | —$(CH_2)_3$— | |
| I.a.464 | CN | F | F | H | F | H | —$(CH_2)_3$— | |
| I.a.465 | F | CN | F | H | F | H | —$(CH_2)_3$— | |
| I.a.466 | CN | F | F | H | F | H | —$(CH_2)_3$— | |
| I.a.467 | F | F | H | F | F | H | —$(CH_2)_3$— | |
| I.a.468 | Cl | F | H | F | F | H | —$(CH_2)_3$— | |
| I.a.469 | F | Cl | H | F | F | H | —$(CH_2)_3$— | |
| I.a.470 | CN | F | H | F | F | H | —$(CH_2)_3$— | |
| I.a.471 | F | CN | H | F | F | H | —$(CH_2)_3$— | |
| I.a.472 | F | F | F | F | F | H | —$(CH_2)_3$— | |
| I.a.473 | Cl | F | F | F | F | H | —$(CH_2)_3$— | |
| I.a.474 | F | Cl | F | F | F | H | —$(CH_2)_3$— | |
| I.a.475 | CN | F | F | F | F | H | —$(CH_2)_3$— | |
| I.a.476 | F | CN | F | F | F | H | —$(CH_2)_3$— | |
| I.a.477 | H | F | F | F | F | H | —$(CH_2)_3$— | |
| I.a.478 | F | F | Br | F | F | H | —$(CH_2)_3$— | |
| I.a.479 | F | F | C≡CH | F | F | H | —$(CH_2)_3$— | |
| I.a.480 | $CF_3$ | Cl | H | H | F | H | —$(CH_2)_3$— | |
| I.a.481 | F | F | I | F | F | H | —$(CH_2)_3$— | |
| I.a.482 | F | H | H | H | F | H | —$(CH_2)_4$— | |
| I.a.483 | Cl | H | H | H | F | H | —$(CH_2)_4$— | |
| I.a.484 | Br | H | H | H | F | H | —$(CH_2)_4$— | |
| I.a.485 | CN | H | H | H | F | H | —$(CH_2)_4$— | |
| I.a.486 | $CH_3$ | H | H | H | F | H | —$(CH_2)_4$— | |
| I.a.487 | F | H | H | F | F | H | —$(CH_2)_4$— | |
| I.a.488 | Cl | H | H | F | F | H | —$(CH_2)_4$— | |
| I.a.489 | F | H | H | Cl | F | H | —$(CH_2)_4$— | |
| I.a.490 | Cl | H | H | F | F | H | —$(CH_2)_4$— | |
| I.a.491 | CN | H | H | F | F | H | —$(CH_2)_4$— | |
| I.a.492 | F | H | H | CN | F | H | —$(CH_2)_4$— | |
| I.a.493 | CN | H | H | F | F | H | —$(CH_2)_4$— | |
| I.a.494 | F | H | F | H | F | H | —$(CH_2)_4$— | |
| I.a.495 | Cl | H | F | H | F | H | —$(CH_2)_4$— | |
| I.a.496 | CN | H | F | H | F | H | —$(CH_2)_4$— | |
| I.a.497 | F | F | F | H | F | H | —$(CH_2)_4$— | |
| I.a.498 | Cl | F | F | H | F | H | —$(CH_2)_4$— | |
| I.a.499 | F | Cl | F | H | F | H | —$(CH_2)_4$— | |
| I.a.500 | Cl | F | F | H | F | H | —$(CH_2)_4$— | |
| I.a.501 | CN | F | F | H | F | H | —$(CH_2)_4$— | |
| I.a.502 | F | CN | F | H | F | H | —$(CH_2)_4$— | |
| I.a.503 | CN | F | F | H | F | H | —$(CH_2)_4$— | |
| I.a.504 | F | F | H | F | F | H | —$(CH_2)_4$— | |
| I.a.505 | Cl | F | H | F | F | H | —$(CH_2)_4$— | |
| I.a.506 | F | Cl | H | F | F | H | —$(CH_2)_4$— | |
| I.a.507 | CN | F | H | F | F | H | —$(CH_2)_4$— | |
| I.a.508 | F | CN | H | F | F | H | —$(CH_2)_4$— | |
| I.a.509 | F | F | F | F | F | H | —$(CH_2)_4$— | |
| I.a.510 | Cl | F | F | F | F | H | —$(CH_2)_4$— | |
| I.a.511 | F | Cl | F | F | F | H | —$(CH_2)_4$— | |
| I.a.512 | CN | F | F | F | F | H | —$(CH_2)_4$— | |
| I.a.513 | F | CN | F | F | F | H | —$(CH_2)_4$— | |
| I.a.514 | H | F | F | F | F | H | —$(CH_2)_4$— | |
| I.a.515 | F | F | Br | F | F | H | —$(CH_2)_4$— | |
| I.a.516 | F | F | C≡CH | F | F | H | —$(CH_2)_4$— | |
| I.a.517 | $CF_3$ | Cl | H | H | F | H | —$(CH_2)_4$— | |
| I.a.518 | F | F | I | F | F | H | —$(CH_2)_4$— | |
| I.a.519 | F | H | H | H | F | H | —$(CH_2)_5$— | |
| I.a.520 | Cl | H | H | H | F | H | —$(CH_2)_5$— | |
| I.a.521 | Br | H | H | H | F | H | —$(CH_2)_5$— | |
| I.a.522 | CN | H | H | H | F | H | —$(CH_2)_5$— | |
| I.a.523 | $CH_3$ | H | H | H | F | H | —$(CH_2)_5$— | |
| I.a.524 | F | H | H | F | F | H | —$(CH_2)_5$— | |
| I.a.525 | Cl | H | H | F | F | H | —$(CH_2)_5$— | |
| I.a.526 | F | H | H | Cl | F | H | —$(CH_2)_5$— | |
| I.a.527 | Cl | H | H | F | F | H | —$(CH_2)_5$— | |
| I.a.528 | CN | H | H | F | F | H | —$(CH_2)_5$— | |
| I.a.529 | F | H | H | CN | F | H | —$(CH_2)_5$— | |
| I.a.530 | CN | H | H | F | F | H | —$(CH_2)_5$— | |
| I.a.531 | F | H | F | H | F | H | —$(CH_2)_5$— | |
| I.a.532 | Cl | H | F | H | F | H | —$(CH_2)_5$— | |
| I.a.533 | CN | H | F | H | F | H | —$(CH_2)_5$— | |
| I.a.534 | F | F | F | H | F | H | —$(CH_2)_5$— | |
| I.a.535 | Cl | F | F | H | F | H | —$(CH_2)_5$— | |
| I.a.536 | F | Cl | F | H | F | H | —$(CH_2)_5$— | |
| I.a.537 | Cl | F | F | H | F | H | —$(CH_2)_5$— | |
| I.a.538 | CN | F | F | H | F | H | —$(CH_2)_5$— | |
| I.a.539 | F | CN | F | H | F | H | —$(CH_2)_5$— | |
| I.a.540 | CN | F | F | H | F | H | —$(CH_2)_5$— | |
| I.a.541 | F | F | H | F | F | H | —$(CH_2)_5$— | |
| I.a.542 | Cl | F | H | F | F | H | —$(CH_2)_5$— | |
| I.a.543 | F | Cl | H | F | F | H | —$(CH_2)_5$— | |
| I.a.544 | CN | F | H | F | F | H | —$(CH_2)_5$— | |
| I.a.545 | F | CN | H | F | F | H | —$(CH_2)_5$— | |
| I.a.546 | F | F | F | F | F | H | —$(CH_2)_5$— | |
| I.a.547 | Cl | F | F | F | F | H | —$(CH_2)_5$— | |
| I.a.548 | F | Cl | F | F | F | H | —$(CH_2)_5$— | |
| I.a.549 | CN | F | F | F | F | H | —$(CH_2)_5$— | |
| I.a.550 | F | CN | F | F | F | H | —$(CH_2)_5$— | |
| I.a.551 | H | F | F | F | F | H | —$(CH_2)_5$— | |
| I.a.552 | F | F | Br | F | F | H | —$(CH_2)_5$— | |
| I.a.553 | F | F | C≡CH | F | F | H | —$(CH_2)_5$— | |
| I.a.554 | $CF_3$ | Cl | H | H | F | H | —$(CH_2)_5$— | |
| I.a.555 | F | F | I | F | F | H | —$(CH_2)_5$— | |
| I.a.556 | F | H | H | H | F | $CH_3$ | —$(CH_2)_2$— | |
| I.a.557 | Cl | H | H | H | F | $CH_3$ | —$(CH_2)_2$— | |
| I.a.558 | Br | H | H | H | F | $CH_3$ | —$(CH_2)_2$— | |
| I.a.559 | CN | H | H | H | F | $CH_3$ | —$(CH_2)_2$— | |
| I.a.560 | $CH_3$ | H | H | H | F | $CH_3$ | —$(CH_2)_2$— | |
| I.a.561 | F | H | H | F | F | $CH_3$ | —$(CH_2)_2$— | |
| I.a.562 | Cl | H | H | F | F | $CH_3$ | —$(CH_2)_2$— | |
| I.a.563 | F | H | H | Cl | F | $CH_3$ | —$(CH_2)_2$— | |
| I.a.564 | Cl | H | H | F | F | $CH_3$ | —$(CH_2)_2$— | |
| I.a.565 | CN | H | H | F | F | $CH_3$ | —$(CH_2)_2$— | |
| I.a.566 | F | H | H | CN | F | $CH_3$ | —$(CH_2)_2$— | |
| I.a.567 | CN | H | H | F | F | $CH_3$ | —$(CH_2)_2$— | |
| I.a.566 | F | H | F | H | F | $CH_3$ | —$(CH_2)_2$— | |
| I.a.569 | Cl | H | F | H | F | $CH_3$ | —$(CH_2)_2$— | |
| I.a.570 | CN | H | F | H | F | $CH_3$ | —$(CH_2)_2$— | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.571 | F | F | F | H | F | CH₃ | | —(CH₂)₂— |
| I.a.572 | Cl | F | F | H | F | CH₃ | | —(CH₂)₂— |
| I.a.573 | F | Cl | F | H | F | CH₃ | | —(CH₂)₂— |
| I.a.574 | Cl | F | F | H | F | CH₃ | | —(CH₂)₂— |
| I.a.575 | CN | F | F | H | F | CH₃ | | —(CH₂)₂— |
| I.a.576 | F | CN | F | H | F | CH₃ | | —(CH₂)₂— |
| I.a.577 | CN | F | F | H | F | CH₃ | | —(CH₂)₂— |
| I.a.578 | F | F | H | F | F | CH₃ | | —(CH₂)₂— |
| I.a.579 | Cl | F | H | F | F | CH₃ | | —(CH₂)₂— |
| I.a.580 | F | Cl | H | F | F | CH₃ | | —(CH₂)₂— |
| I.a.581 | CN | F | H | F | F | CH₃ | | —(CH₂)₂— |
| I.a.582 | F | CN | H | F | F | CH₃ | | —(CH₂)₂— |
| I.a.583 | F | F | F | F | F | CH₃ | | —(CH₂)₂— |
| I.a.584 | Cl | F | F | F | F | CH₃ | | —(CH₂)₂— |
| I.a.585 | F | Cl | F | F | F | CH₃ | | —(CH₂)₂— |
| I.a.586 | CN | F | F | F | F | CH₃ | | —(CH₂)₂— |
| I.a.587 | F | CN | F | F | F | CH₃ | | —(CH₂)₂— |
| I.a.588 | H | F | F | F | F | CH₃ | | —(CH₂)₂— |
| I.a.589 | F | F | Br | F | F | CH₃ | | —(CH₂)₂— |
| I.a.590 | F | F | C≡CH | F | F | CH₃ | | —(CH₂)₂— |
| I.a.591 | CF₃ | Cl | H | H | F | CH₃ | | —(CH₂)₂— |
| I.a.592 | F | F | I | F | F | CH₃ | | —(CH₂)₂— |
| I.a.593 | F | H | H | H | F | CH₃ | | —(CH₂)₃— |
| I.a.594 | Cl | H | H | H | F | CH₃ | | —(CH₂)₃— |
| I.a.595 | Br | H | H | H | F | CH₃ | | —(CH₂)₃— |
| I.a.596 | CN | H | H | H | F | CH₃ | | —(CH₂)₃— |
| I.a.597 | CH₃ | H | H | H | F | CH₃ | | —(CH₂)₃— |
| I.a.598 | F | H | H | F | F | CH₃ | | —(CH₂)₃— |
| I.a.599 | Cl | H | H | F | F | CH₃ | | —(CH₂)₃— |
| I.a.600 | F | H | H | Cl | F | CH₃ | | —(CH₂)₃— |
| I.a.601 | Cl | H | H | F | F | CH₃ | | —(CH₂)₃— |
| I.a.602 | CN | H | H | F | F | CH₃ | | —(CH₂)₃— |
| I.a.603 | F | H | H | CN | F | CH₃ | | —(CH₂)₃— |
| I.a.604 | CN | H | H | F | F | CH₃ | | —(CH₂)₃— |
| I.a.605 | F | H | F | H | F | CH₃ | | —(CH₂)₃— |
| I.a.606 | Cl | H | F | H | F | CH₃ | | —(CH₂)₃— |
| I.a.607 | CN | H | F | H | F | CH₃ | | —(CH₂)₃— |
| I.a.608 | F | F | F | H | F | CH₃ | | —(CH₂)₃— |
| I.a.609 | Cl | F | F | H | F | CH₃ | | —(CH₂)₃— |
| I.a.610 | F | Cl | F | H | F | CH₃ | | —(CH₂)₃— |
| I.a.611 | Cl | F | F | H | F | CH₃ | | —(CH₂)₃— |
| I.a.612 | CN | F | F | H | F | CH₃ | | —(CH₂)₃— |
| I.a.613 | F | CN | F | H | F | CH₃ | | —(CH₂)₃— |
| I.a.614 | CN | F | F | H | F | CH₃ | | —(CH₂)₃— |
| I.a.615 | F | F | H | F | F | CH₃ | | —(CH₂)₃— |
| I.a.616 | Cl | F | H | F | F | CH₃ | | —(CH₂)₃— |
| I.a.617 | F | Cl | H | F | F | CH₃ | | —(CH₂)₃— |
| I.a.618 | CN | F | H | F | F | CH₃ | | —(CH₂)₃— |
| I.a.619 | F | CN | H | F | F | CH₃ | | —(CH₂)₃— |
| I.a.620 | F | F | F | F | F | CH₃ | | —(CH₂)₃— |
| I.a.621 | Cl | F | F | F | F | CH₃ | | —(CH₂)₃— |
| I.a.622 | F | Cl | F | F | F | CH₃ | | —(CH₂)₃— |
| I.a.623 | CN | F | F | F | F | CH₃ | | —(CH₂)₃— |
| I.a.624 | F | CN | F | F | F | CH₃ | | —(CH₂)₃— |
| I.a.625 | H | F | F | F | F | CH₃ | | —(CH₂)₃— |
| I.a.626 | F | F | Br | F | F | CH₃ | | —(CH₂)₃— |
| I.a.627 | F | F | C≡CH | F | F | CH₃ | | —(CH₂)₃— |
| I.a.628 | CF₃ | Cl | H | H | F | CH₃ | | —(CH₂)₃— |
| I.a.629 | F | F | I | F | F | CH₃ | | —(CH₂)₃— |
| I.a.630 | F | H | H | H | F | CH₃ | | —(CH₂)₄— |
| I.a.631 | Cl | H | H | H | F | CH₃ | | —(CH₂)₄— |
| I.a.632 | Br | H | H | H | F | CH₃ | | —(CH₂)₄— |
| I.a.633 | CN | H | H | H | F | CH₃ | | —(CH₂)₄— |
| I.a.634 | CH₃ | H | H | H | F | CH₃ | | —(CH₂)₄— |
| I.a.635 | F | H | H | F | F | CH₃ | | —(CH₂)₄— |
| I.a.636 | Cl | H | H | F | F | CH₃ | | —(CH₂)₄— |
| I.a.637 | F | H | H | Cl | F | CH₃ | | —(CH₂)₄— |
| I.a.638 | Cl | H | H | F | F | CH₃ | | —(CH₂)₄— |
| I.a.639 | CN | H | H | F | F | CH₃ | | —(CH₂)₄— |
| I.a.640 | F | H | H | CN | F | CH₃ | | —(CH₂)₄— |
| I.a.641 | CN | H | H | F | F | CH₃ | | —(CH₂)₄— |
| I.a.642 | F | H | F | H | F | CH₃ | | —(CH₂)₄— |
| I.a.643 | Cl | H | F | H | F | CH₃ | | —(CH₂)₄— |
| I.a.644 | CN | H | F | H | F | CH₃ | | —(CH₂)₄— |
| I.a.645 | F | F | F | H | F | CH₃ | | —(CH₂)₄— |
| I.a.646 | Cl | F | F | H | F | CH₃ | | —(CH₂)₄— |
| I.a.647 | F | Cl | F | H | F | CH₃ | | —(CH₂)₄— |
| I.a.648 | Cl | F | F | H | F | CH₃ | | —(CH₂)₄— |
| I.a.649 | CN | F | F | H | F | CH₃ | | —(CH₂)₄— |
| I.a.650 | F | CN | F | H | F | CH₃ | | —(CH₂)₄— |
| I.a.651 | CN | F | F | H | F | CH₃ | | —(CH₂)₄— |
| I.a.652 | F | F | H | F | F | CH₃ | | —(CH₂)₄— |
| I.a.653 | Cl | F | H | F | F | CH₃ | | —(CH₂)₄— |
| I.a.654 | F | Cl | H | F | F | CH₃ | | —(CH₂)₄— |
| I.a.655 | CN | F | H | F | F | CH₃ | | —(CH₂)₄— |
| I.a.656 | F | CN | H | F | F | CH₃ | | —(CH₂)₄— |
| I.a.657 | F | F | F | F | F | CH₃ | | —(CH₂)₄— |
| I.a.658 | Cl | F | F | F | F | CH₃ | | —(CH₂)₄— |
| I.a.659 | F | Cl | F | F | F | CH₃ | | —(CH₂)₄— |
| I.a.660 | CN | F | F | F | F | CH₃ | | —(CH₂)₄— |
| I.a.661 | F | CN | F | F | F | CH₃ | | —(CH₂)₄— |
| I.a.662 | H | F | F | F | F | CH₃ | | —(CH₂)₄— |
| I.a.663 | F | F | Br | F | F | CH₃ | | —(CH₂)₄— |
| I.a.664 | F | F | C≡CH | F | F | CH₃ | | —(CH₂)₄— |
| I.a.665 | CF₃ | Cl | H | H | F | CH₃ | | —(CH₂)₄— |
| I.a.666 | F | F | I | F | F | CH₃ | | —(CH₂)₄— |
| I.a.667 | F | H | H | H | F | CH₃ | | —(CH₂)₅— |
| I.a.668 | Cl | H | H | H | F | CH₃ | | —(CH₂)₅— |
| I.a.669 | Br | H | H | H | F | CH₃ | | —(CH₂)₅— |
| I.a.670 | CN | H | H | H | F | CH₃ | | —(CH₂)₅— |
| I.a.671 | CH₃ | H | H | H | F | CH₃ | | —(CH₂)₅— |
| I.a.672 | F | H | H | F | F | CH₃ | | —(CH₂)₅— |
| I.a.673 | Cl | H | H | F | F | CH₃ | | —(CH₂)₅— |
| I.a.674 | F | H | H | Cl | F | CH₃ | | —(CH₂)₅— |
| I.a.675 | Cl | H | H | F | F | CH₃ | | —(CH₂)₅— |
| I.a.676 | CN | H | H | F | F | CH₃ | | —(CH₂)₅— |
| I.a.677 | F | H | H | CN | F | CH₃ | | —(CH₂)₅— |
| I.a.678 | CN | H | H | F | F | CH₃ | | —(CH₂)₅— |
| I.a.679 | F | H | F | H | F | CH₃ | | —(CH₂)₅— |
| I.a.680 | Cl | H | F | H | F | CH₃ | | —(CH₂)₅— |
| I.a.681 | CN | H | F | H | F | CH₃ | | —(CH₂)₅— |
| I.a.682 | F | F | F | H | F | CH₃ | | —(CH₂)₅— |
| I.a.683 | Cl | F | F | H | F | CH₃ | | —(CH₂)₅— |
| I.a.684 | F | Cl | F | H | F | CH₃ | | —(CH₂)₅— |
| I.a.685 | Cl | F | F | H | F | CH₃ | | —(CH₂)₅— |
| I.a.686 | CN | F | F | H | F | CH₃ | | —(CH₂)₅— |
| I.a.687 | F | CN | F | H | F | CH₃ | | —(CH₂)₅— |
| I.a.688 | CN | F | F | H | F | CH₃ | | —(CH₂)₅— |
| I.a.689 | F | F | H | F | F | CH₃ | | —(CH₂)₅— |
| I.a.690 | Cl | F | H | F | F | CH₃ | | —(CH₂)₅— |
| I.a.691 | F | Cl | H | F | F | CH₃ | | —(CH₂)₅— |
| I.a.692 | CN | F | H | F | F | CH₃ | | —(CH₂)₅— |
| I.a.693 | F | CN | H | F | F | CH₃ | | —(CH₂)₅— |
| I.a.694 | F | F | F | F | F | CH₃ | | —(CH₂)₅— |
| I.a.695 | Cl | F | F | F | F | CH₃ | | —(CH₂)₅— |
| I.a.696 | F | Cl | F | F | F | CH₃ | | —(CH₂)₅— |
| I.a.697 | CN | F | F | F | F | CH₃ | | —(CH₂)₅— |
| I.a.698 | F | CN | F | F | F | CH₃ | | —(CH₂)₅— |
| I.a.699 | H | F | F | F | F | CH₃ | | —(CH₂)₅— |
| I.a.700 | F | F | Br | F | F | CH₃ | | —(CH₂)₅— |
| I.a.701 | F | F | C≡CH | F | F | CH₃ | | —(CH₂)₅— |
| I.a.702 | CF₃ | Cl | H | H | F | CH₃ | | —(CH₂)₅— |
| I.a.703 | F | F | I | F | F | CH₃ | | —(CH₂)₅— |
| I.a.704 | F | H | H | H | F | F | | —(CH₂)₂— |
| I.a.705 | Cl | H | H | H | F | F | | —(CH₂)₂— |
| I.a.706 | Br | H | H | H | F | F | | —(CH₂)₂— |
| I.a.707 | CN | H | H | H | F | F | | —(CH₂)₂— |
| I.a.708 | CH₃ | H | H | H | F | F | | —(CH₂)₂— |
| I.a.709 | F | H | H | F | F | F | | —(CH₂)₂— |
| I.a.710 | Cl | H | H | F | F | F | | —(CH₂)₂— |
| I.a.711 | F | H | H | Cl | F | F | | —(CH₂)₂— |
| I.a.712 | Cl | H | H | F | F | F | | —(CH₂)₂— |
| I.a.713 | CN | H | H | F | F | F | | —(CH₂)₂— |
| I.a.714 | F | H | H | CN | F | F | | —(CH₂)₂— |
| I.a.715 | CN | H | H | F | F | F | | —(CH₂)₂— |
| I.a.716 | F | H | F | H | F | F | | —(CH₂)₂— |
| I.a.717 | Cl | H | F | H | F | F | | —(CH₂)₂— |
| I.a.718 | CN | H | F | H | F | F | | —(CH₂)₂— |
| I.a.719 | F | F | F | H | F | F | | —(CH₂)₂— |
| I.a.720 | Cl | F | F | H | F | F | | —(CH₂)₂— |
| I.a.721 | F | Cl | F | H | F | F | | —(CH₂)₂— |
| I.a.722 | Cl | F | F | H | F | F | | —(CH₂)₂— |
| I.a.723 | CN | F | F | H | F | F | | —(CH₂)₂— |
| I.a.724 | F | CN | F | H | F | F | | —(CH₂)₂— |
| I.a.725 | CN | F | F | H | F | F | | —(CH₂)₂— |
| I.a.726 | F | F | H | F | F | F | | —(CH₂)₂— |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.727 | Cl | F | H | F | F | F | —(CH$_2$)$_2$— | |
| I.a.728 | F | Cl | H | F | F | F | —(CH$_2$)$_2$— | |
| I.a.729 | CN | F | H | F | F | F | —(CH$_2$)$_2$— | |
| I.a.730 | F | CN | H | F | F | F | —(CH$_2$)$_2$— | |
| I.a.731 | F | F | F | F | F | F | —(CH$_2$)$_2$— | |
| I.a.732 | Cl | F | F | F | F | F | —(CH$_2$)$_2$— | |
| I.a.733 | F | Cl | F | F | F | F | —(CH$_2$)$_2$— | |
| I.a.734 | CN | F | F | F | F | F | —(CH$_2$)$_2$— | |
| I.a.735 | F | CN | F | F | F | F | —(CH$_2$)$_2$— | |
| I.a.736 | H | F | F | F | F | F | —(CH$_2$)$_2$— | |
| I.a.737 | F | F | Br | F | F | F | —(CH$_2$)$_2$— | |
| I.a.738 | F | F | C≡CH | F | F | F | —(CH$_2$)$_2$— | |
| I.a.739 | CF$_3$ | Cl | H | H | F | F | —(CH$_2$)$_2$— | |
| I.a.740 | F | F | I | F | F | F | —(CH$_2$)$_2$— | |
| I.a.741 | F | H | H | H | F | F | —(CH$_2$)$_3$— | |
| I.a.742 | Cl | H | H | H | F | F | —(CH$_2$)$_3$— | |
| I.a.743 | Br | H | H | H | F | F | —(CH$_2$)$_3$— | |
| I.a.744 | CN | H | H | H | F | F | —(CH$_2$)$_3$— | |
| I.a.745 | CH$_3$ | H | H | H | F | F | —(CH$_2$)$_3$— | |
| I.a.746 | F | H | H | F | F | F | —(CH$_2$)$_3$— | |
| I.a.747 | Cl | H | H | F | F | F | —(CH$_2$)$_3$— | |
| I.a.748 | F | H | H | Cl | F | F | —(CH$_2$)$_3$— | |
| I.a.749 | Cl | H | H | F | F | F | —(CH$_2$)$_3$— | |
| I.a.750 | CN | H | H | F | F | F | —(CH$_2$)$_3$— | |
| I.a.751 | F | H | H | CN | F | F | —(CH$_2$)$_3$— | |
| I.a.752 | CN | H | H | F | F | F | —(CH$_2$)$_3$— | |
| I.a.753 | F | H | F | H | F | F | —(CH$_2$)$_3$— | |
| I.a.754 | Cl | H | F | H | F | F | —(CH$_2$)$_3$— | |
| I.a.755 | CN | H | F | H | F | F | —(CH$_2$)$_3$— | |
| I.a.756 | F | F | F | H | F | F | —(CH$_2$)$_3$— | |
| I.a.757 | Cl | F | F | H | F | F | —(CH$_2$)$_3$— | |
| I.a.758 | F | Cl | F | H | F | F | —(CH$_2$)$_3$— | |
| I.a.759 | Cl | F | F | H | F | F | —(CH$_2$)$_3$— | |
| I.a.760 | CN | F | F | H | F | F | —(CH$_2$)$_3$— | |
| I.a.761 | F | CN | F | H | F | F | —(CH$_2$)$_3$— | |
| I.a.762 | CN | F | F | H | F | F | —(CH$_2$)$_3$— | |
| I.a.763 | F | F | H | F | F | F | —(CH$_2$)$_3$— | |
| I.a.764 | Cl | F | H | F | F | F | —(CH$_2$)$_3$— | |
| I.a.765 | F | Cl | H | F | F | F | —(CH$_2$)$_3$— | |
| I.a.766 | CN | F | H | F | F | F | —(CH$_2$)$_3$— | |
| I.a.767 | F | CN | H | F | F | F | —(CH$_2$)$_3$— | |
| I.a.768 | F | F | F | F | F | F | —(CH$_2$)$_3$— | |
| I.a.769 | Cl | F | F | F | F | F | —(CH$_2$)$_3$— | |
| I.a.770 | F | Cl | F | F | F | F | —(CH$_2$)$_3$— | |
| I.a.771 | CN | F | F | F | F | F | —(CH$_2$)$_3$— | |
| I.a.772 | F | CN | F | F | F | F | —(CH$_2$)$_3$— | |
| I.a.773 | H | F | F | F | F | F | —(CH$_2$)$_3$— | |
| I.a.774 | F | F | Br | F | F | F | —(CH$_2$)$_3$— | |
| I.a.775 | F | F | C≡CH | F | F | F | —(CH$_2$)$_3$— | |
| I.a.776 | CF$_3$ | Cl | H | H | F | F | —(CH$_2$)$_3$— | |
| I.a.777 | F | F | I | F | F | F | —(CH$_2$)$_3$— | |
| I.a.778 | F | H | H | H | F | F | —(CH$_2$)$_4$— | |
| I.a.779 | Cl | H | H | H | F | F | —(CH$_2$)$_4$— | |
| I.a.780 | Br | H | H | H | F | F | —(CH$_2$)$_4$— | |
| I.a.781 | CN | H | H | H | F | F | —(CH$_2$)$_4$— | |
| I.a.782 | CH$_3$ | H | H | H | F | F | —(CH$_2$)$_4$— | |
| I.a.783 | F | H | H | F | F | F | —(CH$_2$)$_4$— | |
| I.a.784 | Cl | H | H | F | F | F | —(CH$_2$)$_4$— | |
| I.a.785 | F | H | H | Cl | F | F | —(CH$_2$)$_4$— | |
| I.a.786 | Cl | H | H | F | F | F | —(CH$_2$)$_4$— | |
| I.a.787 | CN | H | H | F | F | F | —(CH$_2$)$_4$— | |
| I.a.788 | F | H | H | CN | F | F | —(CH$_2$)$_4$— | |
| I.a.789 | CN | H | H | F | F | F | —(CH$_2$)$_4$— | |
| I.a.790 | F | H | F | H | F | F | —(CH$_2$)$_4$— | |
| I.a.791 | Cl | H | F | H | F | F | —(CH$_2$)$_4$— | |
| I.a.792 | CN | H | F | H | F | F | —(CH$_2$)$_4$— | |
| I.a.793 | F | F | F | H | F | F | —(CH$_2$)$_4$— | |
| I.a.794 | Cl | F | F | H | F | F | —(CH$_2$)$_4$— | |
| I.a.795 | F | Cl | F | H | F | F | —(CH$_2$)$_4$— | |
| I.a.796 | Cl | F | F | H | F | F | —(CH$_2$)$_4$— | |
| I.a.797 | CN | F | F | H | F | F | —(CH$_2$)$_4$— | |
| I.a.798 | F | CN | F | H | F | F | —(CH$_2$)$_4$— | |
| I.a.799 | CN | F | F | H | F | F | —(CH$_2$)$_4$— | |
| I.a.800 | F | F | H | F | F | F | —(CH$_2$)$_4$— | |
| I.a.801 | Cl | F | H | F | F | F | —(CH$_2$)$_4$— | |
| I.a.802 | F | Cl | H | F | F | F | —(CH$_2$)$_4$— | |
| I.a.803 | CN | F | H | F | F | F | —(CH$_2$)$_4$— | |
| I.a.804 | F | CN | H | F | F | F | —(CH$_2$)$_4$— | |
| I.a.805 | F | F | F | F | F | F | —(CH$_2$)$_4$— | |
| I.a.806 | Cl | F | F | F | F | F | —(CH$_2$)$_4$— | |
| I.a.807 | F | Cl | F | F | F | F | —(CH$_2$)$_4$— | |
| I.a.808 | CN | F | F | F | F | F | —(CH$_2$)$_4$— | |
| I.a.809 | F | CN | F | F | F | F | —(CH$_2$)$_4$— | |
| I.a.810 | H | F | F | F | F | F | —(CH$_2$)$_4$— | |
| I.a.811 | F | F | Br | F | F | F | —(CH$_2$)$_4$— | |
| I.a.812 | F | F | C≡CH | F | F | F | —(CH$_2$)$_4$— | |
| I.a.813 | CF$_3$ | Cl | H | H | F | F | —(CH$_2$)$_4$— | |
| I.a.814 | F | F | I | F | F | F | —(CH$_2$)$_4$— | |
| I.a.815 | F | H | H | H | F | F | —(CH$_2$)$_5$— | |
| I.a.816 | Cl | H | H | H | F | F | —(CH$_2$)$_5$— | |
| I.a.817 | Br | H | H | H | F | F | —(CH$_2$)$_5$— | |
| I.a.818 | CN | H | H | H | F | F | —(CH$_2$)$_5$— | |
| I.a.819 | CH$_3$ | H | H | H | F | F | —(CH$_2$)$_5$— | |
| I.a.820 | F | H | H | F | F | F | —(CH$_2$)$_5$— | |
| I.a.821 | Cl | H | H | F | F | F | —(CH$_2$)$_5$— | |
| I.a.822 | F | H | H | Cl | F | F | —(CH$_2$)$_5$— | |
| I.a.823 | Cl | H | H | F | F | F | —(CH$_2$)$_5$— | |
| I.a.824 | CN | H | H | F | F | F | —(CH$_2$)$_5$— | |
| I.a.825 | F | H | H | CN | F | F | —(CH$_2$)$_5$— | |
| I.a.826 | CN | H | H | F | F | F | —(CH$_2$)$_5$— | |
| I.a.827 | F | H | F | H | F | F | —(CH$_2$)$_5$— | |
| I.a.828 | Cl | H | F | H | F | F | —(CH$_2$)$_5$— | |
| I.a.829 | CN | H | F | H | F | F | —(CH$_2$)$_5$— | |
| I.a.830 | F | F | F | H | F | F | —(CH$_2$)$_5$— | |
| I.a.831 | Cl | F | F | H | F | F | —(CH$_2$)$_5$— | |
| I.a.832 | F | Cl | F | H | F | F | —(CH$_2$)$_5$— | |
| I.a.833 | Cl | F | F | H | F | F | —(CH$_2$)$_5$— | |
| I.a.834 | CN | F | F | H | F | F | —(CH$_2$)$_5$— | |
| I.a.835 | F | CN | F | H | F | F | —(CH$_2$)$_5$— | |
| I.a.836 | CN | F | F | H | F | F | —(CH$_2$)$_5$— | |
| I.a.837 | F | F | H | F | F | F | —(CH$_2$)$_5$— | |
| I.a.838 | Cl | F | H | F | F | F | —(CH$_2$)$_5$— | |
| I.a.839 | F | Cl | H | F | F | F | —(CH$_2$)$_5$— | |
| I.a.840 | CN | F | H | F | F | F | —(CH$_2$)$_5$— | |
| I.a.841 | F | CN | H | F | F | F | —(CH$_2$)$_5$— | |
| I.a.842 | F | F | F | F | F | F | —(CH$_2$)$_5$— | |
| I.a.843 | Cl | F | F | F | F | F | —(CH$_2$)$_5$— | |
| I.a.844 | F | Cl | F | F | F | F | —(CH$_2$)$_5$— | |
| I.a.845 | CN | F | F | F | F | F | —(CH$_2$)$_5$— | |
| I.a.846 | F | CN | F | F | F | F | —(CH$_2$)$_5$— | |
| I.a.847 | H | F | F | F | F | F | —(CH$_2$)$_5$— | |
| I.a.848 | F | F | Br | F | F | F | —(CH$_2$)$_5$— | |
| I.a.849 | F | F | C≡CH | F | F | F | —(CH$_2$)$_5$— | |
| I.a.850 | CF$_3$ | Cl | H | H | F | F | —(CH$_2$)$_5$— | |
| I.a.851 | F | F | I | F | F | F | —(CH$_2$)$_5$— | |
| I.a.852 | F | H | H | H | F | Cl | —(CH$_2$)$_2$— | |
| I.a.853 | Cl | H | H | H | F | Cl | —(CH$_2$)$_2$— | |
| I.a.854 | Br | H | H | H | F | Cl | —(CH$_2$)$_2$— | |
| I.a.855 | CN | H | H | H | F | Cl | —(CH$_2$)$_2$— | |
| I.a.856 | CH$_3$ | H | H | H | F | Cl | —(CH$_2$)$_2$— | |
| I.a.857 | F | H | H | F | F | Cl | —(CH$_2$)$_2$— | |
| I.a.858 | Cl | H | H | F | F | Cl | —(CH$_2$)$_2$— | |
| I.a.859 | F | H | H | Cl | F | Cl | —(CH$_2$)$_2$— | |
| I.a.860 | Cl | H | H | F | F | Cl | —(CH$_2$)$_2$— | |
| I.a.861 | CN | H | H | F | F | Cl | —(CH$_2$)$_2$— | |
| I.a.862 | F | H | H | CN | F | Cl | —(CH$_2$)$_2$— | |
| I.a.863 | CN | H | H | F | F | Cl | —(CH$_2$)$_2$— | |
| I.a.864 | F | H | F | H | F | Cl | —(CH$_2$)$_2$— | |
| I.a.865 | Cl | H | F | H | F | Cl | —(CH$_2$)$_2$— | |
| I.a.866 | CN | H | F | H | F | Cl | —(CH$_2$)$_2$— | |
| I.a.867 | F | F | F | H | F | Cl | —(CH$_2$)$_2$— | |
| I.a.868 | Cl | F | F | H | F | Cl | —(CH$_2$)$_2$— | |
| I.a.869 | F | Cl | F | H | F | Cl | —(CH$_2$)$_2$— | |
| I.a.870 | Cl | F | F | H | F | Cl | —(CH$_2$)$_2$— | |
| I.a.871 | CN | F | F | H | F | Cl | —(CH$_2$)$_2$— | |
| I.a.872 | F | CN | F | H | F | Cl | —(CH$_2$)$_2$— | |
| I.a.873 | CN | F | F | H | F | Cl | —(CH$_2$)$_2$— | |
| I.a.874 | F | F | H | F | F | Cl | —(CH$_2$)$_2$— | |
| I.a.875 | Cl | F | H | F | F | Cl | —(CH$_2$)$_2$— | |
| I.a.876 | F | Cl | H | F | F | Cl | —(CH$_2$)$_2$— | |
| I.a.877 | CN | F | H | F | F | Cl | —(CH$_2$)$_2$— | |
| I.a.878 | F | CN | H | F | F | Cl | —(CH$_2$)$_2$— | |
| I.a.879 | F | F | F | F | F | Cl | —(CH$_2$)$_2$— | |
| I.a.880 | Cl | F | F | F | F | Cl | —(CH$_2$)$_2$— | |
| I.a.881 | F | Cl | F | F | F | Cl | —(CH$_2$)$_2$— | |
| I.a.882 | CN | F | F | F | F | Cl | —(CH$_2$)$_2$— | |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.883 | F | CN | F | F | F | Cl | —(CH$_2$)$_2$— | |
| I.a.884 | H | F | F | F | F | Cl | —(CH$_2$)$_2$— | |
| I.a.885 | F | F | Br | F | F | Cl | —(CH$_2$)$_2$— | |
| I.a.886 | F | F | C≡CH | F | F | Cl | —(CH$_2$)$_2$— | |
| I.a.887 | CF$_3$ | Cl | H | H | F | Cl | —(CH$_2$)$_2$— | |
| I.a.888 | F | F | I | F | F | Cl | —(CH$_2$)$_2$— | |
| I.a.889 | F | H | H | H | F | Cl | —(CH$_2$)$_3$— | |
| I.a.890 | Cl | H | H | H | F | Cl | —(CH$_2$)$_3$— | |
| I.a.891 | Br | H | H | H | F | Cl | —(CH$_2$)$_3$— | |
| I.a.892 | CN | H | H | H | F | Cl | —(CH$_2$)$_3$— | |
| I.a.893 | CH$_3$ | H | H | H | F | Cl | —(CH$_2$)$_3$— | |
| I.a.894 | F | H | H | F | F | Cl | —(CH$_2$)$_3$— | |
| I.a.895 | Cl | H | H | F | F | Cl | —(CH$_2$)$_3$— | |
| I.a.896 | F | H | H | Cl | F | Cl | —(CH$_2$)$_3$— | |
| I.a.897 | Cl | H | H | F | F | Cl | —(CH$_2$)$_3$— | |
| I.a.898 | CN | H | H | F | F | Cl | —(CH$_2$)$_3$— | |
| I.a.899 | F | H | H | CN | F | Cl | —(CH$_2$)$_3$— | |
| I.a.900 | CN | H | H | F | F | Cl | —(CH$_2$)$_3$— | |
| I.a.901 | F | H | F | H | F | Cl | —(CH$_2$)$_3$— | |
| I.a.902 | Cl | H | F | H | F | Cl | —(CH$_2$)$_3$— | |
| I.a.903 | CN | H | F | H | F | Cl | —(CH$_2$)$_3$— | |
| I.a.904 | F | F | F | H | F | Cl | —(CH$_2$)$_3$— | |
| I.a.905 | Cl | F | F | H | F | Cl | —(CH$_2$)$_3$— | |
| I.a.906 | F | Cl | F | H | F | Cl | —(CH$_2$)$_3$— | |
| I.a.907 | Cl | F | F | H | F | Cl | —(CH$_2$)$_3$— | |
| I.a.908 | CN | F | F | H | F | Cl | —(CH$_2$)$_3$— | |
| I.a.909 | F | CN | F | H | F | Cl | —(CH$_2$)$_3$— | |
| I.a.910 | CN | F | F | H | F | Cl | —(CH$_2$)$_3$— | |
| I.a.911 | F | F | H | F | F | Cl | —(CH$_2$)$_3$— | |
| I.a.912 | Cl | F | H | F | F | Cl | —(CH$_2$)$_3$— | |
| I.a.913 | F | Cl | H | F | F | Cl | —(CH$_2$)$_3$— | |
| I.a.914 | CN | F | H | F | F | Cl | —(CH$_2$)$_3$— | |
| I.a.915 | F | CN | H | F | F | Cl | —(CH$_2$)$_3$— | |
| I.a.916 | F | F | F | F | F | Cl | —(CH$_2$)$_3$— | |
| I.a.917 | Cl | F | F | F | F | Cl | —(CH$_2$)$_3$— | |
| I.a.918 | F | Cl | F | F | F | Cl | —(CH$_2$)$_3$— | |
| I.a.919 | CN | F | F | F | F | Cl | —(CH$_2$)$_3$— | |
| I.a.920 | F | CN | F | F | F | Cl | —(CH$_2$)$_3$— | |
| I.a.921 | H | F | F | F | F | Cl | —(CH$_2$)$_3$— | |
| I.a.922 | F | F | Br | F | F | Cl | —(CH$_2$)$_3$— | |
| I.a.923 | F | F | C≡CH | F | F | Cl | —(CH$_2$)$_3$— | |
| I.a.924 | CF$_3$ | Cl | H | H | F | Cl | —(CH$_2$)$_3$— | |
| I.a.925 | F | F | I | F | F | Cl | —(CH$_2$)$_3$— | |
| I.a.926 | F | H | H | H | F | Cl | —(CH$_2$)$_4$— | |
| I.a.927 | Cl | H | H | H | F | Cl | —(CH$_2$)$_4$— | |
| I.a.928 | Br | H | H | H | F | Cl | —(CH$_2$)$_4$— | |
| I.a.929 | CN | H | H | H | F | Cl | —(CH$_2$)$_4$— | |
| I.a.930 | CH$_3$ | H | H | H | F | Cl | —(CH$_2$)$_4$— | |
| I.a.931 | F | H | H | F | F | Cl | —(CH$_2$)$_4$— | |
| I.a.932 | Cl | H | H | F | F | Cl | —(CH$_2$)$_4$— | |
| I.a.933 | F | H | H | Cl | F | Cl | —(CH$_2$)$_4$— | |
| I.a.934 | Cl | H | H | F | F | Cl | —(CH$_2$)$_4$— | |
| I.a.935 | CN | H | H | F | F | Cl | —(CH$_2$)$_4$— | |
| I.a.936 | F | H | H | CN | F | Cl | —(CH$_2$)$_4$— | |
| I.a.937 | CN | H | H | F | F | Cl | —(CH$_2$)$_4$— | |
| I.a.938 | F | H | F | H | F | Cl | —(CH$_2$)$_4$— | |
| I.a.939 | Cl | H | F | H | F | Cl | —(CH$_2$)$_4$— | |
| I.a.940 | CN | H | F | H | F | Cl | —(CH$_2$)$_4$— | |
| I.a.941 | F | F | F | H | F | Cl | —(CH$_2$)$_4$— | |
| I.a.942 | Cl | F | F | H | F | Cl | —(CH$_2$)$_4$— | |
| I.a.943 | F | Cl | F | H | F | Cl | —(CH$_2$)$_4$— | |
| I.a.944 | Cl | F | F | H | F | Cl | —(CH$_2$)$_4$— | |
| I.a.945 | CN | F | F | H | F | Cl | —(CH$_2$)$_4$— | |
| I.a.946 | F | CN | F | H | F | Cl | —(CH$_2$)$_4$— | |
| I.a.947 | CN | F | F | H | F | Cl | —(CH$_2$)$_4$— | |
| I.a.948 | F | F | H | F | F | Cl | —(CH$_2$)$_4$— | |
| I.a.949 | Cl | F | H | F | F | Cl | —(CH$_2$)$_4$— | |
| I.a.950 | F | Cl | H | F | F | Cl | —(CH$_2$)$_4$— | |
| I.a.951 | CN | F | H | F | F | Cl | —(CH$_2$)$_4$— | |
| I.a.952 | F | CN | H | F | F | Cl | —(CH$_2$)$_4$— | |
| I.a.953 | F | F | F | F | F | Cl | —(CH$_2$)$_4$— | |
| I.a.954 | Cl | F | F | F | F | Cl | —(CH$_2$)$_4$— | |
| I.a.955 | F | Cl | F | F | F | Cl | —(CH$_2$)$_4$— | |
| I.a.956 | CN | F | F | F | F | Cl | —(CH$_2$)$_4$— | |
| I.a.957 | F | CN | F | F | F | Cl | —(CH$_2$)$_4$— | |
| I.a.958 | H | F | F | F | F | Cl | —(CH$_2$)$_4$— | |
| I.a.959 | F | F | Br | F | F | Cl | —(CH$_2$)$_4$— | |
| I.a.960 | F | F | C≡CH | F | F | Cl | —(CH$_2$)$_4$— | |
| I.a.961 | CF$_3$ | Cl | H | H | F | Cl | —(CH$_2$)$_4$— | |
| I.a.962 | F | F | I | F | F | Cl | —(CH$_2$)$_4$— | |
| I.a.963 | F | H | H | H | F | Cl | —(CH$_2$)$_5$— | |
| I.a.964 | Cl | H | H | H | F | Cl | —(CH$_2$)$_5$— | |
| I.a.965 | Br | H | H | H | F | Cl | —(CH$_2$)$_5$— | |
| I.a.966 | CN | H | H | H | F | Cl | —(CH$_2$)$_5$— | |
| I.a.967 | CH$_3$ | H | H | H | F | Cl | —(CH$_2$)$_5$— | |
| I.a.968 | F | H | H | F | F | Cl | —(CH$_2$)$_5$— | |
| I.a.969 | Cl | H | H | F | F | Cl | —(CH$_2$)$_5$— | |
| I.a.970 | F | H | H | Cl | F | Cl | —(CH$_2$)$_5$— | |
| I.a.971 | Cl | H | H | F | F | Cl | —(CH$_2$)$_5$— | |
| I.a.972 | CN | H | H | F | F | Cl | —(CH$_2$)$_5$— | |
| I.a.973 | F | H | H | CN | F | Cl | —(CH$_2$)$_5$— | |
| I.a.974 | CN | H | H | F | F | Cl | —(CH$_2$)$_5$— | |
| I.a.975 | F | H | F | H | F | Cl | —(CH$_2$)$_5$— | |
| I.a.976 | Cl | H | F | H | F | Cl | —(CH$_2$)$_5$— | |
| I.a.977 | CN | H | F | H | F | Cl | —(CH$_2$)$_5$— | |
| I.a.978 | F | F | F | H | F | Cl | —(CH$_2$)$_5$— | |
| I.a.979 | Cl | F | F | H | F | Cl | —(CH$_2$)$_5$— | |
| I.a.980 | F | Cl | F | H | F | Cl | —(CH$_2$)$_5$— | |
| I.a.981 | Cl | F | F | H | F | Cl | —(CH$_2$)$_5$— | |
| I.a.982 | CN | F | F | H | F | Cl | —(CH$_2$)$_5$— | |
| I.a.983 | F | CN | F | H | F | Cl | —(CH$_2$)$_5$— | |
| I.a.984 | CN | F | F | H | F | Cl | —(CH$_2$)$_5$— | |
| I.a.985 | F | F | H | F | F | Cl | —(CH$_2$)$_5$— | |
| I.a.986 | Cl | F | H | F | F | Cl | —(CH$_2$)$_5$— | |
| I.a.987 | F | Cl | H | F | F | Cl | —(CH$_2$)$_5$— | |
| I.a.988 | CN | F | H | F | F | Cl | —(CH$_2$)$_5$— | |
| I.a.989 | F | CN | H | F | F | Cl | —(CH$_2$)$_5$— | |
| I.a.990 | F | F | F | F | F | Cl | —(CH$_2$)$_5$— | |
| I.a.991 | Cl | F | F | F | F | Cl | —(CH$_2$)$_5$— | |
| I.a.992 | F | Cl | F | F | F | Cl | —(CH$_2$)$_5$— | |
| I.a.993 | CN | F | F | F | F | Cl | —(CH$_2$)$_5$— | |
| I.a.994 | F | CN | F | F | F | Cl | —(CH$_2$)$_5$— | |
| I.a.995 | H | F | F | F | F | Cl | —(CH$_2$)$_5$— | |
| I.a.996 | F | F | Br | F | F | Cl | —(CH$_2$)$_5$— | |
| I.a.997 | F | F | C≡CH | F | F | Cl | —(CH$_2$)$_5$— | |
| I.a.998 | CF$_3$ | Cl | H | H | F | Cl | —(CH$_2$)$_5$— | |
| I.a.999 | F | F | I | F | F | Cl | —(CH$_2$)$_5$— | |
| I.a.1000 | F | H | H | H | F | C$_2$H$_5$ | CH$_3$ | H |
| I.a.1001 | Cl | H | H | H | F | C$_2$H$_5$ | CH$_3$ | H |
| I.a.1002 | Br | H | H | H | F | C$_2$H$_5$ | CH$_3$ | H |
| I.a.1003 | CN | H | H | H | F | C$_2$H$_5$ | CH$_3$ | H |
| I.a.1004 | CH$_3$ | H | H | H | F | C$_2$H$_5$ | CH$_3$ | H |
| I.a.1005 | F | H | H | F | F | C$_2$H$_5$ | CH$_3$ | H |
| I.a.1006 | Cl | H | H | F | F | C$_2$H$_5$ | CH$_3$ | H |
| I.a.1007 | F | H | H | Cl | F | C$_2$H$_5$ | CH$_3$ | H |
| I.a.1008 | Cl | H | H | F | F | C$_2$H$_5$ | CH$_3$ | H |
| I.a.1009 | CN | H | H | F | F | C$_2$H$_5$ | CH$_3$ | H |
| I.a.1010 | F | H | H | CN | F | C$_2$H$_5$ | CH$_3$ | H |
| I.a.1011 | CN | H | H | F | F | C$_2$H$_5$ | CH$_3$ | H |
| I.a.1012 | F | H | F | H | F | C$_2$H$_5$ | CH$_3$ | H |
| I.a.1013 | Cl | H | F | H | F | C$_2$H$_5$ | CH$_3$ | H |
| I.a.1014 | CN | H | F | H | F | C$_2$H$_5$ | CH$_3$ | H |
| I.a.1015 | F | F | F | H | F | C$_2$H$_5$ | CH$_3$ | H |
| I.a.1016 | Cl | F | F | H | F | C$_2$H$_5$ | CH$_3$ | H |
| I.a.1017 | F | Cl | F | H | F | C$_2$H$_5$ | CH$_3$ | H |
| I.a.1018 | Cl | F | F | H | F | C$_2$H$_5$ | CH$_3$ | H |
| I.a.1019 | CN | F | F | H | F | C$_2$H$_5$ | CH$_3$ | H |
| I.a.1020 | F | CN | F | H | F | C$_2$H$_5$ | CH$_3$ | H |
| I.a.1021 | CN | F | F | H | F | C$_2$H$_5$ | CH$_3$ | H |
| I.a.1022 | F | F | H | F | F | C$_2$H$_5$ | CH$_3$ | H |
| I.a.1023 | Cl | F | H | F | F | C$_2$H$_5$ | CH$_3$ | H |
| I.a.1024 | F | Cl | H | F | F | C$_2$H$_5$ | CH$_3$ | H |
| I.a.1025 | CN | F | H | F | F | C$_2$H$_5$ | CH$_3$ | H |
| I.a.1026 | F | CN | H | F | F | C$_2$H$_5$ | CH$_3$ | H |
| I.a.1027 | F | F | F | F | F | C$_2$H$_5$ | CH$_3$ | H |
| I.a.1028 | Cl | F | F | F | F | C$_2$H$_5$ | CH$_3$ | H |
| I.a.1029 | F | Cl | F | F | F | C$_2$H$_5$ | CH$_3$ | H |
| I.a.1030 | CN | F | F | F | F | C$_2$H$_5$ | CH$_3$ | H |
| I.a.1031 | F | CN | F | F | F | C$_2$H$_5$ | CH$_3$ | H |
| I.a.1032 | H | F | F | F | F | C$_2$H$_5$ | CH$_3$ | H |
| I.a.1033 | F | F | Br | F | F | C$_2$H$_5$ | CH$_3$ | H |
| I.a.1034 | F | F | C≡CH | F | F | C$_2$H$_5$ | CH$_3$ | H |
| I.a.1035 | CF$_3$ | Cl | H | H | F | C$_2$H$_5$ | CH$_3$ | H |
| I.a.1036 | F | F | I | F | F | C$_2$H$_5$ | CH$_3$ | H |
| I.a.1037 | F | H | H | H | F | C$_2$H$_5$ | C$_2$H$_5$ | H |
| I.a.1038 | Cl | H | H | H | F | C$_2$H$_5$ | C$_2$H$_5$ | H |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1039 | Br | H | H | H | F | $C_2H_5$ | $C_2H_5$ | H |
| I.a.1040 | CN | H | H | H | F | $C_2H_5$ | $C_2H_5$ | H |
| I.a.1041 | $CH_3$ | H | H | H | F | $C_2H_5$ | $C_2H_5$ | H |
| I.a.1042 | F | H | H | F | F | $C_2H_5$ | $C_2H_5$ | H |
| I.a.1043 | Cl | H | H | F | F | $C_2H_5$ | $C_2H_5$ | H |
| I.a.1044 | F | H | H | Cl | F | $C_2H_5$ | $C_2H_5$ | H |
| I.a.1045 | Cl | H | H | F | F | $C_2H_5$ | $C_2H_5$ | H |
| I.a.1046 | CN | H | H | F | F | $C_2H_5$ | $C_2H_5$ | H |
| I.a.1047 | F | H | H | CN | F | $C_2H_5$ | $C_2H_5$ | H |
| I.a.1048 | CN | H | H | F | F | $C_2H_5$ | $C_2H_5$ | H |
| I.a.1049 | F | H | F | H | F | $C_2H_5$ | $C_2H_5$ | H |
| I.a.1050 | Cl | H | F | H | F | $C_2H_5$ | $C_2H_5$ | H |
| I.a.1051 | CN | H | F | H | F | $C_2H_5$ | $C_2H_5$ | H |
| I.a.1052 | F | F | F | H | F | $C_2H_5$ | $C_2H_5$ | H |
| I.a.1053 | Cl | F | F | H | F | $C_2H_5$ | $C_2H_5$ | H |
| I.a.1054 | F | Cl | F | H | F | $C_2H_5$ | $C_2H_5$ | H |
| I.a.1055 | Cl | F | F | H | F | $C_2H_5$ | $C_2H_5$ | H |
| I.a.1056 | CN | F | F | H | F | $C_2H_5$ | $C_2H_5$ | H |
| I.a.1057 | F | CN | F | H | F | $C_2H_5$ | $C_2H_5$ | H |
| I.a.1058 | CN | F | F | H | F | $C_2H_5$ | $C_2H_5$ | H |
| I.a.1059 | F | F | H | F | F | $C_2H_5$ | $C_2H_5$ | H |
| I.a.1060 | Cl | F | H | F | F | $C_2H_5$ | $C_2H_5$ | H |
| I.a.1061 | F | Cl | H | F | F | $C_2H_5$ | $C_2H_5$ | H |
| I.a.1062 | CN | F | H | F | F | $C_2H_5$ | $C_2H_5$ | H |
| I.a.1063 | F | CN | H | F | F | $C_2H_5$ | $C_2H_5$ | H |
| I.a.1064 | F | F | F | F | F | $C_2H_5$ | $C_2H_5$ | H |
| I.a.1065 | Cl | F | F | F | F | $C_2H_5$ | $C_2H_5$ | H |
| I.a.1066 | F | Cl | F | F | F | $C_2H_5$ | $C_2H_5$ | H |
| I.a.1067 | CN | F | F | F | F | $C_2H_5$ | $C_2H_5$ | H |
| I.a.1068 | F | CN | F | F | F | $C_2H_5$ | $C_2H_5$ | H |
| I.a.1069 | H | F | F | F | F | $C_2H_5$ | $C_2H_5$ | H |
| I.a.1070 | F | F | Br | F | F | $C_2H_5$ | $C_2H_5$ | H |
| I.a.1071 | F | F | C≡CH | F | F | $C_2H_5$ | $C_2H_5$ | H |
| I.a.1072 | $CF_3$ | Cl | H | H | F | $C_2H_5$ | $C_2H_5$ | H |
| I.a.1073 | F | F | I | F | F | $C_2H_5$ | $C_2H_5$ | H |
| I.a.1074 | F | H | H | H | F | $C_2H_5$ | $C_2H_5$ | $CH_3$ |
| I.a.1075 | Cl | H | H | H | F | $C_2H_5$ | $C_2H_5$ | $CH_3$ |
| I.a.1076 | Br | H | H | H | F | $C_2H_5$ | $C_2H_5$ | $CH_3$ |
| I.a.1077 | CN | H | H | H | F | $C_2H_5$ | $C_2H_5$ | $CH_3$ |
| I.a.1078 | $CH_3$ | H | H | H | F | $C_2H_5$ | $C_2H_5$ | $CH_3$ |
| I.a.1079 | F | H | H | F | F | $C_2H_5$ | $C_2H_5$ | $CH_3$ |
| I.a.1080 | Cl | H | H | F | F | $C_2H_5$ | $C_2H_5$ | $CH_3$ |
| I.a.1081 | F | H | H | Cl | F | $C_2H_5$ | $C_2H_5$ | $CH_3$ |
| I.a.1082 | Cl | H | H | F | F | $C_2H_5$ | $C_2H_5$ | $CH_3$ |
| I.a.1083 | CN | H | H | F | F | $C_2H_5$ | $C_2H_5$ | $CH_3$ |
| I.a.1084 | F | H | H | CN | F | $C_2H_5$ | $C_2H_5$ | $CH_3$ |
| I.a.1085 | CN | H | H | F | F | $C_2H_5$ | $C_2H_5$ | $CH_3$ |
| I.a.1086 | F | H | F | H | F | $C_2H_5$ | $C_2H_5$ | $CH_3$ |
| I.a.1087 | Cl | H | F | H | F | $C_2H_5$ | $C_2H_5$ | $CH_3$ |
| I.a.1088 | CN | H | F | H | F | $C_2H_5$ | $C_2H_5$ | $CH_3$ |
| I.a.1089 | F | F | F | H | F | $C_2H_5$ | $C_2H_5$ | $CH_3$ |
| I.a.1090 | Cl | F | F | H | F | $C_2H_5$ | $C_2H_5$ | $CH_3$ |
| I.a.1091 | F | Cl | F | H | F | $C_2H_5$ | $C_2H_5$ | $CH_3$ |
| I.a.1092 | Cl | F | F | H | F | $C_2H_5$ | $C_2H_5$ | $CH_3$ |
| I.a.1093 | CN | F | F | H | F | $C_2H_5$ | $C_2H_5$ | $CH_3$ |
| I.a.1094 | F | CN | F | H | F | $C_2H_5$ | $C_2H_5$ | $CH_3$ |
| I.a.1095 | CN | F | F | H | F | $C_2H_5$ | $C_2H_5$ | $CH_3$ |
| I.a.1096 | F | F | H | F | F | $C_2H_5$ | $C_2H_5$ | $CH_3$ |
| I.a.1097 | Cl | F | H | F | F | $C_2H_5$ | $C_2H_5$ | $CH_3$ |
| I.a.1098 | F | Cl | H | F | F | $C_2H_5$ | $C_2H_5$ | $CH_3$ |
| I.a.1099 | CN | F | H | F | F | $C_2H_5$ | $C_2H_5$ | $CH_3$ |
| I.a.1100 | F | CN | H | F | F | $C_2H_5$ | $C_2H_5$ | $CH_3$ |
| I.a.1101 | F | F | F | F | F | $C_2H_5$ | $C_2H_5$ | $CH_3$ |
| I.a.1102 | Cl | F | F | F | F | $C_2H_5$ | $C_2H_5$ | $CH_3$ |
| I.a.1103 | F | Cl | F | F | F | $C_2H_5$ | $C_2H_5$ | $CH_3$ |
| I.a.1104 | CN | F | F | F | F | $C_2H_5$ | $C_2H_5$ | $CH_3$ |
| I.a.1105 | F | CN | F | F | F | $C_2H_5$ | $C_2H_5$ | $CH_3$ |
| I.a.1106 | H | F | F | F | F | $C_2H_5$ | $C_2H_5$ | $CH_3$ |
| I.a.1107 | F | F | Br | F | F | $C_2H_5$ | $C_2H_5$ | $CH_3$ |
| I.a.1108 | F | F | C≡CH | F | F | $C_2H_5$ | $C_2H_5$ | $CH_3$ |
| I.a.1109 | $CF_3$ | Cl | H | H | F | $C_2H_5$ | $C_2H_5$ | $CH_3$ |
| I.a.1110 | F | F | I | F | F | $C_2H_5$ | $C_2H_5$ | $CH_3$ |
| I.a.1111 | F | H | H | H | F | $C_2H_5$ | $CH_3$ | $CH_3$ |
| I.a.1112 | Cl | H | H | H | F | $C_2H_5$ | $CH_3$ | $CH_3$ |
| I.a.1113 | Br | H | H | H | F | $C_2H_5$ | $CH_3$ | $CH_3$ |
| I.a.1114 | CN | H | H | H | F | $C_2H_5$ | $CH_3$ | $CH_3$ |
| I.a.1115 | $CH_3$ | H | H | H | F | $C_2H_5$ | $CH_3$ | $CH_3$ |
| I.a.1116 | F | H | H | F | F | $C_2H_5$ | $CH_3$ | $CH_3$ |
| I.a.1117 | Cl | H | H | F | F | $C_2H_5$ | $CH_3$ | $CH_3$ |
| I.a.1118 | F | H | H | Cl | F | $C_2H_5$ | $CH_3$ | $CH_3$ |
| I.a.1119 | Cl | H | H | F | F | $C_2H_5$ | $CH_3$ | $CH_3$ |
| I.a.1120 | CN | H | H | F | F | $C_2H_5$ | $CH_3$ | $CH_3$ |
| I.a.1121 | F | H | H | CN | F | $C_2H_5$ | $CH_3$ | $CH_3$ |
| I.a.1122 | CN | H | H | F | F | $C_2H_5$ | $CH_3$ | $CH_3$ |
| I.a.1123 | F | H | F | H | F | $C_2H_5$ | $CH_3$ | $CH_3$ |
| I.a.1124 | Cl | H | F | H | F | $C_2H_5$ | $CH_3$ | $CH_3$ |
| I.a.1125 | CN | H | F | H | F | $C_2H_5$ | $CH_3$ | $CH_3$ |
| I.a.1126 | F | F | F | H | F | $C_2H_5$ | $CH_3$ | $CH_3$ |
| I.a.1127 | Cl | F | F | H | F | $C_2H_5$ | $CH_3$ | $CH_3$ |
| I.a.1128 | F | Cl | F | H | F | $C_2H_5$ | $CH_3$ | $CH_3$ |
| I.a.1129 | Cl | F | F | H | F | $C_2H_5$ | $CH_3$ | $CH_3$ |
| I.a.1130 | CN | F | F | H | F | $C_2H_5$ | $CH_3$ | $CH_3$ |
| I.a.1131 | F | CN | F | H | F | $C_2H_5$ | $CH_3$ | $CH_3$ |
| I.a.1132 | CN | F | F | H | F | $C_2H_5$ | $CH_3$ | $CH_3$ |
| I.a.1133 | F | F | H | F | F | $C_2H_5$ | $CH_3$ | $CH_3$ |
| I.a.1134 | Cl | F | H | F | F | $C_2H_5$ | $CH_3$ | $CH_3$ |
| I.a.1135 | F | Cl | H | F | F | $C_2H_5$ | $CH_3$ | $CH_3$ |
| I.a.1136 | CN | F | H | F | F | $C_2H_5$ | $CH_3$ | $CH_3$ |
| I.a.1137 | F | CN | H | F | F | $C_2H_5$ | $CH_3$ | $CH_3$ |
| I.a.1138 | F | F | F | F | F | $C_2H_5$ | $CH_3$ | $CH_3$ |
| I.a.1139 | Cl | F | F | F | F | $C_2H_5$ | $CH_3$ | $CH_3$ |
| I.a.1140 | F | Cl | F | F | F | $C_2H_5$ | $CH_3$ | $CH_3$ |
| I.a.1141 | CN | F | F | F | F | $C_2H_5$ | $CH_3$ | $CH_3$ |
| I.a.1142 | F | CN | F | F | F | $C_2H_5$ | $CH_3$ | $CH_3$ |
| I.a.1143 | H | F | F | F | F | $C_2H_5$ | $CH_3$ | $CH_3$ |
| I.a.1144 | F | F | Br | F | F | $C_2H_5$ | $CH_3$ | $CH_3$ |
| I.a.1145 | F | F | C≡CH | F | F | $C_2H_5$ | $CH_3$ | $CH_3$ |
| I.a.1146 | $CF_3$ | Cl | H | H | F | $C_2H_5$ | $CH_3$ | $CH_3$ |
| I.a.1147 | F | F | I | F | F | $C_2H_5$ | $CH_3$ | $CH_3$ |
| I.a.1148 | F | H | H | H | F | Cl | $CH_3$ | H |
| I.a.1149 | Cl | H | H | H | F | Cl | $CH_3$ | H |
| I.a.1150 | Br | H | H | H | F | Cl | $CH_3$ | H |
| I.a.1151 | CN | H | H | H | F | Cl | $CH_3$ | H |
| I.a.1152 | $CH_3$ | H | H | H | F | Cl | $CH_3$ | H |
| I.a.1153 | F | H | H | F | F | Cl | $CH_3$ | H |
| I.a.1154 | Cl | H | H | F | F | Cl | $CH_3$ | H |
| I.a.1155 | F | H | H | Cl | F | Cl | $CH_3$ | H |
| I.a.1156 | Cl | H | H | F | F | Cl | $CH_3$ | H |
| I.a.1157 | CN | H | H | F | F | Cl | $CH_3$ | H |
| I.a.1158 | F | H | H | CN | F | Cl | $CH_3$ | H |
| I.a.1159 | CN | H | H | F | F | Cl | $CH_3$ | H |
| I.a.1160 | F | H | F | H | F | Cl | $CH_3$ | H |
| I.a.1161 | Cl | H | F | H | F | Cl | $CH_3$ | H |
| I.a.1162 | CN | H | F | H | F | Cl | $CH_3$ | H |
| I.a.1163 | F | F | F | H | F | Cl | $CH_3$ | H |
| I.a.1164 | Cl | F | F | H | F | Cl | $CH_3$ | H |
| I.a.1165 | F | Cl | F | H | F | Cl | $CH_3$ | H |
| I.a.1166 | Cl | F | F | H | F | Cl | $CH_3$ | H |
| I.a.1167 | CN | F | F | H | F | Cl | $CH_3$ | H |
| I.a.1168 | F | CN | F | H | F | Cl | $CH_3$ | H |
| I.a.1169 | CN | F | F | H | F | Cl | $CH_3$ | H |
| I.a.1170 | F | F | H | F | F | Cl | $CH_3$ | H |
| I.a.1171 | Cl | F | H | F | F | Cl | $CH_3$ | H |
| I.a.1172 | F | Cl | H | F | F | Cl | $CH_3$ | H |
| I.a.1173 | CN | F | H | F | F | Cl | $CH_3$ | H |
| I.a.1174 | F | CN | H | F | F | Cl | $CH_3$ | H |
| I.a.1175 | F | F | F | F | F | Cl | $CH_3$ | H |
| I.a.1176 | Cl | F | F | F | F | Cl | $CH_3$ | H |
| I.a.1177 | F | Cl | F | F | F | Cl | $CH_3$ | H |
| I.a.1178 | CN | F | F | F | F | Cl | $CH_3$ | H |
| I.a.1179 | F | CN | F | F | F | Cl | $CH_3$ | H |
| I.a.1180 | H | F | F | F | F | Cl | $CH_3$ | H |
| I.a.1181 | F | F | Br | F | F | Cl | $CH_3$ | H |
| I.a.1182 | F | F | C≡CH | F | F | Cl | $CH_3$ | H |
| I.a.1183 | $CF_3$ | Cl | H | H | F | Cl | $CH_3$ | H |
| I.a.1184 | F | F | I | F | F | Cl | $CH_3$ | H |
| I.a.1185 | F | H | H | H | F | $CH_2Cl$ | Cl | $CH_3$ |
| I.a.1186 | Cl | H | H | H | F | $CH_2Cl$ | Cl | $CH_3$ |
| I.a.1187 | Br | H | H | H | F | $CH_2Cl$ | Cl | $CH_3$ |
| I.a.1188 | CN | H | H | H | F | $CH_2Cl$ | Cl | $CH_3$ |
| I.a.1189 | $CH_3$ | H | H | H | F | $CH_2Cl$ | Cl | $CH_3$ |
| I.a.1190 | F | H | H | F | F | $CH_2Cl$ | Cl | $CH_3$ |
| I.a.1191 | Cl | H | H | F | F | $CH_2Cl$ | Cl | $CH_3$ |
| I.a.1192 | F | H | H | Cl | F | $CH_2Cl$ | Cl | $CH_3$ |
| I.a.1193 | Cl | H | H | F | F | $CH_2Cl$ | Cl | $CH_3$ |
| I.a.1194 | CN | H | H | F | F | $CH_2Cl$ | Cl | $CH_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1195 | F | H | H | CN | F | CH$_2$Cl | Cl | CH$_3$ |
| I.a.1196 | CN | H | H | F | F | CH$_2$Cl | Cl | CH$_3$ |
| I.a.1197 | F | H | F | H | F | CH$_2$Cl | Cl | CH$_3$ |
| I.a.1198 | Cl | H | F | H | F | CH$_2$Cl | Cl | CH$_3$ |
| I.a.1199 | CN | H | F | H | F | CH$_2$Cl | Cl | CH$_3$ |
| I.a.1200 | F | F | F | H | F | CH$_2$Cl | Cl | CH$_3$ |
| I.a.1201 | Cl | F | F | H | F | CH$_2$Cl | Cl | CH$_3$ |
| I.a.1202 | F | Cl | F | H | F | CH$_2$Cl | Cl | CH$_3$ |
| I.a.1203 | Cl | F | F | H | F | CH$_2$Cl | Cl | CH$_3$ |
| I.a.1204 | CN | F | F | H | F | CH$_2$Cl | Cl | CH$_3$ |
| I.a.1205 | F | CN | F | H | F | CH$_2$Cl | Cl | CH$_3$ |
| I.a.1206 | CN | F | F | H | F | CH$_2$Cl | Cl | CH$_3$ |
| I.a.1207 | F | F | H | F | F | CH$_2$Cl | Cl | CH$_3$ |
| I.a.1208 | Cl | F | H | F | F | CH$_2$Cl | Cl | CH$_3$ |
| I.a.1209 | F | Cl | H | F | F | CH$_2$Cl | Cl | CH$_3$ |
| I.a.1210 | CN | F | H | F | F | CH$_2$Cl | Cl | CH$_3$ |
| I.a.1211 | F | CN | H | F | F | CH$_2$Cl | Cl | CH$_3$ |
| I.a.1212 | F | F | F | F | F | CH$_2$Cl | Cl | CH$_3$ |
| I.a.1213 | Cl | F | F | F | F | CH$_2$Cl | Cl | CH$_3$ |
| I.a.1214 | F | Cl | F | F | F | CH$_2$Cl | Cl | CH$_3$ |
| I.a.1215 | CN | F | F | F | F | CH$_2$Cl | Cl | CH$_3$ |
| I.a.1216 | F | CN | F | F | F | CH$_2$Cl | Cl | CH$_3$ |
| I.a.1217 | H | F | F | F | F | CH$_2$Cl | Cl | CH$_3$ |
| I.a.1218 | F | F | Br | F | F | CH$_2$Cl | Cl | CH$_3$ |
| I.a.1219 | F | F | C≡CH | F | F | CH$_2$Cl | Cl | CH$_3$ |
| I.a.1220 | CF$_3$ | Cl | H | H | F | CH$_2$Cl | Cl | CH$_3$ |
| I.a.1221 | F | F | I | F | F | CH$_2$Cl | Cl | CH$_3$ |
| I.a.1222 | F | H | H | H | F | CN | CH$_3$ | CH$_3$ |
| I.a.1223 | Cl | H | H | H | F | CN | CH$_3$ | CH$_3$ |
| I.a.1224 | Br | H | H | H | F | CN | CH$_3$ | CH$_3$ |
| I.a.1225 | CN | H | H | H | F | CN | CH$_3$ | CH$_3$ |
| I.a.1226 | CH$_3$ | H | H | H | F | CN | CH$_3$ | CH$_3$ |
| I.a.1227 | F | H | H | F | F | CN | CH$_3$ | CH$_3$ |
| I.a.1228 | Cl | H | H | F | F | CN | CH$_3$ | CH$_3$ |
| I.a.1229 | F | H | H | Cl | F | CN | CH$_3$ | CH$_3$ |
| I.a.1230 | Cl | H | H | F | F | CN | CH$_3$ | CH$_3$ |
| I.a.1231 | CN | H | H | F | F | CN | CH$_3$ | CH$_3$ |
| I.a.1232 | F | H | H | CN | F | CN | CH$_3$ | CH$_3$ |
| I.a.1233 | CN | H | H | F | F | CN | CH$_3$ | CH$_3$ |
| I.a.1234 | F | H | F | H | F | CN | CH$_3$ | CH$_3$ |
| I.a.1235 | Cl | H | F | H | F | CN | CH$_3$ | CH$_3$ |
| I.a.1236 | CN | H | F | H | F | CN | CH$_3$ | CH$_3$ |
| I.a.1237 | F | F | F | H | F | CN | CH$_3$ | CH$_3$ |
| I.a.1238 | Cl | F | F | H | F | CN | CH$_3$ | CH$_3$ |
| I.a.1239 | F | Cl | F | H | F | CN | CH$_3$ | CH$_3$ |
| I.a.1240 | Cl | F | F | H | F | CN | CH$_3$ | CH$_3$ |
| I.a.1241 | CN | F | F | H | F | CN | CH$_3$ | CH$_3$ |
| I.a.1242 | F | CN | F | H | F | CN | CH$_3$ | CH$_3$ |
| I.a.1243 | CN | F | F | H | F | CN | CH$_3$ | CH$_3$ |
| I.a.1244 | F | F | H | F | F | CN | CH$_3$ | CH$_3$ |
| I.a.1245 | Cl | F | H | F | F | CN | CH$_3$ | CH$_3$ |
| I.a.1246 | F | Cl | H | F | F | CN | CH$_3$ | CH$_3$ |
| I.a.1247 | CN | F | H | F | F | CN | CH$_3$ | CH$_3$ |
| I.a.1248 | F | CN | H | F | F | CN | CH$_3$ | CH$_3$ |
| I.a.1249 | F | F | F | F | F | CN | CH$_3$ | CH$_3$ |
| I.a.1250 | Cl | F | F | F | F | CN | CH$_3$ | CH$_3$ |
| I.a.1251 | F | Cl | F | F | F | CN | CH$_3$ | CH$_3$ |
| I.a.1252 | CN | F | F | F | F | CN | CH$_3$ | CH$_3$ |
| I.a.1253 | F | CN | F | F | F | CN | CH$_3$ | CH$_3$ |
| I.a.1254 | H | F | F | F | F | CN | CH$_3$ | CH$_3$ |
| I.a.1255 | F | F | Br | F | F | CN | CH$_3$ | CH$_3$ |
| I.a.1256 | F | F | C≡CH | F | F | CN | CH$_3$ | CH$_3$ |
| I.a.1257 | CF$_3$ | Cl | H | H | F | CN | CH$_3$ | CH$_3$ |
| I.a.1258 | F | F | I | F | F | CN | CH$_3$ | CH$_3$ |
| I.a.1259 | F | H | H | H | F | OCH$_3$ | H | H |
| I.a.1260 | Cl | H | H | H | F | OCH$_3$ | H | H |
| I.a.1261 | Br | H | H | H | F | OCH$_3$ | H | H |
| I.a.1262 | CN | H | H | H | F | OCH$_3$ | H | H |
| I.a.1263 | CH$_3$ | H | H | H | F | OCH$_3$ | H | H |
| I.a.1264 | F | H | H | F | F | OCH$_3$ | H | H |
| I.a.1265 | Cl | H | H | F | F | OCH$_3$ | H | H |
| I.a.1266 | F | H | H | Cl | F | OCH$_3$ | H | H |
| I.a.1267 | Cl | H | H | F | F | OCH$_3$ | H | H |
| I.a.1268 | CN | H | H | F | F | OCH$_3$ | H | H |
| I.a.1269 | F | H | H | CN | F | OCH$_3$ | H | H |
| I.a.1270 | CN | H | H | F | F | OCH$_3$ | H | H |
| I.a.1271 | F | H | F | H | F | OCH$_3$ | H | H |
| I.a.1272 | Cl | H | F | H | F | OCH$_3$ | H | H |
| I.a.1273 | CN | H | F | H | F | OCH$_3$ | H | H |
| I.a.1274 | F | F | F | H | F | OCH$_3$ | H | H |
| I.a.1275 | Cl | F | F | H | F | OCH$_3$ | H | H |
| I.a.1276 | F | Cl | F | H | F | OCH$_3$ | H | H |
| I.a.1277 | Cl | F | F | H | F | OCH$_3$ | H | H |
| I.a.1278 | CN | F | F | H | F | OCH$_3$ | H | H |
| I.a.1279 | F | CN | F | H | F | OCH$_3$ | H | H |
| I.a.1280 | CN | F | F | H | F | OCH$_3$ | H | H |
| I.a.1281 | F | F | H | F | F | OCH$_3$ | H | H |
| I.a.1282 | Cl | F | H | F | F | OCH$_3$ | H | H |
| I.a.1283 | F | Cl | H | F | F | OCH$_3$ | H | H |
| I.a.1284 | CN | F | H | F | F | OCH$_3$ | H | H |
| I.a.1285 | F | CN | H | F | F | OCH$_3$ | H | H |
| I.a.1286 | F | F | F | F | F | OCH$_3$ | H | H |
| I.a.1287 | Cl | F | F | F | F | OCH$_3$ | H | H |
| I.a.1288 | F | Cl | F | F | F | OCH$_3$ | H | H |
| I.a.1289 | CN | F | F | F | F | OCH$_3$ | H | H |
| I.a.1290 | F | CN | F | F | F | OCH$_3$ | H | H |
| I.a.1291 | H | F | F | F | F | OCH$_3$ | H | H |
| I.a.1292 | F | F | Br | F | F | OCH$_3$ | H | H |
| I.a.1293 | F | F | C≡CH | F | F | OCH$_3$ | H | H |
| I.a.1294 | CF$_3$ | Cl | H | H | F | OCH$_3$ | H | H |
| I.a.1295 | F | F | I | F | F | OCH$_3$ | H | H |
| I.a.1296 | F | H | H | H | F | OCH$_3$ | CH$_3$ | H |
| I.a.1297 | Cl | H | H | H | F | OCH$_3$ | CH$_3$ | H |
| I.a.1298 | Br | H | H | H | F | OCH$_3$ | CH$_3$ | H |
| I.a.1299 | CN | H | H | H | F | OCH$_3$ | CH$_3$ | H |
| I.a.1300 | CH$_3$ | H | H | H | F | OCH$_3$ | CH$_3$ | H |
| I.a.1301 | F | H | H | F | F | OCH$_3$ | CH$_3$ | H |
| I.a.1302 | Cl | H | H | F | F | OCH$_3$ | CH$_3$ | H |
| I.a.1303 | F | H | H | Cl | F | OCH$_3$ | CH$_3$ | H |
| I.a.1304 | Cl | H | H | F | F | OCH$_3$ | CH$_3$ | H |
| I.a.1305 | CN | H | H | F | F | OCH$_3$ | CH$_3$ | H |
| I.a.1306 | F | H | H | CN | F | OCH$_3$ | CH$_3$ | H |
| I.a.1307 | CN | H | H | F | F | OCH$_3$ | CH$_3$ | H |
| I.a.1308 | F | H | F | H | F | OCH$_3$ | CH$_3$ | H |
| I.a.1309 | Cl | H | F | H | F | OCH$_3$ | CH$_3$ | H |
| I.a.1310 | CN | H | F | H | F | OCH$_3$ | CH$_3$ | H |
| I.a.1311 | F | F | F | H | F | OCH$_3$ | CH$_3$ | H |
| I.a.1312 | Cl | F | F | H | F | OCH$_3$ | CH$_3$ | H |
| I.a.1313 | F | Cl | F | H | F | OCH$_3$ | CH$_3$ | H |
| I.a.1314 | Cl | F | F | H | F | OCH$_3$ | CH$_3$ | H |
| I.a.1315 | CN | F | F | H | F | OCH$_3$ | CH$_3$ | H |
| I.a.1316 | F | CN | F | H | F | OCH$_3$ | CH$_3$ | H |
| I.a.1317 | CN | F | F | H | F | OCH$_3$ | CH$_3$ | H |
| I.a.1318 | F | F | H | F | F | OCH$_3$ | CH$_3$ | H |
| I.a.1319 | Cl | F | H | F | F | OCH$_3$ | CH$_3$ | H |
| I.a.1320 | F | Cl | H | F | F | OCH$_3$ | CH$_3$ | H |
| I.a.1321 | CN | F | H | F | F | OCH$_3$ | CH$_3$ | H |
| I.a.1322 | F | CN | H | F | F | OCH$_3$ | CH$_3$ | H |
| I.a.1323 | F | F | F | F | F | OCH$_3$ | CH$_3$ | H |
| I.a.1324 | Cl | F | F | F | F | OCH$_3$ | CH$_3$ | H |
| I.a.1325 | F | Cl | F | F | F | OCH$_3$ | CH$_3$ | H |
| I.a.1326 | CN | F | F | F | F | OCH$_3$ | CH$_3$ | H |
| I.a.1327 | F | CN | F | F | F | OCH$_3$ | CH$_3$ | H |
| I.a.1328 | H | F | F | F | F | OCH$_3$ | CH$_3$ | H |
| I.a.1329 | F | F | Br | F | F | OCH$_3$ | CH$_3$ | H |
| I.a.1330 | F | F | C≡CH | F | F | OCH$_3$ | CH$_3$ | H |
| I.a.1331 | CF$_3$ | Cl | H | H | F | OCH$_3$ | CH$_3$ | H |
| I.a.1332 | F | F | I | F | F | OCH$_3$ | CH$_3$ | H |
| I.a.1333 | F | H | H | H | F | OCH$_3$ | CH$_3$ | CH$_3$ |
| I.a.1334 | Cl | H | H | H | F | OCH$_3$ | CH$_3$ | CH$_3$ |
| I.a.1335 | Br | H | H | H | F | OCH$_3$ | CH$_3$ | CH$_3$ |
| I.a.1336 | CN | H | H | H | F | OCH$_3$ | CH$_3$ | CH$_3$ |
| I.a.1337 | CH$_3$ | H | H | H | F | OCH$_3$ | CH$_3$ | CH$_3$ |
| I.a.1338 | F | H | H | F | F | OCH$_3$ | CH$_3$ | CH$_3$ |
| I.a.1339 | Cl | H | H | F | F | OCH$_3$ | CH$_3$ | CH$_3$ |
| I.a.1340 | F | H | H | Cl | F | OCH$_3$ | CH$_3$ | CH$_3$ |
| I.a.1341 | Cl | H | H | F | F | OCH$_3$ | CH$_3$ | CH$_3$ |
| I.a.1342 | CN | H | H | F | F | OCH$_3$ | CH$_3$ | CH$_3$ |
| I.a.1343 | F | H | H | CN | F | OCH$_3$ | CH$_3$ | CH$_3$ |
| I.a.1344 | CN | H | H | F | F | OCH$_3$ | CH$_3$ | CH$_3$ |
| I.a.1345 | F | H | F | H | F | OCH$_3$ | CH$_3$ | CH$_3$ |
| I.a.1346 | Cl | H | F | H | F | OCH$_3$ | CH$_3$ | CH$_3$ |
| I.a.1347 | CN | H | F | H | F | OCH$_3$ | CH$_3$ | CH$_3$ |
| I.a.1348 | F | F | F | H | F | OCH$_3$ | CH$_3$ | CH$_3$ |
| I.a.1349 | Cl | F | F | H | F | OCH$_3$ | CH$_3$ | CH$_3$ |
| I.a.1350 | F | Cl | F | H | F | OCH$_3$ | CH$_3$ | CH$_3$ |

TABLE A-continued

| No. | $R^a$ | $R^b$ | $R^c$ | $R^d$ | $R^e$ | $R^2$ | $R^3$ | $R^4$ |
|---|---|---|---|---|---|---|---|---|
| I.a.1351 | Cl | F | F | H | F | OCH$_3$ | CH$_3$ | CH$_3$ |
| I.a.1352 | CN | F | F | H | F | OCH$_3$ | CH$_3$ | CH$_3$ |
| I.a.1353 | F | CN | F | H | F | OCH$_3$ | CH$_3$ | CH$_3$ |
| I.a.1354 | CN | F | F | H | F | OCH$_3$ | CH$_3$ | CH$_3$ |
| I.a.1355 | F | F | H | F | F | OCH$_3$ | CH$_3$ | CH$_3$ |
| I.a.1356 | Cl | F | H | F | F | OCH$_3$ | CH$_3$ | CH$_3$ |
| I.a.1357 | F | Cl | H | F | F | OCH$_3$ | CH$_3$ | CH$_3$ |
| I.a.1358 | CN | F | H | F | F | OCH$_3$ | CH$_3$ | CH$_3$ |
| I.a.1359 | F | CN | H | F | F | OCH$_3$ | CH$_3$ | CH$_3$ |
| I.a.1360 | F | F | F | F | F | OCH$_3$ | CH$_3$ | CH$_3$ |
| I.a.1361 | Cl | F | F | F | F | OCH$_3$ | CH$_3$ | CH$_3$ |
| I.a.1362 | F | Cl | F | F | F | OCH$_3$ | CH$_3$ | CH$_3$ |
| I.a.1363 | CN | F | F | F | F | OCH$_3$ | CH$_3$ | CH$_3$ |
| I.a.1364 | F | CN | F | F | F | OCH$_3$ | CH$_3$ | CH$_3$ |
| I.a.1365 | H | F | F | F | F | OCH$_3$ | CH$_3$ | CH$_3$ |
| I.a.1366 | F | F | Br | F | F | OCH$_3$ | CH$_3$ | CH$_3$ |
| I.a.1367 | F | F | C≡CH | F | F | OCH$_3$ | CH$_3$ | CH$_3$ |
| I.a.1368 | CF$_3$ | Cl | H | H | F | OCH$_3$ | CH$_3$ | CH$_3$ |
| I.a.1369 | F | F | I | F | F | OCH$_3$ | CH$_3$ | CH$_3$ |
| I.a.1370 | F | H | H | H | F | H | —O(CH$_2$)$_3$— | |
| I.a.1371 | Cl | H | H | H | F | H | —O(CH$_2$)$_3$— | |
| I.a.1372 | Br | H | H | H | F | H | —O(CH$_2$)$_3$— | |
| I.a.1373 | CN | H | H | H | F | H | —O(CH$_2$)$_3$— | |
| I.a.1374 | CH$_3$ | H | H | H | F | H | —O(CH$_2$)$_3$— | |
| I.a.1375 | F | H | H | F | F | H | —O(CH$_2$)$_3$— | |
| I.a.1376 | Cl | H | H | F | F | H | —O(CH$_2$)$_3$— | |
| I.a.1377 | F | H | H | Cl | F | H | —O(CH$_2$)$_3$— | |
| I.a.1378 | Cl | H | H | F | F | H | —O(CH$_2$)$_3$— | |
| I.a.1379 | CN | H | H | F | F | H | —O(CH$_2$)$_3$— | |
| I.a.1380 | F | H | H | CN | F | H | —O(CH$_2$)$_3$— | |
| I.a.1381 | CN | H | H | F | F | H | —O(CH$_2$)$_3$— | |
| I.a.1382 | F | H | F | H | F | H | —O(CH$_2$)$_3$— | |
| I.a.1383 | Cl | H | F | H | F | H | —O(CH$_2$)$_3$— | |
| I.a.1384 | CN | H | F | H | F | H | —O(CH$_2$)$_3$— | |
| I.a.1385 | F | F | F | H | F | H | —O(CH$_2$)$_3$— | |
| I.a.1386 | Cl | F | F | H | F | H | —O(CH$_2$)$_3$— | |
| I.a.1387 | F | Cl | F | H | F | H | —O(CH$_2$)$_3$— | |
| I.a.1388 | Cl | F | F | H | F | H | —O(CH$_2$)$_3$— | |
| I.a.1389 | CN | F | F | H | F | H | —O(CH$_2$)$_3$— | |
| I.a.1390 | F | CN | F | H | F | H | —O(CH$_2$)$_3$— | |
| I.a.1391 | CN | F | F | H | F | H | —O(CH$_2$)$_3$— | |
| I.a.1392 | F | F | H | F | F | H | —O(CH$_2$)$_3$— | |
| I.a.1393 | Cl | F | H | F | F | H | —O(CH$_2$)$_3$— | |
| I.a.1394 | F | Cl | H | F | F | H | —O(CH$_2$)$_3$— | |
| I.a.1395 | CN | F | H | F | F | H | —O(CH$_2$)$_3$— | |
| I.a.1396 | F | CN | H | F | F | H | —O(CH$_2$)$_3$— | |
| I.a.1397 | F | F | F | F | F | H | —O(CH$_2$)$_3$— | |
| I.a.1398 | Cl | F | F | F | F | H | —O(CH$_2$)$_3$— | |
| I.a.1399 | F | Cl | F | F | F | H | —O(CH$_2$)$_3$— | |
| I.a.1400 | CN | F | F | F | F | H | —O(CH$_2$)$_3$— | |
| I.a.1401 | F | CN | F | F | F | H | —O(CH$_2$)$_3$— | |
| I.a.1402 | H | F | F | F | F | H | —O(CH$_2$)$_3$— | |
| I.a.1403 | F | F | Br | F | F | H | —O(CH$_2$)$_3$— | |
| I.a.1404 | F | F | C≡CH | F | F | H | —O(CH$_2$)$_3$— | |
| I.a.1405 | CF$_3$ | Cl | H | H | F | H | —O(CH$_2$)$_3$— | |
| I.a.1406 | F | F | I | F | F | H | —O(CH$_2$)$_3$— | |

The azines of formula (I) according to the invention can be prepared by standard processes of organic chemistry, for example by the following processes:

Process A)

The azines of formula (I), wherein $R^1$ and $R^5$ are independently of one another H, $C_1$-$C_6$-alkyl, $C_1$-$C_6$-alkoxy-$C_1$-$C_6$-alkyl or $C_1$-$C_6$-alkoxy can be prepared by reacting biguanidines of formula (II) with carbonyl compounds of formula (III) in the presence of a base:

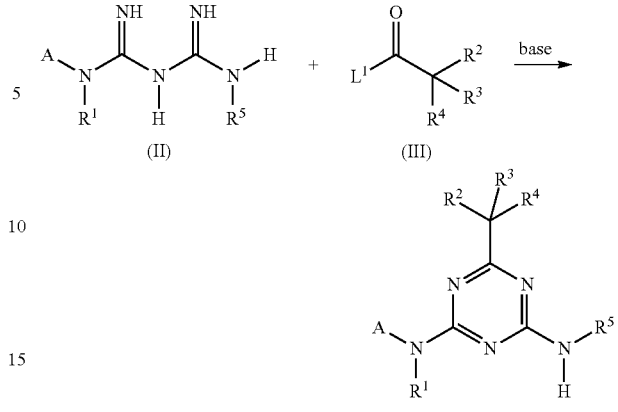

The variables A, $R^2$, $R^3$ and $R^4$ have the meanings, in particular the preferred meanings, as in formula (I) mentioned above, and $L^1$ is a nucleophilically displaceable leaving group such as halogen, CN, $C_1$-$C_6$-alkoxy, $C_1$-$C_6$-alkoxycarbonyl, $C_1$-$C_6$-alkylcarbonyloxy or $C_1$-$C_6$-alkoxycarbonyloxy;
preferably halogen or $C_1$-$C_6$-alkoxy;
particularly preferred Cl or $C_1$-$C_6$-alkoxy,
also particularly preferred halogen;
especially preferred Cl;

$R^1$ is H, $C_1$-$C_6$-alkyl, $C_1$-$C_6$-alkoxy-$C_1$-$C_6$-alkyl, $C_1$-$C_6$-alkoxy;
particularly preferred H, $C_1$-$C_6$-alkoxy-$C_1$-$C_6$-alkyl or $C_1$-$C_6$-alkoxy;
especially preferred H, CH$_2$OCH$_3$ or OCH$_3$;
more preferred hydrogen; and $R^5$ is H, $C_1$-$C_6$-alkyl, $C_1$-$C_6$-alkoxy-$C_1$-$C_6$-alkyl, $C_1$-$C_6$-alkoxy;
particularly preferred H, $C_1$-$C_6$-alkoxy-$C_1$-$C_6$-alkyl or $C_1$-$C_6$-alkoxy;
especially preferred H, CH$_2$OCH$_3$ or OCH$_3$;
more preferred hydrogen.

The reaction of biguanidines of formula (II) with carbonyl compounds of formula (III) is usually carried out at temperatures from 50° C. to the boiling point of the reaction mixture, preferably from 50° C. to 200° C. (e.g. R. Sathunuru et al., J. Heterocycl. Chem. 2008, 45, 1673-1678).

The reaction can be carried out at atmospheric pressure or under elevated pressure, if appropriate under an inert gas, continuously or batchwise.

In one embodiment of the process according to the invention, the biguanidines of formula (II) and the carbonyl compounds of formula (III) are used in equimolar amounts.

In another embodiment of the process according to the invention, the carbonyl compounds of formula (III) are used in excess with regard to the biguanidines of formula (II).

Preferably the molar ratio of the carbonyl compounds of formula (III) to the biguanidines of formula (II) is in the range from 1.5:1 to 1:1, preferably 1.2:1 to 1:1, especially preferred 1.2:1, also especially preferred 1:1.

The reaction of the biguanidines of formula (II) with the carbonyl compounds of formula (III) is carried out in an organic solvent.

Suitable in principle are all solvents which are capable of dissolving the biguanidines of formula (II) and the carbonyl compounds of formula (III) at least partly and preferably fully under reaction conditions.

Examples of suitable solvents are aliphatic hydrocarbons such as pentane, hexane, cyclohexane, nitromethane and mixtures of $C_5$-$C_8$-alkanes; romatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as defined above.

More preferred solvents are ethers as defined above.

The term solvent as used herein also includes mixtures of two or more of the above compounds.

The reaction of the biguanidines of formula (II) with the carbonyl compounds of formula (III) is carried out in the presence of a base.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines as defined above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the biguanidines of formula (II).

The end of the reaction can easily be determined by the skilled worker by means of routine methods.

The reaction mixtures are worked up in a customary manner, for example by mixing with water, separation of the phases and, if appropriate, chromatographic purification of the crude product.

Some of the intermediates and end products are obtained in the form of viscous oils, which can be purified or freed from volatile components under reduced pressure and at moderately elevated temperature.

If the intermediates and the end products are obtained as solid, purification can also be carried out by recrystallisation or digestion.

The carbonyl compounds of formula (III) required for the preparation of azines of formula (I) are known in the art or they can be prepared in accordance and/or are commercially available.

The biguanidines of formula (II) required for the preparation of azines of formula (I), wherein $R^1$ and $R^5$ are independently of one another H, $C_1$-$C_6$-alkyl, $C_1$-$C_6$-alkoxy-$C_1$-$C_6$-alkyl or $C_1$-$C_6$-alkoxy, can be prepared by reacting guanidines of formula (IV) with amines of formula (V) in the presence of an acid:

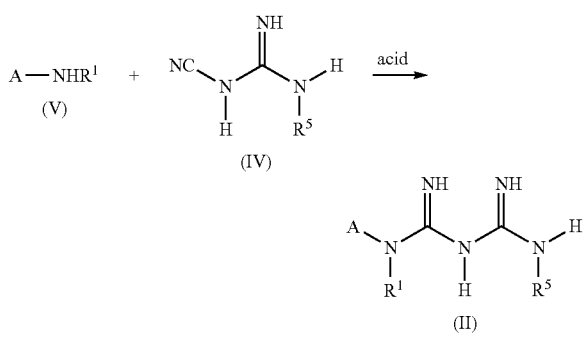

The variable A has the meanings, in particular the preferred meanings, as in formula (I) mentioned above;

$R^1$ is H, $C_1$-$C_6$-alkyl, $C_1$-$C_6$-alkoxy-$C_1$-$C_6$-alkyl, $C_1$-$C_6$-alkoxy;

particularly preferred H, $C_1$-$C_6$-alkoxy-$C_1$-$C_6$-alkyl or $C_1$-$C_6$-alkoxy;

especially preferred H, $CH_2OCH_3$ or $OCH_3$;

more preferred hydrogen; and $R^5$ is H, $C_1$-$C_6$-alkyl, $C_1$-$C_6$-alkoxy-$C_1$-$C_6$-alkyl, $C_1$-$C_6$-alkoxy;

particularly preferred H, $C_1$-$C_6$-alkoxy-$C_1$-$C_6$-alkyl or $C_1$-$C_6$-alkoxy;

especially preferred H, $CH_2OCH_3$ or $OCH_3$;

more preferred hydrogen.

The reaction of guanidines of formula (IV) with amines of formula (V) is usually carried out from 50° C. to 150° C., preferably from 80° C. to 130° C.

Microwave-Technology was used where applicable (e.g. C. O. Kappe, A. Stadler, Microwaves in Organic and Medicinal Chemistry, Weinheim 2012).

The reaction can be carried out at atmospheric pressure or under elevated pressure, if appropriate under an inert gas, continuously or batchwise.

In one embodiment of the process according to the invention, the guanidines of formula (IV) and the amines of formula (V) are used in equimolar amounts.

In another embodiment of the process according to the invention, the amines of formula (V) are used in excess with regard to the guanidines of formula (IV).

Preferably the molar ratio of the amines of formula (V) to the guanidines of formula (IV) is in the range from 2:1 to 1:1, preferably 1.5:1 to 1:1, especially preferred 1:1.

The reaction of the guanidines of formula (IV) with the amines of formula (V) is carried out in an organic solvent.

Suitable in principle are all solvents which are capable of dissolving the guanidines of formula (IV) and the amines of formula (V) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, nitriles and dipolar aprotic solvents as defined above.

More preferred solvents are nitriles as defined above.

The term solvent as used herein also includes mixtures of two or more of the above compounds.

The reaction of the guanidines of formula (IV) with the amines of formula (V) is carried out in the presence of an acid.

As acids and acidic catalysts inorganic acids like hydrofluoric acid, hydrochloric acid, hydrobromic acid, hydroiodic acid, phosphoric acid, sulfuric acid; mineral acids like hydrochloric acid, sulfuric acid, phosphoric acid, Lewis acids like boron trifluoride, aluminium chloride, ferric-III-chloride, tin-IV-chloride, titanium-IV-chloride and zinc-II-chloride, as well as organic acids like formic acid, acetic acid, propionic acid, oxalic acid, methylbenzenesulfonic acid, benzenesulfonic acid, camphorsulfonic acid, citric acid, trifluoroacetic acid, can be used.

The acids are generally employed in excess or, if appropriate, can be used as solvent.

Work up can be carried out in a known manner.

The guanidines of formula (IV) required for the preparation of biguanidines of formula (II) are commercially available or can be prepared in accordance with literature procedures (e.g. J. L. LaMattina et al., J. Med. Chem. 1990, 33, 543-552; A. Perez-Medrano et al., J. Med. Chem. 2009, 52, 3366-3376).

The amines of formula (V) required for the preparation of biguanidines of formula (II) are commercially available.

Process B)

The azines of formula (I), wherein $R^1$ and $R^5$ are independently of one another H, $C_1$-$C_6$-alkyl, $C_1$-$C_6$-alkoxy-$C_1$-$C_6$-alkyl or $C_1$-$C_6$-alkoxy, can also be prepared by reacting halotriazines of formula (VI) with amines of formula (V) in the presence of a base and a catalyst:

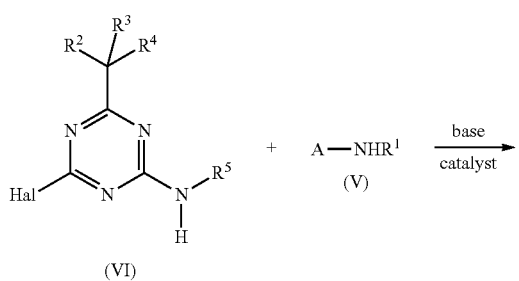

-continued

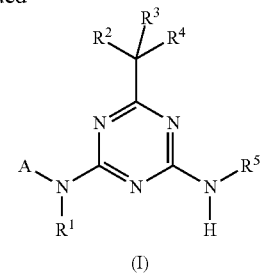

The variables A, $R^2$, $R^3$ and $R^4$ have the meanings, in particular the preferred meanings, as in formula (I) mentioned above;

Hal is halogen;
  preferably Cl or Br;
  particularly preferred Cl;
$R^1$ is H, $C_1$-$C_6$-alkyl, $C_1$-$C_6$-alkoxy-$C_1$-$C_6$-alkyl, $C_1$-$C_6$-alkoxy;
  particularly preferred H, $C_1$-$C_6$-alkoxy-$C_1$-$C_6$-alkyl or $C_1$-$C_6$-alkoxy;
  especially preferred H, $CH_2OCH_3$ or $OCH_3$;
  more preferred hydrogen; and
$R^5$ is H, $C_1$-$C_6$-alkyl, $C_1$-$C_6$-alkoxy-$C_1$-$C_6$-alkyl, $C_1$-$C_6$-alkoxy;
  particularly preferred H, $C_1$-$C_6$-alkoxy-$C_1$-$C_6$-alkyl or $C_1$-$C_6$-alkoxy;
  especially preferred H, $CH_2OCH_3$ or $OCH_3$;
  more preferred hydrogen.

The reaction of the halotriazines of formula (VI) with the amines of formula (V) is usually carried out from 50° C. to the boiling point of the reaction mixture, preferably from 50° C. to 150° C., particularly preferably from 60° C. to 100° C., in an inert organic solvent (e.g. P. Dao et al., Tetrahedron 2012, 68, 3856-3860).

The reaction can be carried out at atmospheric pressure or under elevated pressure, if appropriate, under an inert gas, continuously or batchwise.

In one embodiment of the process according to the invention, the halotriazines of formula (VI) and the amines of formula (V) are used in equimolar amounts.

In another embodiment of the process according to the invention, the amines of formula (V) are used in excess with regard to the halotriazines of formula (VI).

Preferably the molar ratio of the amines of formula (V) to the halotriazines of formula (VI) is in the range from 2:1 to 1:1, preferably 1.5:1 to 1:1, especially preferred 1.2:1.

The reaction of the halotriazines of formula (VI) with the amines of formula (V) is carried out in an organic solvent.

Suitable in principle are all solvents which are capable of dissolving the halotriazines of formula (VI) and the amines of formula (V) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers as defined above.

The term solvent as used herein also includes mixtures of two or more of the above compounds.

The reaction of the halotriazines of formula (VI) with the amines of formula (V) is carried out in the presence of a base.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal and alkaline earth metal formates, acetates and other metal salts of carboxylic acids, such as sodium formate, sodium benzoate, lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and also bicyclic amines such as 1,8-diazabicyclo[5.4.0]undec-7-ene (DBU) or 1,5-diazabicyclo[4.3.0]non-5-ene (DBN).

Preferred bases are alkali metal and alkaline earth metal alkoxides as defined above.

The term base as used herein also includes mixtures of two or more, preferably two of the above compounds. Particular preference is given to the use of one base.

The bases can be used in excess, preferably from 1 to 10, especially preferred from 2 to 4 base equivalents based on the halotriazines of formula (VI), and they may also be used as the solvent.

The reaction of the halotriazines of formula (VI) with the amines of formula (V) is carried out in the presence of a catalyst.

Examples of suitable catalysts include for example, palladium based catalysts like, for example, Palladium (II)acetate, tetrakis(triphenylphosphine)palladium(0), bis(triphenylphosphine)palladium(II)chloride or (1,1,-bis(diphenylphosphino)ferrocene)-dichloropalladium(II), and optionally suitable additives such as, for example, phosphines like, for example, P(o-tolyl)$_3$, triphenylphosphine or BINAP (2,2'-Bis(diphenylphospino)-1,1'-binaphthyl).

The amount of catalyst is usually 10 to 20 mol % (0.1 to 0.2 equivalents) based on the halotriazines of formula (VI).

The end of the reaction can easily be determined by the skilled worker by means of routine methods.

The reaction mixtures are worked up in a customary manner, for example by mixing with water, separation of the phases and, if appropriate, chromatographic purification of the crude product.

The amines of formula (V) required for the preparation of azines of formula (I), wherein $R^1$ is H, $C_1$-$C_6$-alkyl, $C_1$-$C_6$-alkoxy-$C_1$-$C_6$-alkyl or $C_1$-$C_6$-alkoxy, are commercially available and/or can be prepared by analogy to known literature.

The halotriazines of formula (VI) required for the preparation of azines of formula (I), wherein $R^5$ is H, $C_1$-$C_6$-alkyl, $C_1$-$C_6$-alkoxy-$C_1$-$C_6$-alkyl or $C_1$-$C_6$-alkoxy, are known from the literature, are commercially available and/or can be prepared by analogy (e.g. J. K. Chakrabarti et al., Tetrahedron 1975, 31, 1879-1882) by reacting thiotriazines of formula (VII) with a halogen:

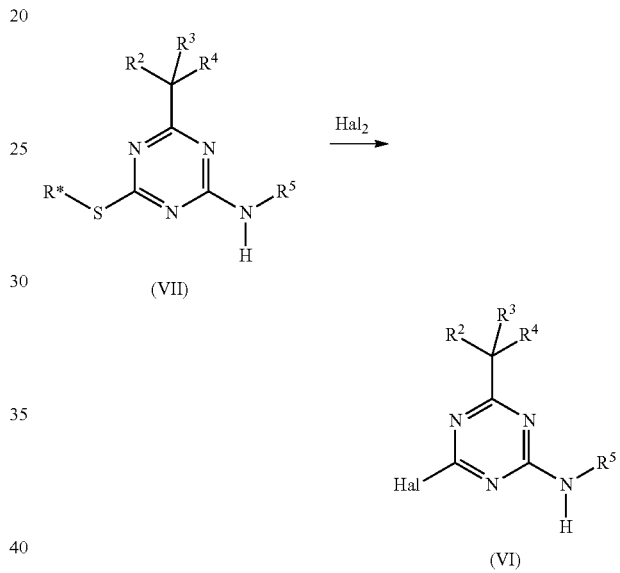

The variables $R^2$, $R^3$, and $R^4$ have the meanings, in particular the preferred meanings, as defined in formula (I) mentioned above;

Hal is halogen;
preferably Cl or Br;
particularly preferred Cl;
R* is $C_1$-$C_6$-alkyl, $C_2$-$C_6$-haloalkyl or phenyl;
preferably $C_1$-$C_6$-alkyl or $C_2$-$C_6$-haloalkyl;
particularly preferred $C_1$-$C_6$-alkyl;
especially preferred $CH_3$; and
$R^5$ is H, $C_1$-$C_6$-alkyl, $C_1$-$C_6$-alkoxy-$C_1$-$C_6$-alkyl, $C_1$-$C_6$-alkoxy;
particularly preferred H, $C_1$-$C_6$-alkoxy-$C_1$-$C_6$-alkyl or $C_1$-$C_6$-alkoxy;
especially preferred H, $CH_2OCH_3$ or $OCH_3$;
more preferred hydrogen.

The reaction of the thiotriazines of formula (VII) with the halogen is usually carried out from 0° C. to the boiling point of the reaction mixture, preferably from 15° C. to the boiling point of the reaction mixture, particularly preferably from 15° C. to 40° C., in an inert organic solvent (e.g. J. K. Chakrabarti et al., Tetrahedron 1975, 31, 1879-1882).

The reaction can be carried out at atmospheric pressure or under elevated pressure, if appropriate under an inert gas, continuously or batchwise.

In the process according to the invention, the halogen is used in excess with regard to the thiotriazines of formula (VII).

The reaction of the thiotriazines of formula (VII) with the halogen is carried out in an organic solvent.

Suitable in principle are all solvents which are capable of dissolving the thiotriazines of formula (VII) and the halogen at least partly and preferably fully under reaction conditions.

Examples of suitable solvents are aliphatic hydrocarbons such as pentane, hexane, cyclohexane and mixtures of $C_5$-$C_8$-alkanes, halogenated hydrocarbons such as dichloromethane, 1,2-dichloroethane, chloroform and carbon tetrachloride; ethers such as diethyl ether, diisopropyl ether, tert.-butyl methylether (TBME), dioxane, anisole and tetrahydrofuran (THF), alcohols such as methanol, ethanol, n-propanol, isopropanol, n-butanol and tert.-butanol, as well as organic acids like formic acid, acetic acid, propionic acid, oxalic acid, citric acid, trifluoroacetic acid.

Preferred solvents are halogenated hydrocarbons and organic acids as defined above.

The term solvent as used herein also includes mixtures of two or more of the above compounds.

The end of the reaction can easily be determined by the skilled worker by means of routine methods.

The reaction mixtures are worked up in a customary manner, for example by mixing with water, separation of the phases and, if appropriate, chromatographic purification of the crude product.

The thiotriazines of formula (VII) required for the preparation of halotriazines of formula (VI) can be prepared in accordance by reacting guanidine-salts of formula (VIII) with carbonyl compounds of formula (III) in the presence of a base:

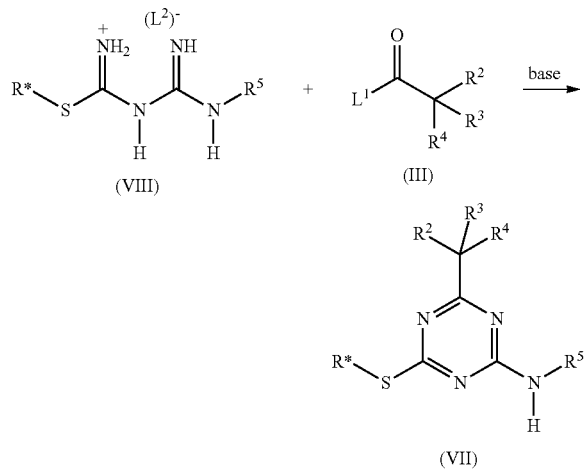

The variables $R^2$, $R^3$ and $R^4$ have the meanings, in particular the preferred meanings, as defined in formula (I) mentioned above;

R* is $C_1$-$C_6$-alkyl, $C_2$-$C_6$-haloalkyl or phenyl;
  preferably $C_1$-$C_6$-alkyl or $C_2$-$C_6$-haloalkyl;
  particularly preferred $C_1$-$C_6$-alkyl;
  especially preferred $CH_3$;

$L^1$ is a nucleophilically displaceable leaving group such as halogen, CN, $C_1$-$C_6$-alkoxy, $C_1$-$C_6$-alkoxycarbonyl, $C_1$-$C_6$-alkylcarbonyloxy or $C_1$-$C_6$-alkoxycarbonyloxy;
  preferably halogen or $C_1$-$C_6$-alkoxy;
  particularly preferred Cl or $C_1$-$C_6$-alkoxy,
  also particularly preferred halogen;
  especially preferred Cl; and $L^2$ is a nucleophilically displaceable leaving group such as halogen, $C_1$-$C_6$-alkylsulfonyloxy, $C_1$-$C_6$-haloalkylsufonyloxy, $C_1$-$C_6$-alkoxysulfonyloxy or phenylsulfonyloxy;
  preferably halogen or $C_1$-$C_6$-haloalkylsufonyloxy;
  particularly preferred halogen;
  especially preferred I; and $R^5$ is H, $C_1$-$C_6$-alkyl, $C_1$-$C_6$-alkoxy-$C_1$-$C_6$-alkyl, $C_1$-$C_6$-alkoxy;
  particularly preferred H, $C_1$-$C_6$-alkoxy-$C_1$-$C_6$-alkyl or $C_1$-$C_6$-alkoxy;
  especially preferred H, $CH_2OCH_3$ or $OCH_3$;
  more preferred hydrogen.

The reaction of the guanidine-salt of formula (VIII) with the carbonyl compound of formula (III) is usually carried out at temperatures from 50° C. to the boiling point of the reaction mixture, preferably from 50° C. to 100° C.

The reaction can be carried out at atmospheric pressure or under elevated pressure, if appropriate under an inert gas, continuously or batchwise.

In one embodiment of the process according to the invention, the guanidine-salts of formula (VIII) and the carbonyl compound of formula (III) are used in equimolar amounts.

In another embodiment of the process according to the invention, the carbonyl compound of formula (III) is used in excess with regard to the guanidine-salts of formula (VIII).

Preferably the molar ratio of the carbonyl compound of formula (III) to the guanidine-salt of formula (VIII) is in the range from 1.5:1 to 1:1, preferably 1.2:1 to 1:1, especially preferred 1.2:1, also especially preferred 1:1.

The reaction of the guanidine-salt of formula (VIII) with the carbonyl compound of formula (III) is usually carried out in an organic solvent.

Suitable in principle are all solvents which are capable of dissolving the guanidine-salt of formula (VIII) and the carbonyl compound of formula (III) at least partly and preferably fully under reaction conditions.

Examples of suitable solvents are halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), nitriles such as acetonitrile and propionitrile, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as defined above.

More preferred solvents are ethers as defined above.

The term solvent as used herein also includes mixtures of two or more of the above compounds.

The reaction of the guanidine-salts of formula (VIII) with the carbonyl compound of formula (III) is carried out in the presence of a base.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine, and also bicyclic amines such as 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines as defined above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the guanidine-salts of formula (VIII).

The end of the reaction can easily be determined by the skilled worker by means of routine methods.

The reaction mixtures are worked up in a customary manner, for example by mixing with water, separation of the phases and, if appropriate, chromatographic purification of the crude product.

The carbonyl compounds of formula (III) required for the preparation of azines of formula (I) are known from the literature. They can be prepared in accordance and/or are commercially available.

The guanidine-salt of formula (VIII), wherein $L^2$ is iodine, required for the preparation of thiotriazines of formula (VII) is known from the literature (e.g. M. Freund et al., Chem. Ber. 1901, 34, 3110-3122; H. Eilingsfeld et al., Chem. Ber. 1967, 100, 1874-1891). The guanidine-salts of formula (VIII) are commercially available and/or can be prepared in accordance with the literature cited.

Process C)

The azines of formula (I), wherein $R^5$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

can be prepared by reacting azines of formula (I), wherein $R^5$ is hydrogen with a compound of formula (IX):

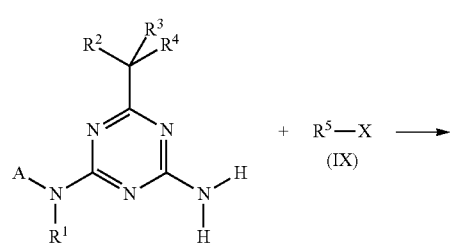

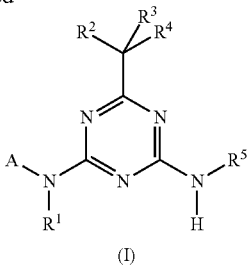

(I) wherein $R^5$ is hydrogen

The variables A, $R^1$, $R^2$, $R^3$ and $R^4$ have the meanings, in particular the preferred meanings, as in formula (I) mentioned above, $R^5$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;
  particularly preferred CN, ($C_1$-$C_6$-alkyl)carbonyl, ($C_1$-$C_6$-alkoxy)carbonyl or ($C_1$-$C_6$-alkyl)sulfonyl;
  especially preferred CN, $COCH_3$, $COOCH_3$ or $SO_2CH_3$; and X is halogen or oxycarbonyl-$C_1$-$C_6$-alkyl;
  particularly preferred halogen;
  especially preferred Cl or Br.

Process D)

The azines of formula (I), wherein $R^1$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
  wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

can be prepared by reacting azines of formula (I), wherein $R^1$ is hydrogen with a compound of formula (X):

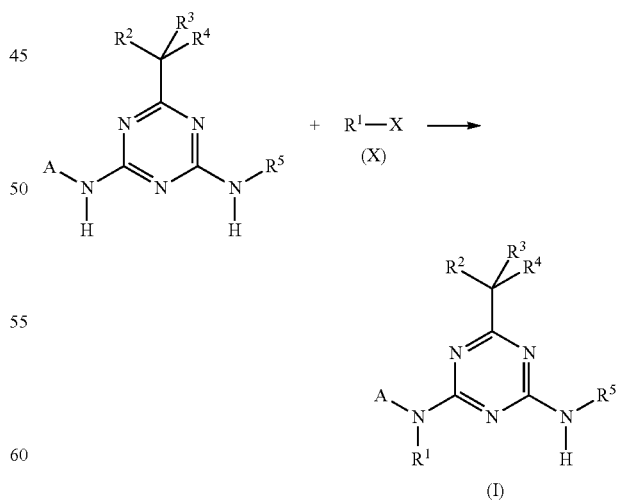

(I) wherein $R^5$ is hydrogen

The variables A, $R^2$, $R^3$, $R^4$ and $R^5$ have the meanings, in particular the preferred meanings, as in formula (I) mentioned above, R¹ is CN, (C₁-C₆-alkyl)carbonyl, (C₁-C₆-alkoxy)carbonyl, (C₁-C₆-alkyl)sulfonyl or phenylsulfonyl,
wherein the phenyl is unsubstituted or substituted by one to five substituents selected from the group consisting of halogen, CN, NO₂, C₁-C₆-alkyl, C₁-C₆-haloalkyl and C₁-C₆-alkoxy;
particularly preferred CN, (C₁-C₆-alkyl)carbonyl, (C₁-C₆-alkoxy)carbonyl or (C₁-C₆-alkyl)sulfonyl;
especially preferred CN, COCH₃, COOCH₃ or SO₂CH₃; and
X is halogen or oxycarbonyl-C₁-C₆-alkyl;
particularly preferred halogen;
especially preferred Cl or Br.

Both processes C and D independently of one another usually carried out at from 0° C. to the boiling point of the reaction mixture, preferably from 23° C. to 130° C., particularly preferably from 23° C. to 100° C., (e.g. Y. Yuki et al., Polym. J. 1992, 24, 791-799).

Both processes C and D independently of one another can be carried out at atmospheric pressure or under elevated pressure, if appropriate under an inert gas, continuously or batchwise.

In one embodiment of processes C and D according to the invention independently of one another, the azines of formula (I), wherein R⁵, or R¹ respectively, is hydrogen are used in excess with regard to the compound of formula (IX), or (X) respectively.

In another embodiment of processes C and D according to the invention independently of one another, the azines of formula (I), wherein R⁵, or R¹ respectively, is hydrogen and the compound of formula (IX), or (X) respectively, are used in equimolar amounts.

Preferably the molar ratio of the azines of formula (I), wherein R⁵, or R¹ respectively, is hydrogen to the compound of formula (IX), or (X) respectively is in the range from 1:1.5 to 1:1, preferably 1:1.2 to 1:1, especially preferred 1:1.

Both processes C and D independently of one another are carried out in an organic solvent. Suitable in principle are all solvents which are capable of dissolving the azines of formula (I), wherein R⁵, or R¹ respectively, is hydrogen and the compound of formula (IX), or (X) respectively, at least partly and preferably fully under reaction conditions.

Examples of suitable solvents are halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); nitriles such as acetonitrile and propionitrile; alcohols such as methanol, ethanol, n-propanol, isopropanol, n-butanol and tert.-butanol; organic acids like formic acid, acetic acid, propionic acid, oxalic acid, methylbenzenesulfonic acid, benzenesulfonic acid, camphorsulfonic acid, citric acid, trifluoroacetic acid as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are halogenated hydrocarbons, ethers and dipolar aprotic solvents as mentioned above.

More preferred solvents are dichloromethane or dioxane.

It is also possible to use mixtures of the solvents mentioned.

The term solvent as used herein also includes mixtures of two or more of the above compounds.

Both processes C and D independently of one another are optionally carried out in the presence of a base.

Examples of suitable bases include metal-containing bases and nitrogen-containing bases.

Examples of suitable metal-containing bases are inorganic compounds such as alkali metal and alkaline earth metal hydrides such as lithium hydride, sodium hydride, potassium hydride and calcium hydride, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-C₁-C₆-alkylamines, for example triethylamine, trimethylamine, N-ethyldiisopropylamine, and N-methylpiperidine, pyridine, substituted pyridines such as collidine, lutidine, N-methylmorpholine and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN).

Preferred bases are organic bases and alkali metal carbonates as mentioned above.

Especially preferred bases are organic bases as mentioned above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the azines of formula (I).

Work-up can be done in a known manner.

The compounds of formula (IX), or (X) respectively, are known compounds. They are commercially available or can be prepared in analogy to known methods.

The biguanidines of formula (II) are novel compounds and as shown above suitable intermediates for the preparation of the azines of formula (I) according to the present invention.

Therefore the present invention also provides biguanidines of formula (II)

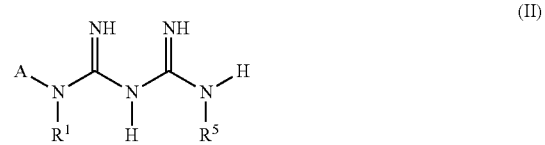

wherein
A is phenyl, which is substituted by two to five substituents selected from the group consisting of halogen, CN, NO₂, C₁-C₆-alkyl, C₁-C₆-haloalkyl, OH, C₁-C₆-alkoxy, C₁-C₆-alkylthio, (C₁-C₆-alkyl)sulfinyl, (C₁-C₆-alkyl)sulfonyl, amino, (C₁-C₆-alkyl)amino, di(C₁-C₆-alkyl)amino, (C₁-C₆-alkyl)carbonyl, (C₁-C₆-alkoxy)carbonyl;
R¹ is H, C₁-C₆-alkyl, C₁-C₆-alkoxy-C₁-C₆-alkyl, C₁-C₆-alkoxy; and
R⁵ is H, C₁-C₆-alkyl, C₁-C₆-alkoxy-C₁-C₆-alkyl, C₁-C₆-alkoxy;
including their agriculturally acceptable salts or N-oxides.

With respect to the variable A, the particularly preferred embodiments of the biguanidines of formula (II) correspond, either independently of one another or in combination with one another, to those of the variable A of the azines formula (I), and, either independently of one another or in combination with one another, $R^1$ is particularly preferred H, $C_1$-$C_6$-alkoxy-$C_1$-$C_6$-alkyl or $C_1$-$C_6$-alkoxy;
especially preferred H, $CH_2OCH_3$ or $OCH_3$;
more preferred hydrogen;

$R^5$ is particularly preferred H, $C_1$-$C_6$-alkoxy-$C_1$-$C_6$-alkyl or $C_1$-$C_6$-alkoxy;
especially preferred H, $CH_2OCH_3$ or $OCH_3$;
more preferred hydrogen.

Particular preference is given to biguanidines of formula (II.a), which correspond to biguanidines of formula (II) wherein A is (A.1) and $R^1$ and $R^5$ are H:

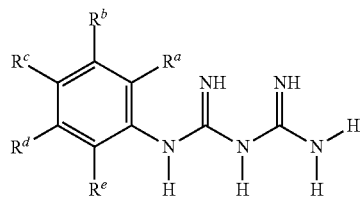

(II.a)

wherein the variables $R^a$, $R^b$, $R^c$, $R^d$ and $R^e$ have the meanings, in particular the preferred meanings, as defined above;

special preference is given to the biguanidines of the formulae (II.a.1) to (II.a.37) of Table B, where the definitions of the variables $R^a$, $R^b$, $R^c$, $R^d$, $R^e$, $R^2$, $R^3$ and $R^4$ are of particular importance for the compounds according to the invention not only in combination with one another but in each case also on their own:

TABLE B

| No. | $R^a$ | $R^b$ | $R^c$ | $R^d$ | $R^e$ |
|---|---|---|---|---|---|
| II.a.1 | F | H | H | H | F |
| II.a.2 | Cl | H | H | H | F |
| II.a.3 | Br | H | H | H | F |
| II.a.4 | CN | H | H | H | F |
| II.a.5 | $CH_3$ | H | H | H | F |
| II.a.6 | F | H | H | F | F |
| II.a.7 | Cl | H | H | F | F |
| II.a.8 | F | H | H | Cl | F |
| II.a.9 | Cl | H | H | F | F |
| II.a.10 | CN | H | H | F | F |
| II.a.11 | F | H | H | CN | F |
| II.a.12 | CN | H | H | F | F |
| II.a.13 | F | H | F | H | F |
| II.a.14 | Cl | H | F | H | F |
| II.a.15 | CN | H | F | H | F |
| II.a.16 | F | F | F | H | F |
| II.a.17 | Cl | F | F | H | F |
| II.a.18 | F | Cl | F | H | F |
| II.a.19 | Cl | F | F | H | F |
| II.a.20 | CN | F | F | H | F |
| II.a.21 | F | CN | F | H | F |
| II.a.22 | CN | F | F | H | F |
| II.a.23 | F | F | F | F | F |
| II.a.24 | Cl | F | F | F | F |
| II.a.25 | F | Cl | H | F | F |
| II.a.26 | CN | F | H | F | F |
| II.a.27 | F | CN | H | F | F |
| II.a.28 | F | F | F | F | F |
| II.a.29 | Cl | F | F | F | F |
| II.a.30 | F | Cl | F | F | F |
| II.a.31 | CN | F | F | F | F |
| II.a.32 | F | CN | F | F | F |
| II.a.33 | H | F | F | F | F |
| II.a.34 | F | F | Br | F | F |
| II.a.35 | F | F | C≡CH | F | F |
| II.a.36 | $CF_3$ | Cl | H | H | F |
| II.a.37 | F | F | I | F | F |

Particular preference is given to the biguanidines of formulae (II.a.1), (II.a.4), (II.a.9), (II.a.23) and (II.a.28) as defined above;
special preference is given to the biguanidines of formulae (II.a.1), (II.a.4), (II.a.23) and (II.a.28) as defined above;
more preference is given to the biguanidines of formulae (II.a.23) and (II.a.28) as defined above.

The halotriazines of formula (VI) are novel compounds and as shown above suitable intermediates for the preparation of the azines of formula (I) according to the present invention.

Therefore the present invention also provides halotriazines of formula (VI)

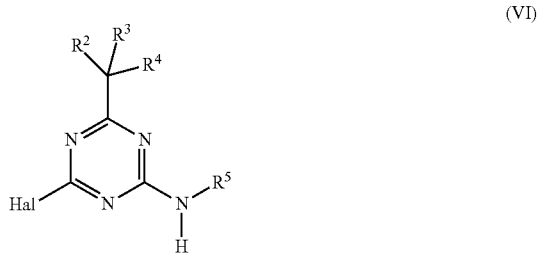

(VI)

wherein
$R^2$ is H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;
$R^3$ is H, halogen, CN, $C_1$-$C_6$-alkyl, $C_1$-$C_6$-haloalkyl or $C_1$-$C_6$-alkoxy;
$R^4$ is H, halogen, CN, $C_1$-$C_6$-alkyl or $C_1$-$C_6$-haloalkyl; or
$R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
wherein the $C_3$-$C_6$-cycloalkyl, $C_3$-$C_6$-cycloalkenyl or three- to six-membered heterocyclyl is unsubstituted or substituted by one to three substituents selected from halogen, CN, $C_1$-$C_6$-alkyl and $C_1$-$C_6$-alkoxy; and
$R^5$ is H, $C_1$-$C_6$-alkyl, $C_1$-$C_6$-alkoxy-$C_1$-$C_6$-alkyl, $C_1$-$C_6$-alkoxy; and
Hal is halogen;
including their agriculturally acceptable salts or N-oxides.

With respect to the variables $R^2$, $R^3$ and $R^4$, the particularly preferred embodiments of the thiotriazines of formula (VII) correspond, either independently of one another or in combination with one another, to those of the variables of $R^2$, $R^3$ and $R^4$ of the azines formula (I), and, either independently of one another or in combination with one another, $R^5$ is particularly preferred H, $C_1$-$C_6$-alkoxy-$C_1$-$C_6$-alkyl or $C_1$-$C_6$-alkoxy;
especially preferred H, $CH_2OCH_3$ or $OCH_3$;
more preferred hydrogen;
Hal is preferably Cl or Br;
particularly preferred Cl.

Preference is given to the halotriazines of formula (VI.a), which correspond to the halotriazines of formula (VI) wherein $R^5$ is hydrogen and Hal is Cl:

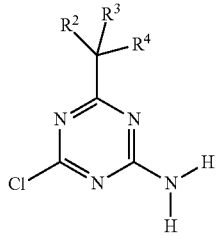

(VI.a)

wherein the variables $R^2$, $R^3$ and $R^4$ have the meanings, in particular the preferred meanings, as defined above;

special preference is given to the halotriazines of formulae (VI.a.1) to (VI.a.38) of Table C, where the definitions of the variables $R^2$, $R^3$ and $R^4$ are of particular importance for the compounds according to the invention not only in combination with one another but in each case also on their own:

TABLE C

| No. | $R^2$ | $R^3$ | $R^4$ |
|---|---|---|---|
| VI.a.1 | $CH_3$ | H | H |
| VI.a.2 | $CH_3$ | $CH_3$ | H |
| VI.a.3 | $CH_3$ | $CH_3$ | $CH_3$ |
| VI.a.4 | F | F | F |
| VI.a.5 | F | $CF_3$ | F |
| VI.a.6 | F | $CH_3$ | F |
| VI.a.7 | F | $CH_3$ | H |
| VI.a.8 | F | $CH_3$ | $CH_3$ |
| VI.a.9 | Cl | $CH_3$ | $CH_3$ |
| VI.a.10 | F | $C_2H_5$ | $CH_3$ |
| VI.a.11 | F | $C_2H_5$ | $C_2H_5$ |
| VI.a.12 | H |  | —$(CH_2)_2$— |
| VI.a.13 | H |  | —$(CH_2)_3$— |
| VI.a.14 | H |  | —$(CH_2)_4$— |
| VI.a.15 | H |  | —$(CH_2)_5$— |
| VI.a.16 | $CH_3$ |  | —$(CH_2)_2$— |
| VI.a.17 | $CH_3$ |  | —$(CH_2)_3$— |
| VI.a.18 | $CH_3$ |  | —$(CH_2)_4$— |
| VI.a.19 | $CH_3$ |  | —$(CH_2)_5$— |
| VI.a.20 | F |  | —$(CH_2)_2$— |
| VI.a.21 | F |  | —$(CH_2)_3$— |
| VI.a.22 | F |  | —$(CH_2)_4$— |
| VI.a.23 | F |  | —$(CH_2)_5$— |
| VI.a.24 | Cl |  | —$(CH_2)_2$— |
| VI.a.25 | Cl |  | —$(CH_2)_3$— |
| VI.a.26 | Cl |  | —$(CH_2)_4$— |
| VI.a.27 | Cl |  | —$(CH_2)_5$— |
| VI.a.28 | $C_2H_5$ | $CH_3$ | H |
| VI.a.29 | $C_2H_5$ | $C_2H_5$ | H |
| VI.a.30 | $C_2H_5$ | $C_2H_5$ | $CH_3$ |
| VI.a.31 | $C_2H_5$ | $CH_3$ | $CH_3$ |
| VI.a.32 | Cl | $CH_3$ | H |
| VI.a.33 | $CH_2Cl$ | Cl | $CH_3$ |
| VI.a.34 | CN | $CH_3$ | $CH_3$ |
| VI.a.35 | $OCH_3$ | H | H |
| VI.a.36 | $OCH_3$ | $CH_3$ | H |
| VI.a.37 | $OCH_3$ | $CH_3$ | $CH_3$ |
| VI.a.38 | H |  | —$O(CH_2)_3$— |

Also preferred are the halotriazines of formula (VI.b), particularly preferred the halotriazines of formulae (VI.b.1) to (VI.b.27), which differ from the corresponding halotriazines of formulae (VI.a.1) to (VI.a.27) only in that Hal is Br:

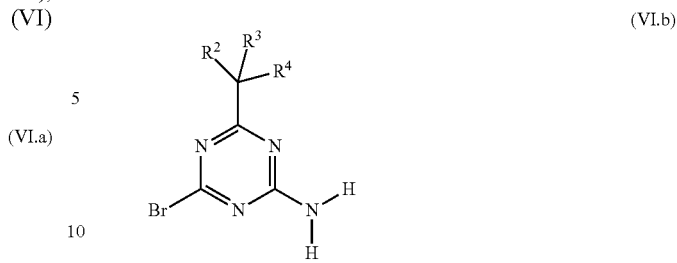

(VI.b)

Particular preference is given to the halotriazines of formulae (VI.a.2), (VI.a.3), (VI.a.6), (VI.a.8), (VI.a.9), (VI.a.14) and (VI.a.15) as defined above;

special preference is given to the halotriazines of formulae (VI.a.2), (VI.a.3), (VI.a.8), (VI.a.9) as defined above;

more preference is given to the halotriazine of formula (VI.a.8) as defined above.

The thiotriazines of formula (VII) are novel compounds and as shown above suitable intermediates for the preparation of the azines of formula (I) according to the present invention.

Therefore the present invention also provides thiotriazines of formula (VII)

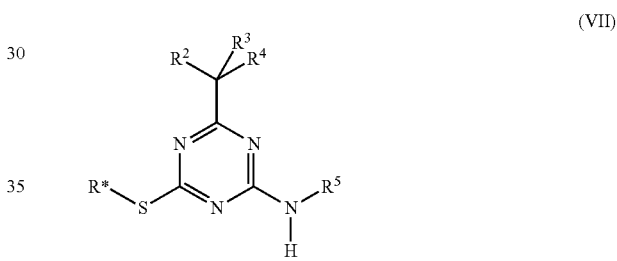

(VII)

wherein
$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;
$R^3$ H, halogen, CN, $C_1$-$C_6$-alkyl, $C_1$-$C_6$-haloalkyl or $C_1$-$C_6$-alkoxy;
$R^4$ H, halogen, CN, $C_1$-$C_6$-alkyl or $C_1$-$C_6$-haloalkyl; or
$R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
wherein the $C_3$-$C_6$-cycloalkyl, $C_3$-$C_6$-cycloalkenyl or three- to six-membered heterocyclyl is unsubstituted or substituted by one to three substituents selected from halogen, CN, $C_1$-$C_6$-alkyl and $C_1$-$C_6$-alkoxy; and
$R^5$ is H, $C_1$-$C_6$-alkyl, $C_1$-$C_6$-alkoxy-$C_1$-$C_6$-alkyl, $C_1$-$C_6$-alkoxy; and
R* is $C_1$-$C_6$-alkyl, $C_2$-$C_6$-haloalkyl or phenyl;
including their agriculturally acceptable salts or N-oxides.

With respect to the variables $R^2$, $R^3$ and $R^4$, the particularly preferred embodiments of the thiotriazines of formula (VII) correspond, either independently of one another or in combination with one another, to those of the variables of $R^2$, $R^3$ and $R^4$ of the azines formula (I), and, either independently of one another or in combination with one another, $R^5$ is particularly preferred H, $C_1$-$C_6$-alkoxy-$C_1$-$C_6$-alkyl or $C_1$-$C_6$-alkoxy;
especially preferred H, $CH_2OCH_3$ or $OCH_3$;
more preferred hydrogen;
R* is preferably $C_1$-$C_6$-alkyl or $C_2$-$C_6$-haloalkyl;
particularly preferred $C_1$-$C_6$-alkyl;
especially preferred $CH_3$.

Preference is given to the thiotriazines of formula (VII.a), which correspond to the thiotriazines of formula (VII) wherein $R^5$ is hydrogen and R* is methyl:

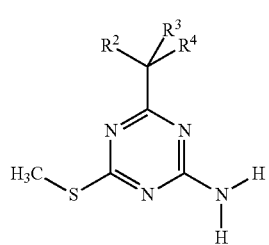

(VII.a)

wherein the variables $R^2$, $R^3$ and $R^4$ have the meanings, in particular the preferred meanings, as defined above;
special preference is given to the thiotriazines of formulae (VII.a.1) to (VII.a.38) of Table D, where the definitions of the variables $R^2$, $R^3$ and $R^4$ are of particular importance for the compounds according to the invention not only in combination with one another but in each case also on their own:

TABLE D

| No. | $R^2$ | $R^3$ | $R^4$ |
|---|---|---|---|
| VII.a.1 | $CH_3$ | H | H |
| VII.a.2 | $CH_3$ | $CH_3$ | H |
| VII.a.3 | $CH_3$ | $CH_3$ | $CH_3$ |
| VII.a.4 | F | F | F |
| VII.a.5 | F | $CF_3$ | F |
| VII.a.6 | F | $CH_3$ | F |
| VII.a.7 | F | $CH_3$ | H |
| VII.a.8 | F | $CH_3$ | $CH_3$ |
| VII.a.9 | Cl | $CH_3$ | $CH_3$ |
| VII.a.10 | F | $C_2H_5$ | $CH_3$ |
| VII.a.11 | F | $C_2H_5$ | $C_2H_5$ |
| VII.a.12 | H | —$(CH_2)_2$— | |
| VII.a.13 | H | —$(CH_2)_3$— | |
| VII.a.14 | H | —$(CH_2)_4$— | |
| VII.a.15 | H | —$(CH_2)_5$— | |
| VII.a.16 | $CH_3$ | —$(CH_2)_2$— | |
| VII.a.17 | $CH_3$ | —$(CH_2)_3$— | |
| VII.a.18 | $CH_3$ | —$(CH_2)_4$— | |
| VII.a.19 | $CH_3$ | —$(CH_2)_5$— | |
| VII.a.20 | F | —$(CH_2)_2$— | |
| VII.a.21 | F | —$(CH_2)_3$— | |
| VII.a.22 | F | —$(CH_2)_4$— | |
| VII.a.23 | F | —$(CH_2)_5$— | |
| VII.a.24 | Cl | —$(CH_2)_2$— | |
| VII.a.25 | Cl | —$(CH_2)_3$— | |
| VII.a.26 | Cl | —$(CH_2)_4$— | |
| VII.a.27 | Cl | —$(CH_2)_5$— | |
| VII.a.28 | $C_2H_5$ | $CH_3$ | H |
| VII.a.29 | $C_2H_5$ | $C_2H_5$ | H |
| VII.a.30 | $C_2H_5$ | $C_2H_5$ | $CH_3$ |
| VII.a.31 | $C_2H_5$ | $CH_3$ | $CH_3$ |
| VII.a.32 | Cl | $CH_3$ | H |
| VII.a.33 | $CH_2Cl$ | Cl | $CH_3$ |
| VII.a.34 | CN | $CH_3$ | $CH_3$ |
| VII.a.35 | $OCH_3$ | H | H |
| VII.a.36 | $OCH_3$ | $CH_3$ | H |
| VII.a.37 | $OCH_3$ | $CH_3$ | $CH_3$ |
| VII.a.38 | H | —$O(CH_2)_3$— | |

Particular preference is given to the thiotriazines of formulae (VII.a.2), (VII.a.3), (VII.a.6), (VII.a.8), (VII.a.9), (VII.a.14) and (VII.a.15) as defined above;
special preference is given to the thiotriazines of formulae (VII.a.2), (VII.a.3), (VII.a.8), (VII.a.9) as defined above;
more preference is given to the thiotriazine of formula (VII.a.8) as defined above.

To widen the spectrum of action and to achieve synergistic effects, the azines of formula (I) may be mixed with a large number of representatives of other herbicidal or growth-regulating active ingredient groups and then applied concomitantly.

Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the azines of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

The invention also relates to agrochemical compositions comprising at least an auxiliary and at least one azine of formula (I) according to the invention.

An agrochemical composition comprises a pesticidally effective amount of an azine of formula (I). The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific azine of formula (I) used.

The azines of formula (I), their N-oxides or salts can be converted into customary types of agrochemical compositions, e.g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, 6$^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinyl-alcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidally activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-Soluble Concentrates (SL, LS)

10-60 wt % of an azine of formula (I) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of an azine of formula (I) according to the invention and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of an azine of formula (I) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of an azine of formula (I) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of an azine of formula (I) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of an azine of formula (I) according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of an azine of formula (I) according to the invention are ground in a rotorstator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of an azine of formula (I) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of an azine of formula (I) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of an azine of formula (I) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of an azine of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of an azine of formula (I) according to the invention are ground finely and mixed intimately with solid carrier (e.g. finely divided kaolin) ad 100 wt %.

x) Granules (GR, FG)

0.5-30 wt % of an azine of formula (I) according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of an azine of formula (I) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of the azines of formula (I). The azines of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying azines of formula (I) or agrochemical compositions thereof, on to plant propagation material, especially seeds, include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the azines of formula (I) or the agrochemical compositions comprising them as premix or, if appropriate not until immediately prior to use (tank mix). These agents can be admixed with the agrochemical compositions according to the invention in a weight ratio of 1:100 to 100:1, preferably 1:10 to 10:1.

The user applies the azines of formula (I) according to the invention or the agrochemical compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e.g. components comprising azines of formula (I) may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g components comprising azines of formula (I), can be applied jointly (e.g. after tank mix) or consecutively.

The azines of formula (I), are suitable as herbicides. They are suitable as such or as an appropriately formulated composition (agrochemical composition).

The azines of formula (I), or the agrochemical compositions comprising the azines of formula (I), control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

The azines of formula (I), or the agrochemical compositions comprising them, are applied to the plants mainly by spraying the leaves or are applied to the soil in which the plant seeds have been sown. Here, the application can be carried out using, for example, water as carrier by customary spraying techniques using spray liquor amounts of from about 100 to 1000 l/ha (for example from 300 to 400 l/ha). The azines of formula (I), or the agrochemical compositions comprising them, may also be applied by the low-volume or the ultra-low-volume method, or in the form of microgranules.

Application of the azines of formula (I), or the agrochemical compositions comprising them, can be done before, during and/or after the emergence of the undesirable plants.

The azines of formula (I), or the agrochemical compositions comprising them, can be applied pre-, post-emergence or pre-plant, or together with the seed of a crop plant. It is also possible to apply the azines of formula (I), or the agrochemical compositions comprising them, by applying seed, pretreated with the azines of formula (I), or the agrochemical compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the azines of formula (I), or the agrochemical compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the azines of formula (I), or the agrochemical compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the azines of formula (I), without formulation auxiliaries, are, depending on the kind of effect desired, from 0.001 to 2 kg per ha, preferably from 0.005 to 2 kg per ha, more preferably from 0.005 to 0.9 kg per ha and in particular from 0.05 to 0.5 kg per ha.

In another embodiment of the invention, the application rate of the azines of formula (I) is from 0.001 to 3 kg/ha, preferably from 0.005 to 2.5 kg/ha, of active substance (a.s.).

In another preferred embodiment of the invention, the rates of application of the azines of formula (I) according to the present invention (total amount of azine of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the azines of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the azines of formula (I) is 0.1 to 1000 g/ha, preferably 1 to 750 g/ha, more preferably 5 to 500 g/ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. the azines of formula (I) are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Depending on the application method in question, the azines of formula (I), or the agrochemical compositions comprising them, can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseo-*

*lus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticum aestivum, Triticale, Triticum durum, Vicia faba, Vitis vinifera* and *Zea mays*.

Preferred crops are *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum*, (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), *Triticale, Triticum aestivum, Triticum durum, Vicia faba, Vitis vinifera* and *Zea mays*.

Especially preferred crops are crops of cereals, corn, soybeans, rice, oilseed rape, cotton, potatoes, peanuts or permanent crops.

The azines of formula (I) according to the invention, or the agrochemical compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e.g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e.g., Clearfield® summer rape (Canola, BASF SE, Germany) being tolerant to imidazolinones, e.g., imazamox, or ExpressSun® sunflowers (DuPont, USA) being tolerant to sulfonyl ureas, e.g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e.g., CryIA(b), CryIA(c), CryIF, CryIF(a2), CryIIA(b), CryIIIA, CryIIIB(b1) or Cry9c; vegetative insecticidal proteins (VIP), e.g., VIP1, VIP2, VIP3 or VIP3A; insecticidal proteins of bacteria colonizing nematodes, e.g., *Photorhabdus* spp. or *Xenorhabdus* spp.; toxins produced by animals, such as scorpion toxins, arachnid toxins, wasp toxins, or other insect-specific neurotoxins; toxins produced by fungi, such as *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e.g., WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g., Agrisure® CB) and Bt176 from Syngenta Seeds SAS, France, (corn cultivars producing the CryIAb toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e.g., potato culti-vars, which express resistance genes acting against *Phytophthora infestans* derived from the Mexican wild potato, *Solanum* bulbocastanum) or T4-lyso-zym (e.g., potato cultivars capable of synthesizing these proteins with increased resistance against bacteria such as *Erwinia amylovora*). The methods for producing such genetically modi-fied plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e.g., oil crops that produce health-promoting long-chain omega-3 fatty acids or unsaturated omega-9 fatty acids (e.g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

The preparation of the azines of formula (I) is illustrated by examples; however, the subject matter of the present invention is not limited to the examples given.

A PREPARATION EXAMPLES

Example 1

6-(1-chloro-1-methyl-ethyl)-N4-(2,3,4,5,6-pentafluorophenyl)-1,3,5-triazine-2,4-diamine

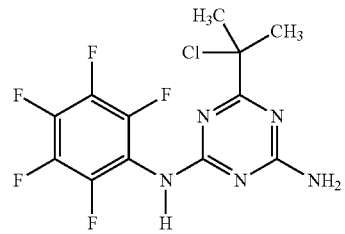 [SMILES: CC(C)(Cl)c1nc(N)nc(Nc2c(F)c(F)c(F)c(F)c2F)n1]

1.1: 1-Carbamimidoyl-3-(2,3,4,5,6-pentafluorophenyl)guanidine

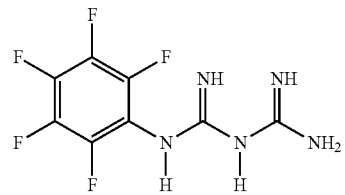 [SMILES: N=C(N)NC(=N)Nc1c(F)c(F)c(F)c(F)c1F]

A suspension of 2,3,4,5,6-pentafluoroaniline (2.00 g, 10.9 mmol) and 1-cyanoguanidine (1.10 g, 11.9 mmol) in a mixture of acetonitrile and aq. hydrochloride (38% w/w) were heated to 150° C. for 2 h in a microwave reactor. The resulting mixture was carefully added to aq. NaHCO$_3$, ethyl acetate was added and the phases were separated. The organic phase was dried over anhydrous Na$_2$SO$_4$, filtered and concentrated under reduced pressure yielding the title compound as a colorless solid (0.97 g, 33.2% yield).

MS (ESI) m/z=268.1 [M+H$^+$]

$^1$H NMR (400 MHz, d$_6$-DMSO): δ=6.75 (br s, 4H), 5.47 (s, 2H) ppm.

1.2: 6-(1-Chloro-1-methyl-ethyl)-N4-(2,3,4,5,6-pentafluorophenyl)-1,3,5-triazine-2,4-diamine 2-chloro-2-methyl-propanoyl chloride (0.69 g, 4.89 mmol) was added to a solution of 1-carbamimidoyl-3-(2,3,4,5,6-pentafluorophenyl)guanidine (1.31 g, 4.89 mmol) in a mixture of THF and triethylamine (1.49 g, 14.7 mmol). The resulting reaction mixture was heated to 60° C. for 4 h, cooled to ambient temperature and diluted with water and ethyl acetate. The phases were separated and the organic phase was dried over anhydrous Na$_2$SO$_4$, filtered and concentrated under reduced pressure. Column chromatography of the resulting crude product (ISCO-CombiFlash Rf, cyclohexane/ethyl acetate) yielded the desired title compound as colorless solid (0.72 g, 41.8% yield).

MS (ESI) m/z=354.2 [M+H$^+$].

$^1$H NMR (400 MHz, H$_3$COD): δ=1.85 (s, 6H) ppm.

Example 2

6-(1-Fluoro-1-methyl-ethyl)-N4-(2,3,5,6-tetrafluorophenyl)-1,3,5-triazine-2,4-diamine

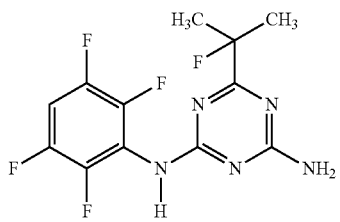 [SMILES: CC(C)(F)c1nc(N)nc(Nc2c(F)c(F)cc(F)c2F)n1]

2.1: 4-(1-fluoro-1-methyl-ethyl)-6-methylsulfanyl-1,3,5-triazin-2-amine

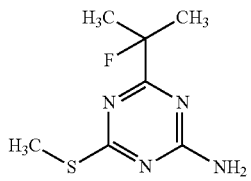

2-Fluoro-2-methyl-propanoyl chloride (23.0 g, 0.18 mol) and triethylamine (93.4 g, 0.92 mol) were added to a solution of 1-carbamimidoyl-2-methyl-isothiourea hydroiodide (48.0 g, 0.18 mol) in THF via two addition funnels. After the initial weak exothermic reaction was finished, the mixture was stirred for 3 h at 50° C. The reaction mixture was cooled to ambient temperature, diluted with water and ethyl acetate and the phases were separated. The organic phase was dried over anhydrous Na$_2$SO$_4$, filtered and concentrated under reduced pressure yielding the title compound as a colorless solid (33.3 g, 89.2% yield).

MS (ESI) m/z 203.3 [M+H$^+$]
$^1$H NMR (400 MHz, CDCl$_3$): δ=6.82 (brs, 1H), 5.64 (brs, 1H), 1.63 (d, J=21.0 Hz, 6H) ppm.

2.2: 4-chloro-6-(1-fluoro-1-methyl-ethyl)-1,3,5-triazin-2-amine

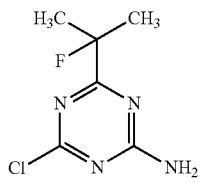

4-(1-fluoro-1-methyl-ethyl)-6-methylsulfanyl-1,3,5-triazin-2-amine (65.0 g, 0.32 mol) was dissolved in acetic acid and Cl$_2$ gas was bubbled through the solution for 30 min. The reaction mixture was stirred for an additional hour at ambient temperature and was then carefully added to a cold solution of NaOH (130 g) in water (1 L). Ethyl acetate was added and the phases were separated. The organic phase was dried over anhydrous Na$_2$SO$_4$, filtered and concentrated under reduced pressure yielding the title compound as a colorless solid (41.3 g, 67.4% yield).

MS (ESI) m/z 191.3 [M+H$^+$]
$^1$H NMR (400 MHz, CDCl$_3$): δ=7.12 (brs, 1H), 6.32 (brs, 1H), 1.69 (d, J=21.8 Hz, 6H) ppm.

2.3: 6-(1-fluoro-1-methyl-ethyl)-N4-(2,3,5,6-tetrafluorophenyl)-1,3,5-triazine-2,4-diamine

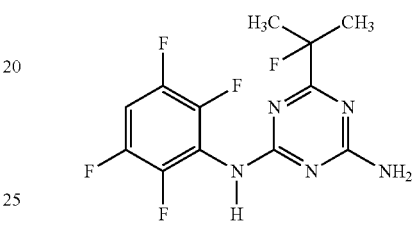

A solution of 4-chloro-6-(1-fluoro-1-methyl-ethyl)-1,3,5-triazin-2-amine (0.64 g, 2.83 mmol), 2,3,5,6-tetrafluoroaniline (0.51 g 3.11 mmol), Pd(dppf)Cl$_2$ (0.21 g, 0.28 mmol) and KOtBu (0.95 g, 8.50 mmol) in dioxane was heated to 100° C. for 16 h. The reaction mixture was cooled to ambient temperature, diluted with water and ethyl acetate and the phases were separated. The organic phase was dried over anhydrous Na$_2$SO$_4$, filtered and concentrated under reduced pressure. Column chromatography of the resulting crude product (ISCO-CombiFlash Rf, cyclohexane/ethyl acetate) yielded the title compound as colorless solid (0.30 g, 31.9% yield).

MS (ESI) m/z 320.0 [M+H$^+$].
$^1$H NMR (400 MHz, H$_3$COD): δ=7.42-7.29 (m, 1H), 1.61 (d, J=21.5 Hz, 6H) ppm.

The compounds listed below in tables 1 and 2 (examples 3 to 311) have been prepared similarly to the examples mentioned above:

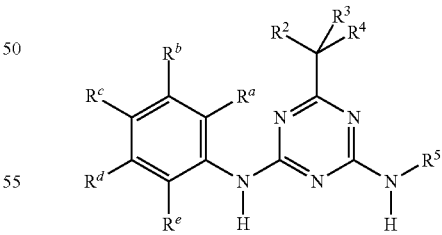

I wherein A is A.1 and
R$^1$ is H

TABLE 1

| no | R$^a$ | R$^b$ | R$^c$ | R$^d$ | R$^e$ | R$^2$ | R$^3$ | R$^4$ | R$^5$ | MS |
|---|---|---|---|---|---|---|---|---|---|---|
| 3 | F | F | F | F | F | H | H | H | H | 292.0 |
| 4 | F | F | F | F | F | H | H | CH$_3$ | H | 305.9 |

TABLE 1-continued

| no | $R^a$ | $R^b$ | $R^c$ | $R^d$ | $R^e$ | $R^2$ | $R^3$ | $R^4$ | $R^5$ | MS |
|---|---|---|---|---|---|---|---|---|---|---|
| 5 | F | F | F | F | F | H | $CH_3$ | CN | H | 331.3 |
| 6 | F | F | H | F | F | H | $CH_3$ | $CH_3$ | H | 301.9 |
| 7 | F | F | F | F | F | H | $CH_3$ | $CH_3$ | H | 320.2 |
| 8 | F | F | H | F | F | F | F | $CH_3$ | H | 323.9 |
| 9 | F | F | F | F | F | F | F | $CH_3$ | H | 342.2 |
| 10 | F | H | F | H | H | F | $CH_3$ | H | H | 270.3 |
| 11 | F | H | H | H | F | F | $CH_3$ | H | H | 270.1 |
| 12 | F | H | H | F | F | F | $CH_3$ | H | H | 270.2 |
| 13 | H | F | H | F | H | F | $CH_3$ | H | H | 270.0 |
| 14 | F | F | F | H | H | F | $CH_3$ | H | H | 288.2 |
| 15 | F | H | F | F | H | F | $CH_3$ | H | H | 288.2 |
| 16 | H | F | F | F | H | F | $CH_3$ | H | H | 288.2 |
| 17 | F | F | H | F | F | F | $CH_3$ | H | H | 306.2 |
| 18 | F | F | F | F | F | F | $CH_3$ | H | H | 324.1 |
| 19 | F | H | Br | H | F | F | $CH_3$ | H | H | 349.9 |
| 20 | F | F | F | H | Br | F | $CH_3$ | H | H | 368.1 |
| 21 | H | $CF_3$ | H | $CF_3$ | H | F | $CH_3$ | H | H | 370.2 |
| 22 | F | H | F | H | H | F | $CH_3$ | $CH_3$ | H | 284.2 |
| 23 | F | H | H | F | H | F | $CH_3$ | $CH_3$ | H | 284.2 |
| 24 | F | H | H | H | F | F | $CH_3$ | $CH_3$ | H | 284.3 |
| 25 | H | F | H | F | H | F | $CH_3$ | $CH_3$ | H | 284.0 |
| 26 | F | F | F | H | H | F | $CH_3$ | $CH_3$ | H | 302.2 |
| 27 | F | F | H | H | F | F | $CH_3$ | $CH_3$ | H | 302.3 |
| 28 | F | H | F | F | F | F | $CH_3$ | $CH_3$ | H | 302.2 |
| 29 | H | F | F | F | H | F | $CH_3$ | $CH_3$ | H | 302.2 |
| 30 | F | F | F | F | F | F | $CH_3$ | $CH_3$ | H | 338.1 |
| 31 | F | H | H | H | Br | F | $CH_3$ | $CH_3$ | H | 344.1 |
| 32 | F | Cl | H | H | F | F | $CH_3$ | $CH_3$ | H | 317.9 |
| 33 | F | H | Br | H | F | F | $CH_3$ | $CH_3$ | H | 364.1 |
| 34 | F | F | F | H | Br | F | $CH_3$ | $CH_3$ | H | 382.1 |
| 35 | Cl | H | H | H | H | F | $CH_3$ | $CH_3$ | H | 300.3 |
| 36 | Cl | F | H | H | F | F | $CH_3$ | $CH_3$ | H | 318.1 |
| 37 | F | H | CN | H | H | F | $CH_3$ | $CH_3$ | H | 291.3 |
| 38 | F | H | H | H | CN | F | $CH_3$ | $CH_3$ | H | 291.3 |
| 39 | F | H | $NO_2$ | H | H | F | $CH_3$ | $CH_3$ | H | 311.2 |
| 40 | F | $CH_3$ | H | H | F | F | $CH_3$ | $CH_3$ | H | 298.0 |
| 41 | F | H | H | H | $CH_3$ | F | $CH_3$ | $CH_3$ | H | 280.2 |
| 42 | F | H | H | H | $OCH_3$ | F | $CH_3$ | $CH_3$ | H | 296.3 |
| 43 | F | $OCH_3$ | H | H | F | F | $CH_3$ | $CH_3$ | H | 314.0 |
| 44 | F | $OC_2H_5$ | H | H | F | F | $CH_3$ | $CH_3$ | H | 328.3 |
| 45 | F | H | $SCH_3$ | H | H | F | $CH_3$ | $CH_3$ | H | 312.2 |
| 46 | H | $CF_3$ | H | $CF_3$ | H | F | $CH_3$ | $CH_3$ | H | 384.2 |
| 47 | $OCH_3$ | H | H | H | $OCH_3$ | F | $CH_3$ | $CH_3$ | H | 308.2 |
| 48 | F | F | F | F | F | F | $C_2H_5$ | $CH_3$ | H | 352.0 |
| 49 | F | F | F | F | F | F | $C_2H_5$ | $C_2H_5$ | H | 366.0 |
| 50 | F | F | F | F | F | F | $C_3H_7$ | $C_2H_5$ | H | 380.1 |
| 51 | F | H | H | H | F | $CH_3$ | $CH_3$ | $CH_3$ | H | 256.2 |
| 52 | F | F | F | F | F | $CH_3$ | $CH_3$ | $CH_3$ | H | 334.2 |
| 53 | F | F | F | F | F | $CH_3$ | =$CH_2$ | | H | 318.3 |
| 54 | F | H | H | F | F | H | —$CH_2$—$CH_2$— | | H | 264.3 |
| 55 | F | F | F | F | F | H | —$CH_2$—$CH_2$— | | H | 300.3 |
| 56 | F | F | F | F | F | H | —$CH_2$—$CH_2$— | | H | 318.1 |
| 57 | F | F | F | F | F | H | —$(CH_2)_3$— | | H | 332.3 |
| 58 | F | F | F | F | F | H | —$(CH_2)_4$— | | H | 346.3 |
| 59 | F | F | F | F | F | H | —$(CH_2)_5$— | | H | 360.3 |
| 60 | F | F | F | F | F | F | $CH_3$ | H | H | 323.9* |
| 61 | F | F | F | H | H | $OCH_3$ | $CH_3$ | $CH_3$ | H | 314.3 |
| 62 | F | F | F | F | F | $CH_3$ | $CH_2CH_3$ | H | H | 334.1 |
| 63 | F | F | F | F | F | cyclopropyl | $CH_3$ | H | H | 346.3 |
| 64 | F | F | F | F | F | CN | $CH_3$ | $CH_3$ | H | 345.3 |
| 65 | F | F | F | F | F | $CH_3$ | CO | | H | 320.2 |
| 66 | F | H | H | H | F | $CH_3$ | $CH_3$ | H | H | 266.2 |
| 67 | F | Cl | H | H | F | $CH_3$ | $CH_3$ | H | H | 300 |
| 68 | F | F | F | F | F | F | F | $CF_3$ | H | 395.9 |
| 69 | F | F | F | F | F | OH | $CH_3$ | H | H | 322.1 |
| 70 | F | H | H | H | F | F | $CH_2CH_3$ | $CH_3$ | H | 298 |
| 71 | F | H | CN | H | F | F | $CH_3$ | $CH_3$ | H | 309 |
| 72 | F | F | F | F | F | $CF_3$ | H | H | H | 360 |
| 73 | F | F | F | F | F | $CH_2CF_3$ | H | H | H | 374 |
| 74 | F | F | F | F | F | 1-$CH_3$-cyclo-hexyl | H | H | H | 406 |
| 75 | F | F | F | F | F | 1-$CH_3$-cyclo-hexyl | H | H | CO(1-$CH_3$-cyclohexyl) | 526 |
| 76 | Br | H | H | H | Br | F | $CH_3$ | $CH_3$ | H | 406 |
| 77 | F | Cl | H | H | F | F | $CH_2CH_3$ | $CH_3$ | H | 332 |
| 78 | F | H | H | H | F | Cl | $CH_3$ | $CH_3$ | H | 300.1 |
| 79 | F | H | H | $CF_3$ | H | F | $CH_3$ | $CH_3$ | H | 334.1 |
| 80 | F | F | H | H | F | $CH_3$ | $CH_3$ | $CH_3$ | H | 298.1 |

TABLE 1-continued

| no | $R^a$ | $R^b$ | $R^c$ | $R^d$ | $R^e$ | $R^2$ | $R^3$ | $R^4$ | $R^5$ | MS |
|---|---|---|---|---|---|---|---|---|---|---|
| 81 | F | Cl | H | H | F | $CH_3$ | $CH_3$ | $CH_3$ | H | 314.1 |
| 82 | F | F | F | F | F | $CH_2CH_3$ | $CH_3$ | $CH_3$ | H | 348.2 |
| 83 | F | F | F | F | F | $CH_2CH_3$ | $CH_2CH_3$ | H | H | 348.1 |
| 84 | F | F | F | F | F | Cl | $CH_3$ | H | H | 340.1 |
| 85 | F | H | H | H | F | H | —$(CH_2)_3$— | | H | 278.1 |
| 86 | F | H | H | H | F | H | —$(CH_2)_4$— | | H | 292.2 |
| 87 | F | H | H | H | F | H | —$(CH_2)_5$— | | H | 306.2 |
| 88 | F | F | F | F | F | $CH_3$ | —$(CH_2)_5$— | | H | 374.2 |
| 89 | F | F | H | F | F | F | $CH_2CH_3$ | $CH_3$ | H | 334.1 |
| 90 | F | F | F | F | F | $CH_3$ | —$(CH_2)_4$— | | H | 360.1 |
| 91 | F | F | H | H | F | $CH_3$ | $CH_3$ | $CH_3$ | H | 316.4 |
| 92 | F | F | F | F | F | $CH(CH_3)_2$ | $CH_3$ | H | H | 348.3 |
| 93 | t-Bu | H | H | H | H | F | $CH_3$ | $CH_3$ | H | 304.4 |
| 94 | F | H | F | H | F | $CH_3$ | $CH_3$ | $CH_3$ | H | 298.1 |
| 95 | F | F | $OCH_3$ | F | F | F | $CH_3$ | $CH_3$ | H | 350 |
| 96 | F | F | F | F | F | Cl | —$(CH_2)_4$— | | H | 380 |
| 97 | F | H | Cl | H | F | F | $CH_3$ | $CH_3$ | H | 318 |
| 98 | F | H | C≡CH | H | F | F | $CH_3$ | $CH_3$ | H | 308 |
| 99 | F | $CH_3$ | Cl | H | F | F | $CH_3$ | $CH_3$ | H | 332 |
| 100 | F | H | $CH_3$ | H | F | F | $CH_3$ | $CH_3$ | H | 298 |
| 101 | F | F | F | H | F | F | $CH_3$ | $CH_3$ | H | 320 |
| 102 | F | F | C≡CH | F | F | F | $CH_3$ | $CH_3$ | H | 344 |
| 103 | F | F | Br | F | F | F | $CH_3$ | $CH_3$ | H | 478.1 |
| 104 | F | H | H | H | F | $CH_2CH_3$ | H | H | H | 252.2 |
| 105 | F | H | H | H | F | F | F | F | H | 292.1 |
| 106 | F | Cl | H | H | $CF_3$ | F | $CH_3$ | $CH_3$ | H | 368.1 |
| 107 | $CF_3$ | H | H | H | F | F | $CH_3$ | $CH_3$ | H | 334.2 |
| 108 | F | Cl | H | H | F | Cl | $CH_3$ | $CH_3$ | H | 334.1 |
| 109 | $SO_2CH_3$ | H | H | H | F | F | $CH_3$ | $CH_3$ | H | 344.2 |
| 110 | F | F | H | H | F | F | $CH_3$ | H | H | 288.1 |
| 111 | F | F | H | F | F | Cl | $CH_3$ | $CH_3$ | H | 336.1 |
| 112 | F | F | H | H | F | Cl | $CH_3$ | $CH_3$ | H | 318.1 |
| 113 | CN | H | H | H | F | Cl | $CH_3$ | $CH_3$ | H | 307.1 |
| 114 | F | F | H | H | F | F | $CH_3$ | $CH_2CH_3$ | H | 316.1 |
| 115 | F | F | F | F | F | F | $CH_3$ | $CH_3$ | acetyl | 380 |
| 116 | F | H | $OCH_3$ | H | F | F | $CH_3$ | $CH_3$ | H | 314 |
| 117 | F | H | F | H | F | =CH—$CH_2$—$CH_2$—$CH_2$— | | | H | 308 |
| 118 | F | F | H | F | F | =CH—$CH_2$—$CH_2$—$CH_2$— | | | H | 326 |
| 119 | F | F | H | H | F | =CH—$CH_2$—$CH_2$—$CH_2$— | | | H | 308 |
| 120 | F | H | H | H | F | =CH—$CH_2$—$CH_2$—$CH_2$— | | | H | 290 |
| 121 | F | F | F | F | F | F | F | H | H | 328.1 |
| 122 | F | H | H | H | F | F | F | H | H | 274.1 |
| 123 | F | F | H | H | F | F | F | H | H | 292.1 |
| 124 | F | H | F | H | F | $CH_3$ | =$CHCH_3$[(E) conf] | | H | 278 |
| 125 | F | F | F | F | F | $CH_3$ | =$CHCH_3$[(E) conf] | | H | 332 |
| 126 | F | Cl | H | H | F | F | F | F | H | 326 |
| 127 | F | F | H | H | F | F | F | F | H | 310.1 |
| 128 | F | F | Cl | F | F | F | $CH_3$ | $CH_3$ | H | 354 |
| 129 | Cl | F | H | H | F | F | $CH_3$ | H | H | 304.1 |
| 130 | F | H | H | H | Br | F | F | F | H | 352 |
| 131 | F | H | H | H | Cl | F | F | F | H | 308.1 |
| 132 | F | F | H | F | F | F | F | F | H | 328 |
| 133 | F | F | F | F | F | F | F | F | H | 346.1 |
| 134 | F | H | F | H | F | F | F | F | H | 310 |
| 135 | CN | H | H | H | F | $CH_3$ | $CH_3$ | $CH_3$ | H | 287.1 |
| 136 | F | F | H | F | F | $CH_3$ | $CH_3$ | $CH_2CH_3$ | H | 330.2 |
| 137 | F | H | H | H | F | F | $CH_3$ | $CH_2CH_3$ | H | 316.1 |
| 138 | F | H | F | H | F | F | F | $CH_3$ | H | 306.1 |
| 139 | F | H | F | H | F | H | —$(CH_2)_5$— | | H | 324.2 |
| 140 | F | H | F | H | F | H | —$(CH_2)_4$— | | H | 310.2 |
| 141 | F | H | F | H | F | H | H | $C_3H_5$ | H | 296.2 |
| 142 | F | H | F | H | F | H | —$(CH_2)_3$— | | H | 296.2 |
| 143 | F | H | F | H | F | H | —$CH_2$—$CH_2$— | | H | 282.2 |
| 144 | F | H | F | H | F | $CH_3$ | —$(CH_2)_4$— | | H | 324.2 |
| 145 | F | H | F | H | F | $CH_3$ | —$(CH_2)_5$— | | H | 338.2 |
| 146 | F | F | F | F | F | F | F | Cl | H | 362 |
| 147 | F | F | F | F | F | Cl | Cl | $CH_3$ | H | 374 |
| 148 | F | F | H | H | F | $CH_3$ | $CH_3$ | H | H | 284.1 |
| 149 | F | H | H | H | CN | F | F | H | H | 281.1 |
| 150 | F | F | H | H | F | F | F | H | H | 310.1 |
| 151 | F | H | H | H | CN | F | F | F | H | 299.1 |
| 152 | Cl | F | H | H | F | F | F | H | H | 308.1 |
| 153 | F | Cl | H | H | F | F | F | H | H | 308.1 |
| 154 | Cl | F | H | H | F | F | F | F | H | 326 |
| 155 | F | H | H | H | methoxy-carbonyl | F | F | F | H | 332.1 |
| 156 | F | H | F | H | Cl | F | F | H | H | 308.1 |
| 157 | F | H | Br | H | H | F | F | H | H | 334 |

TABLE 1-continued

| no | $R^a$ | $R^b$ | $R^c$ | $R^d$ | $R^e$ | $R^2$ | $R^3$ | $R^4$ | $R^5$ | MS |
|---|---|---|---|---|---|---|---|---|---|---|
| 158 | F | F | H | H | OCH$_3$ | F | F | F | H | 322.1 |
| 159 | F | F | Br | F | F | F | F | H | H | 389.9 |
| 160 | F | F | F | Br | F | CH$_3$ | CH$_3$ | CH$_3$ | H | 396 |
| 161 | F | F | H | F | F | Cl | —(CH$_2$)$_5$— | | H | 376 |
| 162 | F | F | F | F | F | Cl | —(CH$_2$)$_5$— | | H | 394 |
| 163 | F | F | H | F | F | Cl | —(CH$_2$)$_4$— | | H | 362 |
| 164 | F | F | F | F | F | Cl | CH$_2$Cl | CH$_3$ | H | 388 |
| 165 | F | F | F | F | F | H | —(CH$_2$)$_2$—CHCF$_3$—(CH$_2$)$_2$— | | H | 428 |
| 166 | F | F | F | F | F | H | —(CH$_2$)$_2$—CHCH$_2$CH$_3$—(CH$_2$)$_2$— | | H | 388 |
| 167 | F | F | F | F | F | H | —(CH$_2$)$_2$—CHOCH$_3$—(CH$_2$)$_2$— | | H | 390 |
| 168 | F | F | F | F | F | OCH$_3$ | CH$_3$ | H | H | 336.1 |
| 169 | F | F | H | H | F | H | —CH$_2$—CH$_2$—CH$_2$— | | H | 296.2 |
| 170 | F | H | methoxy-carbonyl | H | H | F | CH$_3$ | CH$_3$ | H | 324.1 |
| 171 | F | F | H | F | F | (CH$_2$)$_4$CH$_3$ | H | H | H | 330.1 |
| 172 | F | F | F | F | F | H | —(CH$_2$)$_2$—CHCH$_3$—(CH$_2$)$_2$— | | H | 474.1 |
| 173 | F | H | CO$_2$H | H | H | F | CH$_3$ | CH$_3$ | H | 310.1 |
| 174 | F | F | F | F | F | CH$_3$ | —CH$_2$—CH$_2$—CH$_2$— | | H | 346.1 |
| 175 | F | F | F | F | F | F | —(CF$_2$)$_5$— | | H | 558 |
| 176 | F | F | F | F | F | F | CH$_3$ | CH$_3$ | CH$_3$ | 352 |
| 177 | F | F | F | F | F | H | —(CH$_2$)$_2$—CHC(CH$_3$)$_3$—(CH$_2$)$_2$— | | H | 416 |
| 178 | F | F | F | F | F | H | —CH$_2$—CH$_2$—CH$_2$—CH$_2$— | | CH$_3$ | 360 |
| 179 | F | F | H | F | F | CN | CH$_3$ | CH$_3$ | H | 327 |
| 180 | F | F | Br | F | F | F | CH$_3$ | H | H | 384 |
| 181 | F | F | H | F | F | CH$_2$CH$_3$ | H | H | H | 288.1 |
| 182 | F | F | H | H | methoxy-carbonyl | F | F | F | H | 350.1 |
| 183 | F | F | Br | F | F | F | F | F | H | 408 |
| 184 | F | F | OH | F | F | F | CH$_3$ | CH$_3$ | H | 336.1 |
| 185 | F | H | OH | H | F | F | CH$_3$ | CH$_3$ | H | 300.1 |
| 186 | F | F | H | F | F | H | —CH$_2$—CH$_2$—CH$_2$— | | H | 314.1 |
| 187 | F | F | H | F | F | H | —(CH$_2$)$_2$—CHCH$_3$—(CH$_2$)$_2$— | | H | 356.1 |
| 188 | F | F | F | F | F | F | —(CH$_2$)$_4$— | | H | 364.1 |
| 189 | F | NO$_2$ | H | H | F | F | CH$_3$ | CH$_3$ | H | 329.1 |
| 190 | F | F | H | F | F | H | —(CH$_2$)$_5$— | | H | 342.2 |
| 191 | 3,5-dimethyl-phenoxy | H | H | H | F | F | CH$_3$ | CH$_3$ | H | 386.1 |
| 192 | F | F | H | C$_6$H$_5$ | F | F | CH$_3$ | CH$_3$ | H | 378.1 |
| 193 | F | F | H | F | F | CH$_2$CH$_3$ | CH$_3$ | H | H | 316.1 |
| 194 | F | F | Br | F | F | CH$_3$ | =CHCH$_3$[(Z) conf] | | H | 392 |
| 195 | F | F | Br | F | F | Cl | CH$_2$CH$_3$ | CH$_3$ | H | 430 |
| 196 | F | F | H | F | F | CN | (CH$_2$)$_3$CH$_3$ | H | H | 355 |
| 197 | F | F | H | H | F | CN | (CH$_2$)$_3$CH$_3$ | H | H | 337 |
| 198 | F | F | H | F | F | F | H | H | H | 292 |
| 199 | F | H | H | H | F | F | H | H | H | 256 |
| 200 | F | F | F | F | F | Cl | CH$_2$CH$_3$ | CH$_3$ | H | 368 |
| 201 | F | F | H | F | F | CN | H | H | H | 299 |
| 202 | F | F | H | F | F | F | CH$_2$CH$_3$ | H | H | 320 |
| 203 | F | F | Br | F | F | C$_6$H$_5$ | H | H | H | 428.1 |
| 204 | F | F | Br | F | F | CH$_2$CH$_3$ | H | H | H | 368 |
| 205 | F | F | H | F | F | Cl | CH$_2$CH$_3$ | CH$_3$ | H | 350.2 |
| 206 | F | F | H | F | F | CH$_3$ | =CHCH$_3$[(Z) conf] | | H | 314.2 |
| 207 | F | F | H | F | F | F | CH$_2$CH$_3$ | CH$_3$ | acetyl | 376.1 |
| 208 | F | F | H | H | F | H | —(CH$_2$)$_5$— | | H | 324.2 |
| 209 | F | F | Br | F | F | H | —(CH$_2$)$_5$— | | H | 420.1 |
| 210 | F | F | Br | F | F | H | —(CH$_2$)$_4$— | | H | 408 |
| 211 | F | F | H | F | F | H | —(CH$_2$)$_4$— | | H | 328.1 |
| 212 | F | F | H | H | F | H | —(CH$_2$)$_4$— | | H | 310.2 |
| 213 | F | F | F | F | F | | =CH—(CH$_2$)$_4$— | | H | 358.1 |
| 214 | F | F | H | H | F | CH$_3$ | =CHCH$_3$[(Z) conf] | | H | 296.2 |
| 215 | F | F | Br | F | F | CH$_2$CH$_3$ | CH$_3$ | H | H | 396 |
| 216 | F | F | H | F | F | CN | —CH$_2$—CH$_2$— | | H | 325 |
| 217 | F | F | Br | F | F | CH$_3$ | =CH$_2$ | | H | 378 |
| 218 | F | F | Br | F | F | Cl | CH$_3$ | CH$_3$ | H | 416 |
| 219 | F | F | H | F | F | CN | CH$_2$CH$_3$ | CH$_2$CH$_3$ | H | 355 |
| 220 | F | H | NO$_2$ | H | F | F | CH$_3$ | CH$_3$ | H | 329 |
| 221 | F | F | CN | F | F | F | CH$_3$ | CH$_3$ | H | 345 |
| 222 | F | F | acetyl | H | F | F | CH$_3$ | CH$_3$ | H | 344 |
| 223 | F | H | acetyl | H | F | F | CH$_3$ | CH$_3$ | H | 326 |
| 224 | Cl | F | H | H | F | Cl | CH$_3$ | CH$_3$ | H | 334.1 |
| 225 | F | F | H | F | F | CH$_3$ | cyclopropyl | H | H | 328.1 |
| 226 | F | F | F | F | F | OCH$_3$ | CH$_3$ | CH$_3$ | H | 350.1 |
| 227 | F | Cl | H | H | CF$_3$ | CH$_3$ | CH$_3$ | CH$_3$ | H | 364.1 |
| 228 | F | F | H | H | F | OCH$_3$ | CH$_3$ | H | H | 299.8 |
| 229 | F | H | H | H | F | OCH$_3$ | CH$_3$ | H | H | 281.8 |

TABLE 1-continued

| no | $R^a$ | $R^b$ | $R^c$ | $R^d$ | $R^e$ | $R^2$ | $R^3$ | $R^4$ | $R^5$ | MS |
|---|---|---|---|---|---|---|---|---|---|---|
| 230 | F | F | H | F | F | $OCH_3$ | $CH_3$ | H | H | 317.8 |
| 231 | F | Cl | H | H | F | $OCH_3$ | $CH_3$ | H | H | 315.8 |
| 232 | F | H | F | H | F | $OCH_3$ | $CH_3$ | H | H | 299.8 |
| 233 | F | F | F | F | F | H | —$(CH_2)_2$—$CHCF_3$—$(CH_2)_2$— | | H | 428.2 |
| 234 | F | F | F | F | F | H | —$(CH_2)_2$—$CHCF_3$—$(CH_2)_2$— | | H | 428.2 |
| 235 | F | Cl | F | H | F | F | $CH_3$ | $CH_3$ | H | 336 |
| 236 | F | H | H | H | F | H | —$(CH_2)_2$—$CHCH_3$—$(CH_2)_2$— | | H | 320.5 |
| 237 | F | F | H | H | F | H | —$(CH_2)_2$—$CHCH_3$—$(CH_2)_2$— | | H | 338.5 |
| 238 | H | H | H | H | H | F | $CH_3$ | $CH_3$ | H | 248.4 |
| 239 | F | H | F | H | F | H | —$(CH_2)_2$—$CHCH_3$—$(CH_2)_2$— | | H | 338.5 |
| 240 | F | F | Br | F | F | H | —$(CH_2)_2$—$CHCH_3$—$(CH_2)_2$— | | H | 435.7 |
| 241 | F | Cl | H | H | F | H | —$(CH_2)_2$—$CHCH_3$—$(CH_2)_2$— | | H | 353.8 |
| 242 | F | H | H | H | CN | F | $CH_3$ | H | H | 276.8 |
| 243 | F | F | Br | F | F | Cl | —$(CH_2)_4$— | | H | 442.2 |
| 244 | F | H | H | H | F | $CH_3$ | —$(CH_2)_5$— | | H | 356.6 |
| 245 | F | H | H | H | F | $CH_3$ | —$(CH_2)_5$— | | H | 320.5 |
| 246 | F | Cl | H | H | $CF_3$ | F | $CH_2CH_3$ | $CH_3$ | H | 382.5 |
| 247 | F | Cl | H | H | $CF_3$ | H | —$(CH_2)_5$— | | H | 390.6 |
| 248 | 3-methyl-phenoxy | H | H | H | H | F | $CH_3$ | $CH_3$ | H | 316 |
| 249 | F | F | H | F | F | $O(CH_2)_2OCH_3$ | H | H | H | 347.8 |
| 250 | F | F | H | F | F | $OCH_2CH_3$ | H | H | H | 317.8 |
| 251 | F | F | F | F | F | $O(CH_2)_2OCH_3$ | H | H | H | 365.7 |
| 252 | F | F | F | F | F | $OCH_2CH_3$ | H | H | H | 335.7 |
| 253 | F | F | H | F | F | $C(CH_3)_3$ | H | H | H | 329.8 |
| 254 | F | F | F | F | F | $C(CH_3)_3$ | H | H | H | 347.8 |
| 255 | F | F | H | F | F | $CH(CH_3)_2$ | H | H | H | 315.8 |
| 256 | F | F | F | F | F | $CH(CH_3)_2$ | H | H | H | 333.7 |
| 257 | F | F | H | F | F | $OCH_3$ | H | H | H | 304.4 |
| 258 | F | F | F | F | F | $OCH_3$ | H | H | H | 321.8 |
| 259 | 3-methyl-phenoxy | H | H | H | F | F | $CH_3$ | $CH_3$ | H | 372.1 |
| 260 | 3-fluoro-phenoxy | H | H | H | F | F | $CH_3$ | $CH_3$ | H | 358.2 |
| 261 | F | F | F | F | F | H | —$(CH_2)_5$— | | $CH_3$ | 374 |
| 262 | F | F | I | F | F | F | $CH_3$ | $CH_3$ | H | 446.6 |
| 263 | F | F | F | F | F | H | —$(CH_2)_2$—O—$(CH_2)_2$— | | H | 362.5 |
| 264 | F | F | H | F | F | H | —$(CH_2)_2$—O—$(CH_2)_2$— | | H | 344.5 |
| 265 | F | $CH_3$ | H | H | F | F | F | F | H | 306.1 |
| 266 | F | F | $CF_3$ | F | F | F | $CH_3$ | $CH_3$ | H | 387.8 |
| 267 | F | F | F | F | F | H | —$CHCH_3$—$CH_2$—$CHCH_3$—$CH_2$—$CHCH_3$— | | H | 402 |
| 268 | F | F | H | F | F | F | $CH_3$ | $CH_3$ | $CH_3$ | 334 |
| 269 | F | F | Br | F | F | F | $CH_3$ | $CH_3$ | $CH_3$ | 414 |
| 270 | F | F | F | F | F | $CF_3$ | $CH_3$ | H | H | 374 |
| 271 | F | H | $CF_3$ | H | F | F | $CH_3$ | $CH_3$ | H | 352 |
| 272 | F | F | H | F | F | H | H | $CH_2OCH_3$ | H | 318.6 |
| 273 | F | F | F | F | F | H | H | $CH_2OCH_3$ | H | 335.7 |
| 274 | F | F | H | F | F | $CH_3$ | —$(CH_2)_3$— | | H | 327.8 |
| 275 | F | F | H | H | F | $CH_3$ | —$(CH_2)_3$— | | H | 309.8 |
| 276 | F | H | H | F | F | $CH_3$ | —$(CH_2)_3$— | | H | 291.8 |
| 277 | F | F | H | F | F | $CH_3$ | —$(CH_2)_4$— | | H | 341.8 |
| 278 | F | Cl | H | H | F | $CH_3$ | —$(CH_2)_4$— | | H | 339.8 |
| 279 | F | F | H | H | F | $CH_3$ | —$(CH_2)_4$— | | H | 323.8 |
| 280 | F | H | H | H | F | $CH_3$ | —$(CH_2)_4$— | | H | 305.8 |
| 281 | F | F | Br | F | F | F | —$(CH_2)_4$— | | H | 426.4 |

*(R)-enantiomer

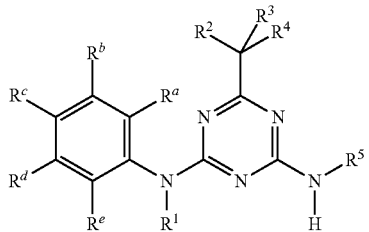

I wherein A is A.1

TABLE 2

| no | $R^a$ | $R^b$ | $R^c$ | $R^d$ | $R^e$ | $R^2$ | $R^3$ | $R^4$ | $R^5$ | $R^1$ | MS |
|---|---|---|---|---|---|---|---|---|---|---|---|
| 282 | F | H | H | H | F | H | —CH$_2$—CH$_2$— | | H | CO(cyclopropyl) | 332.3 |
| 283 | F | F | F | F | F | CH$_3$ | CH$_3$ | CH$_3$ | H | COC(CH$_3$)$_3$ | 418.3 |
| 284 | F | H | H | H | F | CH$_3$ | CH$_3$ | CH$_3$ | H | COC(CH$_3$)$_3$ | 280.2 |
| 285 | F | F | H | F | F | H | —CH$_2$—CH$_2$— | | H | CO(cyclopropyl) | 368.2 |
| 286 | F | F | H | F | F | CH$_3$ | CH$_3$ | CH$_3$ | H | COC(CH$_3$)$_3$ | 400.3 |
| 287 | F | F | F | F | F | OH | CH$_3$ | H | H | CH$_3$ | 336.1 |
| 288 | F | F | F | F | F | F | CH$_3$ | CH$_3$ | H | COCF(CH$_3$)$_2$ | 426 |
| 289 | F | Cl | H | H | F | F | CH$_3$ | CH$_3$ | H | COCF(CH$_3$)$_2$ | 406 |
| 290 | F | F | F | F | F | F | CH$_3$ | CH$_3$ | COCH$_3$ | COCH$_3$ | 422 |
| 291 | F | F | F | F | F | F | CH$_3$ | CH$_3$ | H | COCH$_3$ | 380 |
| 292 | F | F | Br | F | F | CH$_3$ | H | H | COCH$_2$CH$_3$ | COCH$_2$CH$_3$ | 478.1 |
| 293 | F | F | Br | F | F | CH$_3$ | CH$_3$ | H | COCH(CH$_2$)$_2$ | COCH(CH$_2$)$_2$ | 522.2 |
| 294 | F | F | H | H | F | F | CH$_3$ | CH$_3$ | H | COCH$_3$ | 344.1 |
| 295 | F | F | H | F | F | F | CH$_2$CH$_3$ | CH$_3$ | H | COCF(CH$_2$CH$_3$)CH$_3$ | 436.1 |
| 296 | F | H | F | H | F | H | —(CH$_2$)$_5$— | | H | COCH$_3$ | 366.2 |
| 297 | F | F | H | F | F | F | CH$_3$ | CH$_3$ | H | COCH$_3$ | 362.1 |
| 298 | F | H | H | H | F | F | CH$_2$CH$_3$ | CH$_3$ | H | COCH$_3$ | 340.1 |
| 299 | F | H | H | H | F | F | CH$_3$ | CH$_3$ | H | COCH$_3$ | 326.1 |
| 300 | F | F | H | F | F | F | CH$_2$CH$_3$ | CH$_3$ | COCH$_3$ | COCH$_3$ | 418.1 |
| 301 | F | F | H | F | F | F | CH$_2$CH$_3$ | CH$_3$ | H | COCH$_3$ | 376.1 |
| 302 | F | F | H | H | F | H | —(CH$_2$)$_4$— | | H | CO(cyclopentane) | 406.2 |
| 303 | F | F | F | F | F | =CH—CH$_2$—(CH$_2$)$_3$— | | | H | CO(cyclohex-1-ene) | 466.3 |
| 304 | F | F | H | F | F | H | —(CH$_2$)$_4$— | | H | Cyclopentane-carbonyl | 424.2 |
| 305 | F | F | F | F | F | F | CH$_3$ | CH$_3$ | H | CH$_2$OCH$_3$ | 382 |
| 306 | F | F | F | F | F | F | CH$_3$ | CH$_3$ | H | CH$_2$CH$_2$F | 384 |
| 307 | F | F | F | F | F | F | CH$_3$ | CH$_3$ | H | CH$_3$ | 352 |
| 308 | F | F | F | F | F | F | CH$_3$ | CH$_3$ | H | CH$_2$CH$_3$ | 366 |
| 309 | F | F | F | F | F | F | CH$_3$ | CH$_3$ | H | CH$_2$C$_6$H$_5$ | 428 |
| 310 | F | F | F | F | F | F | CH$_3$ | CH$_3$ | H | CH$_2$CH$_2$OMe | 396 |
| 311 | F | F | F | F | F | F | CH$_3$ | CH$_3$ | H | CH$_2$CF$_3$ | 420 |

B USE EXAMPLES

The herbicidal activity of the azines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A moderate herbicidal activity is given at values of at least 60, a good herbicidal activity is given at values of at least 70, and a very good herbicidal activity is given at values of at least 85.

The plants used in the greenhouse experiments were of the following species:

| Bayer code | Scientific name |
|---|---|
| ABUTH | *Abutilon theophrasti* |
| AMARE | *Amaranthus retroflexus* |
| APESV | *Apera spica-venti* |
| CAPBP | *Capsella bursa-pastoris* |
| CHEAL | *Chenopodium album* |
| ECHCG | *Echinocloa crus-galli* |
| GERDI | *Geranium dissectum* |
| LAMPU | *Lamium purpureum* |
| MATIN | *Matricaria maritima* |
| POAAN | *Poa annua* |
| POLCO | *Polygonum convolvulus* |
| SETFA | *Setaria faberi* |
| SETVI | *Setaria viridis* |
| STEME | *Stellaria media* |
| THLAR | *Thlaspi arvense* |
| VIOAR | *Viola arvensis* |

Example 1 applied by post-emergence method at an application rate of 0.125 kg/ha, showed very good herbicidal activity against AMARE and STEME.

Example 2 applied by post-emergence method at an application rate of 0.125 kg/ha, showed very good herbicidal activity against CHEAL and ECHCG.

Example 4 applied by pre-emergence method at an application rate of 0.125 kg/ha, showed very good herbicidal activity against CAPBP and LAMPU.

Example 5 applied by pre-emergence method at an application rate of 0.125 kg/ha, showed very good herbicidal activity against AMARE.

Example 6 applied by post-emergence method at an application rate of 0.031 kg/ha, showed very good herbicidal activity against AMARE and good herbicidal activity against POLCO.

Example 7 applied by post-emergence method at an application rate of 0.125 kg/ha, showed very good herbicidal activity against ABUTH and GERDI.

Example 8 applied by post-emergence method at an application rate of 0.062 kg/ha, showed very good herbicidal activity against ABUTH and CHEAL.

Example 9 applied by post-emergence method at an application rate of 0.062 kg/ha, showed very good herbicidal activity against ABUTH and GERDI.

Example 12 applied by pre-emergence method at an application rate of 0.125 kg/ha, showed very good herbicidal activity against CAPBP and VIOAR.

Example 15 applied by pre-emergence method at an application rate of 0.0625 kg/ha, showed moderate herbicidal activity against SETVI.

Example 16 applied by post-emergence method at an application rate of 0.125 kg/ha, showed good herbicidal activity against ABUTH, and moderate herbicidal activity against STEME.

Example 17 applied by post-emergence method at an application rate of 0.125 kg/ha, showed very good herbicidal activity against ABUTH and POLCO.

Examples 18 and 30 applied by post-emergence method at an application rate of 3 kg/ha, showed very good herbicidal activity against ABUTH and SETFA.

Example 19 applied by pre-emergence method at an application rate of 0.125 kg/ha, showed good herbicidal activity against VIOAR.

Example 22 applied by post-emergence method at an application rate of 0.125 kg/ha, showed good herbicidal activity against VIOAR.

Example 24 applied by pre-emergence method at an application rate of 0.125 kg/ha, showed very good herbicidal activity against SETVI and POLCO.

Example 25 applied by pre-emergence method at an application rate of 0.125 kg/ha, showed very good herbicidal activity against VIOAR.

Example 26 applied by pre-emergence method at an application rate of 0.125 kg/ha, showed very good herbicidal activity against VIOAR and good herbicidal activity against CAPBP.

Example 27 applied by post-emergence method at an application rate of 0.062 kg/ha, showed very good herbicidal activity against AMARE and ECHGC.

Example 28 applied by post-emergence method at an application rate of 0.125 kg/ha, showed very good herbicidal activity against ABUTH and AMARE.

Example 29 applied by pre-emergence method at an application rate of 0.125 kg/ha, showed moderate herbicidal activity against VIOAR.

Example 31 applied by post-emergence method at an application rate of 0.031 kg/ha, showed very good herbicidal activity against AMARE.

Example 32 applied by post-emergence method at an application rate of 0.062 kg/ha, showed very good herbicidal activity against GERDI and POLCO.

Example 34 applied by pre-emergence method at an application rate of 0.125 kg/ha, showed very good herbicidal activity against CAPBP and STEME.

Example 35 applied by post-emergence method at an application rate of 0.062 kg/ha, showed very good herbicidal activity against ABUTH and STEME.

Example 36 applied by post-emergence method at an application rate of 0.062 kg/ha, showed very good herbicidal activity against ABUTH and AMARE.

Examples 37 and 54 applied by post-emergence method at an application rate of 0.125 kg/ha, showed moderate herbicidal activity against AMARE.

Example 38 applied by post-emergence method at an application rate of 0.125 kg/ha, showed very good herbicidal activity against AMARE and CHEAL.

Example 39 applied by pre-emergence method at an application rate of 0.031 kg/ha, showed moderate herbicidal activity against APESV.

Example 40 applied by post-emergence method at an application rate of 0.031 kg/ha, showed very good herbicidal activity against AMARE and CHEAL.

Example 41 applied by pre-emergence method at an application rate of 0.031 kg/ha, showed good herbicidal activity against AMARE.

Example 42 applied by pre-emergence method at an application rate of 0.0625 kg/ha, showed very good herbicidal activity against AMARE.

Example 43 applied by post-emergence method at an application rate of 0.031 kg/ha, showed good herbicidal activity against AMARE.

Example 44 applied by pre-emergence method at an application rate of 0.125 kg/ha, showed very good herbicidal activity against ABUTH and AMARE.

Example 46 applied by pre-emergence method at an application rate of 0.125 kg/ha, showed very good herbicidal activity against THLAR.

Examples 47 applied by pre-emergence method at an application rate of 0.125 kg/ha, showed very good herbicidal activity against AMARE.

Example 48 applied by post-emergence method at an application rate of 0.125 kg/ha, showed very good herbicidal activity against AMARE and STEME.

Example 49 applied by post-emergence method at an application rate of 0.125 kg/ha, showed very good herbicidal activity against CHEAL and GERDI.

Example 50 applied by pre-emergence method at an application rate of 0.125 kg/ha, showed very good herbicidal activity against CAPBP and STEME.

Example 51 applied by pre-emergence method at an application rate of 0.125 kg/ha, showed very good herbicidal activity against ABUTH and AMARE.

Example 52 applied by post-emergence method at an application rate of 0.062 kg/ha, showed very good herbicidal activity against ABUTH and GERDI.

Example 53 applied by pre-emergence method at an application rate of 0.125 kg/ha, showed very good herbicidal activity against AMARE and a good herbicidal activity against SETFA.

Examples 55 and 56 applied by post-emergence method at an application rate of 0.062 kg/ha, showed very good herbicidal activity against AMARE and CHEAL.

Example 57 applied by post-emergence method at an application rate of 0.062 kg/ha, showed very good herbicidal activity against AMARE and ECHCG.

Examples 58 and 59 applied by post-emergence method at an application rate of 0.125 kg/ha, showed very good herbicidal activity against AMARE and CHEAL.

Example 61 applied by post-emergence method at an application rate of 0.062 kg/ha, showed very good herbicidal activity against AMARE and POLCO.

Example 62 applied by pre-emergence method at an application rate of 125 g/ha showed very good herbicidal activity against CAPBP, SETVI and STEME.

Example 63 applied by pre-emergence method at an application rate of 125 g/ha showed very good herbicidal activity against ECHCG, SETVI and STEME.

Example 64 applied by pre-emergence method at an application rate of 125 g/ha showed very good herbicidal activity against ABUTH, AMARE and STEME.

Example 66 applied by pre-emergence method at an application rate of 62.5 g/ha showed very good herbicidal activity against AMARE.

Example 67 applied by pre-emergence method at an application rate of 125 g/ha showed very good herbicidal activity against AMARE and good herbicidal activity against ABUTH.

Example 68 applied by pre-emergence method at an application rate of 125 g/ha showed very good herbicidal activity against AMARE, CAPBP and STEME.

Example 69 applied by pre-emergence method at an application rate of 2000 g/ha showed very good herbicidal activity against MATIN and POAAN.

Examples 70 and 77, 82, 89 applied by pre-emergence method at an application rate of 125 g/ha showed very good herbicidal activity against CAPBP, SETVI and STEME.

Example 71 applied by post-emergence method at an application rate of 125 g/ha showed very good herbicidal activity against CHEAL and good herbicidal activity against POLCO.

Example 72 applied by pre-emergence method at an application rate of 125 g/ha showed very good herbicidal activity against ABUTH and AMARE.

Example 73 applied by pre-emergence method at an application rate of 250 g/ha showed very good herbicidal activity against CAPBP, SETVI and STEME.

Example 75 applied by pre-emergence method at an application rate of 1000 g/ha showed good herbicidal activity against AMARE.

Example 78 applied by pre-emergence method at an application rate of 125 g/ha showed good herbicidal activity against APESV.

Examples 79 and 85, 86, 87 applied by pre-emergence method at an application rate of 125 g/ha showed very good herbicidal activity against AMARE.

Example 80 applied by pre-emergence method at an application rate of 125 g/ha showed very good herbicidal activity against CAPBP, ECHCG and STEME.

Example 81 applied by pre-emergence method at an application rate of 125 g/ha showed very good herbicidal activity against CAPBP, STEME and VIOAR.

Example 83 applied by pre-emergence method at an application rate of 250 g/ha showed very good herbicidal activity against CAPBP, ECHCG and STEME.

Examples 84, 110 applied by pre-emergence method at an application rate of 125 g/ha showed very good herbicidal activity against ABUTH, AMARE and SETFA.

Example 88 applied by pre-emergence method at an application rate of 125 g/ha showed very good herbicidal activity against CAPBP, LAMPU and STEME.

Examples 91, 101, 103, 106, 107, 112 applied by pre-emergence method at an application rate of 125 g/ha showed very good herbicidal activity against ECHCG, SETVI and STEME.

Examples 92, 136, 137 applied by pre-emergence method at an application rate of 125 g/ha showed very good herbicidal activity against CAPBP, SETVI and STEME.

Examples 96, 102, 113, 290, 148, 163 applied by pre-emergence method at an application rate of 250 g/ha showed very good herbicidal activity against CAPBP, SETVI and STEME.

Example 97 applied by pre-emergence method at an application rate of 250 g/ha showed good herbicidal activity against CAPBP and LAMPU.

Examples 104, 134 applied by pre-emergence method at an application rate of 500 g/ha showed good herbicidal activity against AMARE.

Example 108 applied by pre-emergence method at an application rate of 250 g/ha showed very good herbicidal activity against CAPBP, STEME and VIOAR.

Example 111 applied by pre-emergence method at an application rate of 125 g/ha showed very good herbicidal activity against CAPBP, ECHCG and SETVI.

Example 114 applied by pre-emergence method at an application rate of 32 g/ha showed very good herbicidal activity against ECHCG, POLCO and SETVI.

Examples 115, 288, 289 applied by pre-emergence method at an application rate of 1000 g/ha showed very good herbicidal activity against ABUTH, AMARE and ECHCG.

Example 116 applied by pre-emergence method at an application rate of 1000 g/ha showed very good herbicidal activity against APESV and good herbicidal activity against AMARE.

Example 117, 120 applied by post-emergence method at an application rate of 1000 g/ha showed good herbicidal activity against AMARE.

Examples 118, 125 applied by pre-emergence method at an application rate of 500 g/ha showed very good herbicidal activity against CAPBP, STEME and VIOAR.

Examples 119, 184 applied by pre-emergence method at an application rate of 1000 g/ha showed very good herbicidal activity against AMARE.

Example 121 applied by pre-emergence method at an application rate of 250 g/ha showed very good herbicidal activity against ABUTH and AMARE.

Example 123 applied by pre-emergence method at an application rate of 250 g/ha showed very good herbicidal activity against AMARE and good herbicidal activity against ABUTH and ECHCG.

Example 124 applied by pre-emergence method at an application rate of 1000 g/ha showed very good herbicidal activity against ABUTH, AMARE and ECHCG.

Example 126 applied by post-emergence method at an application rate of 1000 g/ha showed very good herbicidal activity against AMARE and good herbicidal activity against ABUTH.

Example 127 applied by post-emergence method at an application rate of 1000 g/ha showed very good herbicidal activity against AMARE and CHEAL, and good herbicidal activity against POLCO.

Example 128 applied by pre-emergence method at an application rate of 125 g/ha showed very good herbicidal activity against POAAN and good herbicidal activity against VIOAR.

Examples 129, 133, 170 applied by pre-emergence method at an application rate of 500 g/ha showed very good herbicidal activity against AMARE.

Example 132 applied by post-emergence method at an application rate of 500 g/ha showed very good herbicidal activity against AMARE, CHEAL and POLCO.

Example 135 applied by pre-emergence method at an application rate of 500 g/ha showed very good herbicidal activity against ABUTH, AMARE and ECHCG.

Example 138 applied by pre-emergence method at an application rate of 125 g/ha showed very good herbicidal activity against CAPBP, STEME and VIOAR.

Examples 139, 140 applied by pre-emergence method at an application rate of 250 g/ha showed good herbicidal activity against VIOAR.

Example 141 applied by pre-emergence method at an application rate of 1000 g/ha showed very good herbicidal activity against AMARE and SETFA and good herbicidal activity against ECHCG.

Example 142 applied by pre-emergence method at an application rate of 500 g/ha showed very good herbicidal activity against AMARE and good herbicidal activity against ABUTH and SETFA.

Example 143 applied by post-emergence method at an application rate of 500 g/ha showed very good herbicidal activity against AMARE and CHEAL, and good herbicidal activity against POLCO.

Example 146 applied by post-emergence method at an application rate of 500 g/ha showed very good herbicidal activity against AMARE, CHEAL and POLCO.

Example 147 applied by pre-emergence method at an application rate of 250 g/ha showed very good herbicidal activity against AMARE, ECHCG and SETFA.

Example 149 applied by pre-emergence method at an application rate of 250 g/ha showed good herbicidal activity against STEME.

Example 150 applied by pre-emergence method at an application rate of 500 g/ha showed very good herbicidal activity against ABUTH, AMARE and SETFA.

Example 151 applied by post-emergence method at an application rate of 500 g/ha showed good herbicidal activity against ABUTH.

Example 157 applied by post-emergence method at an application rate of 500 g/ha showed very good herbicidal activity against ABUTH and ECHCG.

Example 158 applied by post-emergence method at an application rate of 1000 g/ha showed very good herbicidal activity against ABUTH.

Example 160 applied by pre-emergence method at an application rate of 125 g/ha showed very good herbicidal activity against CAPBP, LAMPU and STEME.

Examples 161, 162, 164 applied by pre-emergence method at an application rate of 250 g/ha showed very good herbicidal activity against CAPBP, STEME and VIOAR.

Example 165 applied by pre-emergence method at an application rate of 1000 g/ha showed very good herbicidal activity against AMARE, ECHGC and SETFA.

Examples 166, 178, 183, 292, 293 applied by post-emergence method at an application rate of 1000 g/ha showed very good herbicidal activity against ABUTH, AMARE and SETVI.

Example 167 applied by pre-emergence method at an application rate of 500 g/ha showed very good herbicidal activity against AMARE and SETFA, and good herbicidal activity against ABUTH.

Examples 168, 176 applied by pre-emergence method at an application rate of 1000 g/ha showed very good herbicidal activity against ABUTH, AMARE and ECHCG.

Examples 169, 174 applied by pre-emergence method at an application rate of 250 g/ha showed very good herbicidal activity against CAPBP, SETVI and STEME.

Example 171 applied by pre-emergence method at an application rate of 250 g/ha showed very good herbicidal activity against CAPBP, ECHCG and STEME.

Example 172 applied by pre-emergence method at an application rate of 250 g/ha showed very good herbicidal activity against AMARE and ECHCG, and good herbicidal activity against ABUTH.

Example 173 applied by post-emergence method at an application rate of 500 g/ha showed good herbicidal activity against ECHCG.

Example 175 applied by pre-emergence method at an application rate of 494 g/ha showed good herbicidal activity against APESV.

Example 177 applied by pre-emergence method at an application rate of 500 g/ha showed very good herbicidal activity against AMARE and good herbicidal activity against SETFA.

Examples 179, 186, 187 applied by pre-emergence method at an application rate of 250 g/ha showed very good herbicidal activity against ABUTH, AMARE and ECHCG.

Example 180 applied by pre-emergence method at an application rate of 250 g/ha showed very good herbicidal activity against ABUTH and AMARE.

Examples 181, 202 applied by pre-emergence method at an application rate of 500 g/ha showed very good herbicidal activity against ABUTH, AMARE and ECHCG.

Examples 188, 190, 294, 295 applied by pre-emergence method at an application rate of 125 g/ha showed very good herbicidal activity against AMARE, ECHCG and SETFA.

Example 189 applied by pre-emergence method at an application rate of 507 g/ha showed very good herbicidal activity against ABUTH, AMARE and ECHCG.

Example 191 applied by pre-emergence method at an application rate of 1000 g/ha showed very good herbicidal activity against ABUTH, AMARE and ECHCG.

Example 192 applied by post-emergence method at an application rate of 1000 g/ha showed very good herbicidal activity against ABUTH, AMARE and ECHCG.

Example 193 applied by pre-emergence method at an application rate of 500 g/ha showed very good herbicidal activity against ABUTH, AMARE and ECHCG.

Example 194 applied by pre-emergence method at an application rate of 500 g/ha showed good herbicidal activity against SETFA.

Example 195 applied by pre-emergence method at an application rate of 500 g/ha showed very good herbicidal activity against AMARE, and good herbicidal activity against ABUTH and ECHCG.

Examples 196, 201 applied by pre-emergence method at an application rate of 1000 g/ha showed very good herbicidal activity against AMARE, ECHCG and SETFA.

Example 197 applied by pre-emergence method at an application rate of 1000 g/ha showed good herbicidal activity against SETFA.

Example 198 applied by pre-emergence method at an application rate of 119 g/ha showed very good herbicidal activity against AMARE.

Example 200 applied by pre-emergence method at an application rate of 1000 g/ha showed very good herbicidal activity against CACBP, ECHCG and POLCO.

Examples 204, 213 applied by pre-emergence method at an application rate of 500 g/ha showed good herbicidal activity against AMARE.

Example 205 applied by pre-emergence method at an application rate of 125 g/ha showed very good herbicidal activity against AMARE, ECHCG and SETFA.

Example 206 applied by pre-emergence method at an application rate of 500 g/ha showed very good herbicidal activity against AMARE.

Example 207 applied by pre-emergence method at an application rate of 125 g/ha showed very good herbicidal activity against CAPBP, SETVI and STEME.

Example 209 applied by pre-emergence method at an application rate of 250 g/ha showed very good herbicidal activity against STEME, and good herbicidal activity against CAPBP and VIOAR.

Example 210 applied by pre-emergence method at an application rate of 250 g/ha showed very good herbicidal activity against CAPBP, STEME and VIOAR.

Example 212 applied by pre-emergence method at an application rate of 500 g/ha showed very good herbicidal activity against AMARE, ECHCG and SETFA.

Example 216 applied by pre-emergence method at an application rate of 250 g/ha showed very good herbicidal activity against AMARE, and good herbicidal activity against ABUTH and SETFA.

Examples 218, 226, 230 applied by pre-emergence method at an application rate of 500 g/ha showed very good herbicidal activity against ABUTH, AMARE and SETFA.

Example 219 applied by pre-emergence method at an application rate of 250 g/ha showed very good herbicidal activity against ABUTH and AMARE.

Example 220 applied by pre-emergence method at an application rate of 500 g/ha showed good herbicidal activity against SETFA.

Example 228 applied by pre-emergence method at an application rate of 500 g/ha showed very good herbicidal activity against ABUTH and AMARE.

Example 283 applied by post-emergence method at an application rate of 62 g/ha showed very good herbicidal activity against AMARE and good herbicidal activity against SETVI.

Example 285 applied by post-emergence method at an application rate of 62 g/ha showed very good herbicidal activity against AMARE and good herbicidal activity against CHEAL.

Example 286 applied by pre-emergence method at an application rate of 125 g/ha showed very good herbicidal activity against ABUTH, AMARE and SETFA.

Example 291 applied by pre-emergence method at an application rate of 2000 g/ha showed very good herbicidal activity against MATIN and POAAN.

Example 302 applied by pre-emergence method at an application rate of 1000 g/ha showed very good herbicidal activity against AMARE and ECHCG, and good herbicidal activity against ABUTH.

Example 303 applied by post-emergence method at an application rate of 500 g/ha showed good herbicidal activity against ABUTH and AMARE.

Example 304 applied by pre-emergence method at an application rate of 1000 g/ha showed very good herbicidal activity against AMARE, ECHCG and SETFA.

Example 305 applied by pre-emergence method at an application rate of 500 g/ha showed very good herbicidal activity against POLCO, STEME and VIOAR.

Example 307 applied by pre-emergence method at an application rate of 125 g/ha showed very good herbicidal activity against AMARE and SETFA.

Example 308 applied by pre-emergence method at an application rate of 125 g/ha showed very good herbicidal activity against AMARE.

The invention claimed is:

1. A compound of formula (I)

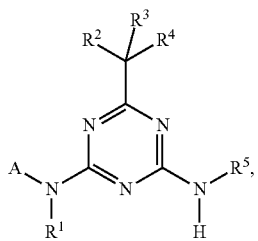

I wherein
A is 2-fluoro-phenyl, which is substituted by one to four substituents selected from the group consisting of halogen, CN, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl and ($C_1$-$C_6$-alkoxy)carbonyl;

$R^1$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

$R^2$ H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
wherein the $C_3$-$C_6$-cycloalkyl, $C_3$-$C_6$-cycloalkenyl or and three- to six-membered heterocyclyl is unsubstituted or substituted by one to three substituents selected from halogen, CN, $C_1$-$C_6$-alkyl and $C_1$-$C_6$-alkoxy; and $R^5$ H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, $NO_2$, $C_1$-$C_6$-alkyl, $C_1$-$C_6$-haloalkyl and $C_1$-$C_6$-alkoxy;

including their agriculturally acceptable salts or N-oxides.

2. The compound of claim 1, wherein A is 2-fluoro-phenyl, which is substituted by one to three substituents selected from the group consisting of halogen, CN, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl.

3. The compound of claim 1, wherein $R^1$ and $R^5$ independently of one another are H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl.

4. The compound of claim 1, wherein $R^2$ is H, halogen, $C_1$-$C_6$-alkyl or $C_1$-$C_6$-haloalkyl.

5. The compound of claim 1, wherein A is 2-fluoro-phenyl, which is substituted by one to three substituents selected from the group consisting of halogen, CN, $C_1$-$C_6$-alkyl and $C_1$-$C_6$-alkoxy.

6. A process for the compound of claim 1, wherein $R^1$ and $R^5$ independently of one another are H, $C_1$-$C_6$-alkyl, $C_1$-$C_6$-alkoxy-$C_1$-$C_6$-alkyl or $C_1$-$C_6$-alkoxy;

comprising reacting biguanidines of formula (II)

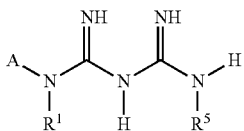

wherein $R^1$ and $R^5$ independently of one another are H, $C_1$-$C_6$-alkyl, $C_1$-$C_6$-alkoxy-$C_1$-$C_6$-alkyl or $C_1$-$C_6$-alkoxy;
with carbonyl compounds of formula (III)

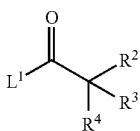

wherein
$L^1$ is halogen, CN, $C_1$-$C_6$-alkoxy, $C_1$-$C_6$-alkoxycarbonyl, $C_1$-$C_6$-alkylcarbonyloxy or $C_1$-$C_6$-alkoxycarbonyloxy;
in the presence of a base.

7. A process for the preparation of the compound of claim 1, wherein
$R^1$ and $R^5$ independently of one another are H, $C_1$-$C_6$-alkyl, $C_1$-$C_6$-alkoxy-$C_1$-$C_6$-alkyl or $C_1$-$C_6$-alkoxy;
comprising reacting halotriazines of formula (VI),

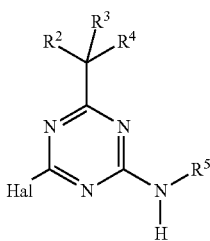

wherein $R^5$ is H, $C_1$-$C_6$-alkyl, $C_1$-$C_6$-alkoxy-$C_1$-$C_6$-alkyl or $C_1$-$C_6$-alkoxy; and
Hal is halogen;
with an amine of formula (V),

A-NHR$^1$     (V)

wherein $R^1$ is H, $C_1$-$C_6$-alkyl, $C_1$-$C_6$-alkoxy-$C_1$-$C_6$-alkyl or $C_1$-$C_6$-alkoxy;
in the presence of a base and a catalyst.

8. A process for the preparation of the compound of claim 1, wherein
$R^5$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, NO$_2$, $C_1$-$C_6$-alkyl, $C_1$-$C_6$-haloalkyl and $C_1$-$C_6$-alkoxy;
comprising reacting an azine of formula (I), wherein $R^5$ is hydrogen,
with a compound of formula (IX)

R$^5$—X     (IX)

wherein
$R^5$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, NO$_2$, $C_1$-$C_6$-alkyl, $C_1$-$C_6$-haloalkyl and $C_1$-$C_6$-alkoxy; and
X is halogen or oxycarbonyl-$C_1$-$C_6$-alkyl.

9. A process for the preparation of a compound of claim 1, wherein
$R^1$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, NO$_2$, $C_1$-$C_6$-alkyl, $C_1$-$C_6$-haloalkyl and $C_1$-$C_6$-alkoxy;
comprising reacting an azine of formula (I), wherein $R^1$ is hydrogen,
with a compound of formula (X)

R$^1$—X     (X)

wherein
$R^1$ is CN, ($C_1$-$C_6$-alkyl)carbonyl, ($C_1$-$C_6$-alkoxy)carbonyl, ($C_1$-$C_6$-alkyl)sulfonyl or phenylsulfonyl,
wherein the phenyl is unsubstituted or substituted by one to five substituents selected from the group consisting of halogen, CN, NO$_2$, $C_1$-$C_6$-alkyl, $C_1$-$C_6$-haloalkyl and $C_1$-$C_6$-alkoxy; and
X is halogen or oxycarbonyl-$C_1$-$C_6$-alkyl.

10. An agrochemical composition comprising a herbicidally active amount of at least a compound of claim 1 and at least one inert liquid and/or solid carrier and, if appropriate, at least one surface-active substance.

11. A process for the preparation of herbicidal active agrochemical compositions, which comprises mixing an herbicidally active amount of at least a compound of claim 1 and at least one inert liquid and/or solid carrier and, if desired, at least one surface-active substance.

12. A method of controlling undesired vegetation, which comprises allowing an herbicidally active amount of at least a compound of claim 1 to act on plants, their environment or on seed.

13. A method for the desiccation/defoliation of plants, which comprises allowing at least a compound of claim 1 to act on plants.

14. The method of claim 12, wherein, in the compound of formula (I), A is 2-fluoro-phenyl, which is substituted by one to three substituents selected from the group consisting of halogen, CN, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl.

15. The method of claim 12, wherein, in the compound of formula (I), $R^1$ and $R^5$ independently of one another are H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl.

16. The method of claim 12, wherein, in the compound of formula (I), $R^2$ is H, halogen, $C_1$-$C_6$-alkyl or $C_1$-$C_6$-haloalkyl.

17. The method of claim 12, wherein, in the compound of formula (I), A is 2-fluoro-phenyl, which is substituted by one to three substituents selected from the group consisting of halogen, CN, $C_1$-$C_6$-alkyl and $C_1$-$C_6$-alkoxy.

18. The method of claim 13, wherein, in the compound of formula (I), A is 2-fluoro-phenyl, which is substituted by one to three substituents selected from the group consisting of halogen, CN, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)carbonyl, ($C_1$-$C_6$-alkoxy)carbonyl.

19. The method of claim 13, wherein, in the compound of formula (I), $R^1$ and $R^5$ independently of one another are H, CN, $C_1$-$C_6$-alkyl, $C_1$-$C_6$-haloalkyl, $C_1$-$C_6$-alkoxy-$C_1$-$C_6$-alkyl, $C_1$-$C_6$-alkoxy, ($C_1$-$C_6$-alkyl)carbonyl or ($C_1$-$C_6$-alkyl)sulfonyl.

20. The method of claim 13, wherein, in the compound of formula (I), $R^2$ is H, halogen, $C_1$-$C_6$-alkyl or $C_1$-$C_6$-haloalkyl.

21. The method of claim 13, wherein, in the compound of formula (I), A is 2-fluoro-phenyl, which is substituted by one to three substituents selected from the group consisting of halogen, CN, $C_1$-$C_6$-alkyl and $C_1$-$C_6$-alkoxy.

* * * * *